(12) United States Patent
Robinson et al.

(10) Patent No.: US 12,402,792 B2
(45) Date of Patent: Sep. 2, 2025

(54) SYSTEM AND METHOD FOR DETERMINING SEGMENTS FOR ABLATION

(71) Applicant: Washington University, St. Louis, MO (US)

(72) Inventors: Clifford Robinson, St. Louis, MO (US); Phillip Cuculich, St. Louis, MO (US); Geoffrey Hugo, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/771,981

(22) PCT Filed: Dec. 12, 2018

(86) PCT No.: PCT/US2018/065278
§ 371 (c)(1),
(2) Date: Jun. 11, 2020

(87) PCT Pub. No.: WO2019/118640
PCT Pub. Date: Jun. 20, 2019

(65) Prior Publication Data
US 2021/0137384 A1    May 13, 2021

Related U.S. Application Data

(60) Provisional application No. 62/607,084, filed on Dec. 18, 2017, provisional application No. 62/598,162, filed on Dec. 13, 2017.

(51) Int. Cl.
*A61B 5/00*    (2006.01)
*A61B 5/055*    (2006.01)
(Continued)

(52) U.S. Cl.
CPC .......... *A61B 5/0036* (2018.08); *A61B 5/0035* (2013.01); *A61B 5/0044* (2013.01);
(Continued)

(58) Field of Classification Search
CPC ..... A61B 5/0036; A61B 5/0044; A61B 5/055; A61B 5/364; A61B 6/032; A61B 6/037;
(Continued)

(56) References Cited

U.S. PATENT DOCUMENTS 1,092,551 A    4/1914    Worm
5,458,620 A    10/1995    Adams et al.
(Continued)

FOREIGN PATENT DOCUMENTS

EP    3092944 A1    11/2016
JP    2005505331 A    2/2005
(Continued)

OTHER PUBLICATIONS

Cuculich, Phillip S. et al., The Elecrophysiological Cardiac Ventricular Substrate in Patients After Myocardial Infarction, Journal of The American College of Cardiology, Jul. 12, 2011, pp. 1893-1902, vol. 58, No. 18, Elsevier, New York, NY (Year: 2011).*
(Continued)

*Primary Examiner* — Joel F Brutus
(74) *Attorney, Agent, or Firm* — Armstrong Teasdale LLP

(57) ABSTRACT

Disclosed herein are systems and methods for determining one or more cardiac arrhythmia targets for ablation. The method may include receiving one or more mappings, identifying an abnormality in the one or more mappings, combining the one or more mappings, and defining the one or more cardiac arrhythmia targets based on an overlap of the identified abnormality in the combined one or more mappings.

19 Claims, 37 Drawing Sheets

(51) Int. Cl.
  *A61B 5/364* (2021.01)
  *A61B 6/03* (2006.01)
  *A61B 8/14* (2006.01)
  *G16H 10/60* (2018.01)

(52) U.S. Cl.
  CPC .............. *A61B 5/055* (2013.01); *A61B 5/364* (2021.01); *A61B 5/7275* (2013.01); *A61B 6/032* (2013.01); *A61B 6/037* (2013.01); *A61B 8/14* (2013.01); *G16H 10/60* (2018.01)

(58) Field of Classification Search
  CPC ....... A61B 8/14; A61B 5/0035; A61B 5/7275; A61B 2505/05; A61B 5/361; A61B 5/363; A61B 5/367; A61B 5/7267; A61B 5/7425; G16H 10/60; G06T 2207/10081; G06T 2207/10088; G06T 2207/10104; G06T 2207/10108; G06T 2207/10132; G06T 2207/20081; G06T 2207/20084; G06T 2207/20104; G06T 2207/20128; G06T 2207/20212; G06T 2207/30048; G06T 7/0012; G06T 7/30
  See application file for complete search history.

(56) References Cited

U.S. PATENT DOCUMENTS

| | | |
|---|---|---|
| 6,772,004 B2 | 8/2004 | Rudy |
| 7,729,752 B2 | 6/2010 | Harlev et al. |
| 7,953,204 B2 | 5/2011 | Sumanaweera et al. |
| 8,702,688 B2 | 4/2014 | Melsky |
| 9,183,355 B2 | 11/2015 | Gustafson |
| 9,504,853 B2 | 11/2016 | Sumanaweera et al. |
| 2003/0088184 A1 | 5/2003 | Kelly |
| 2007/0299352 A1* | 12/2007 | Harlev ............ A61B 5/062 600/509 |
| 2008/0171931 A1 | 7/2008 | Maschke |
| 2009/0326362 A1* | 12/2009 | Carlse .................. G06T 7/30 600/420 |
| 2010/0106002 A1* | 4/2010 | Sugiyama ........ A61B 5/4064 345/660 |
| 2010/0191131 A1 | 7/2010 | Revishvili et al. |
| 2011/0268338 A1* | 11/2011 | Collins ............. G06T 7/0012 382/128 |
| 2013/0123773 A1* | 5/2013 | Schwartz .......... A61B 5/361 606/34 |
| 2013/0184697 A1* | 7/2013 | Han .................. A61B 90/37 606/32 |
| 2016/0022375 A1* | 1/2016 | Blake .............. G16H 50/00 600/424 |
| 2017/0079542 A1* | 3/2017 | Spector ............... A61B 5/35 |
| 2017/0161896 A1 | 6/2017 | Blake, III |
| 2017/0258348 A1 | 9/2017 | Erasala et al. |
| 2017/0262990 A1 | 9/2017 | Chang et al. |
| 2017/0290550 A1* | 10/2017 | Perschbacher ....... A61B 5/076 |
| 2018/0078146 A1* | 3/2018 | Shadforth .......... G06T 19/20 |

FOREIGN PATENT DOCUMENTS

| | | |
|---|---|---|
| JP | 2008173473 A | 7/2008 |
| JP | 2013537437 A | 10/2013 |
| JP | 2017042386 A | 3/2017 |
| WO | 2008115830 A2 | 9/2008 |
| WO | 2009042842 A1 | 4/2009 |
| WO | 2011009121 A1 | 1/2011 |
| WO | 2011159688 A2 | 12/2011 |
| WO | 2012109618 A2 | 8/2012 |
| WO | 2012151301 A1 | 11/2012 |
| WO | 2014118535 A2 | 8/2014 |
| WO | 2016014949 A1 | 1/2016 |
| WO | 2016077154 A1 | 5/2016 |
| WO | 2017078757 A1 | 5/2017 |
| WO | 2017112910 A1 | 6/2017 |

OTHER PUBLICATIONS

International Search Report issued for PCT/US2018/065278 dated Feb. 28, 2019 (2 pages).
Written Opinion issued for PCT/US2018/065278 dated Feb. 28, 2019 (5 pages).
Cuculich, Phillip S. et al., The Elecrophysiological Cardiac Ventricular Substrate in Patients After Myocardial Infarction, Journal of The American College of Cardiology, Jul. 12, 2011, pp. 1893-1902, vol. 58, No. 18, Elsevier, New York, NY.
European Search Report regarding European Patent Application 18887472.1 dated Jul. 30, 2021, pp. 12.
Loo Jr., Billy W., Sterotactic Ablative Radiotherapy for the Treatment of Refractory Cardiac Ventricular Arrhythmia, Circulation: Arrhythmia and Electrophysiology, vol. 8,3 (2015) pp. 748-750.
Wang, Lei et al., Stereotactic Arrhythmia Radioablation (STAR) of Ventricular Tachycardia: A Treatment Planning Study, Cureus, Jul. 15, 2016, vol. 8, No. 7, pp. 1-8.
Blanck, Oliver et al., Treatment Planning Considerations For Robotic Guided Cardiac Radiosurgery for Atrial Fibrillation, Cureus, Jul. 20, 2016, vol. 8, No. 7, pp. 1-16.
Shah, Ashok J. et al., Body Surface Electrocardiogramapping For Non-invasive Identification of Arrhythmic Sources, Arrhythmia & Electrophysiology Review, 2013, pp. 16-21.

* cited by examiner

Left Ventricular Segmentation 1. basal anterior
2. basal anteroseptal
3. basal inferoseptal
4. basal inferior
5. basal inferolateral
6. basal anterolateral 7. mid anterior
8. mid anteroseptal
9. mid inferoseptal
10. mid inferior
11. mid inferolateral
12. mid anterolateral 13. apical anterior
14. apical septal
15. apical inferior
16. apical lateral
17. apex Scar pattern: NONISCHEMIC
Scar burden: 55cc; 18% OF LV MYOCARDIUM
Suggested ablation location: 1,2,6,7
Suggested volume to achieve full-thickness ablation: 51cc; 15% of LV MYOCARDIUM
Confidence score: 8 of 10 (HIGH)
At-risk structures: MV, AV, LAD, LCX
Recommendations: YEARLY EVAL OF CORONARY ARTERIES, VALVE FUNCTION
CONSIDER PET IMAGING FOR SARCOID
Expected success with SBRT: 80%
Expected success with Catheter RF: 45%
Expected success with Amiodarone: 20%

FIG. 6A

Scar pattern: ISCHEMIC
Scar burden: 98cc; 48% OF LV MYOCARDIUM
HIGH VOLUME WARNING
PRIORITIZED ablation location: 17,15,14,16
Suggested volume to achieve full-thickness
ablation: 50cc; 22% of LV MYOCARDIUM
(MAX 50cc VOLUME)
Confidence score: 5 of 10 (MODERATE,
REDUCED FOR LARGE SCAR SIZE)
At-risk structures: STOMACH, CHEST WALL
Recommendations: BID PPI FOR ONE MONTH
Expected success with SBRT: 70%
Expected success with Catheter RF: 40%
Expected success with Amiodarone: 10%

FIG. 6B

```
Scar pattern: ISCHEMIC
Scar burden: 42cc; 25% OF LV MYOCARDIUM

Suggested ablation location: SEGMENTS 15, 17

Suggested volume to achieve full-thickness
ablation: 36cc; 15% of LV MYOCARDIUM
Confidence score: 7 of 10 (MODERATE)
At-risk structures: DIAPHRAGM; STOMACH
Recommendations: BID PPI FOR 1 MONTH
CONSIDER ECGI TO IMPROVE ACCURACY Expected success with SBRT: 85%
Expected success with Catheter RF: 65%
Expected success with Amiodarone: 50%
```

FIG. 6C

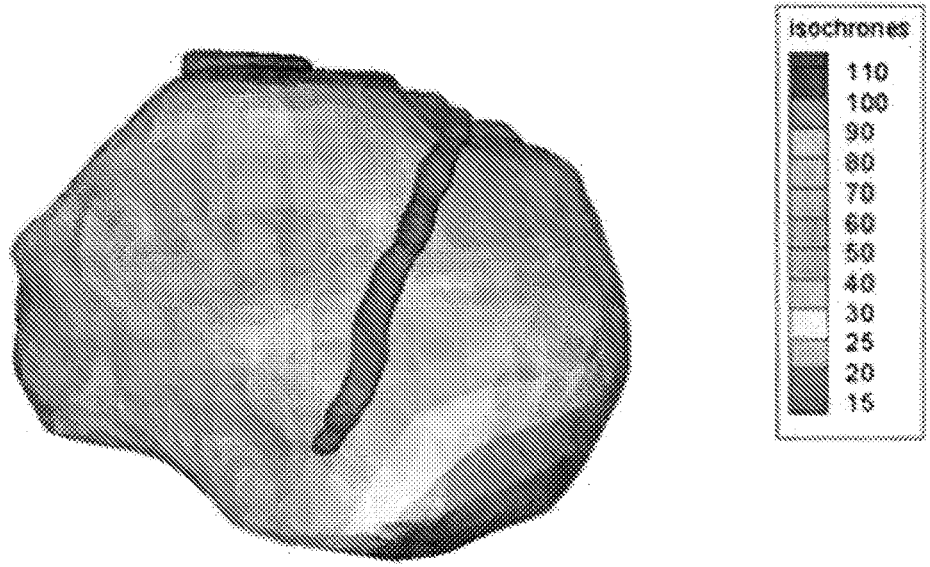
FIG. 18A
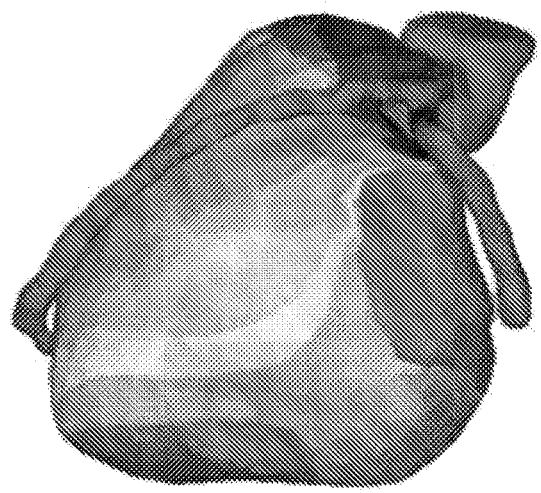 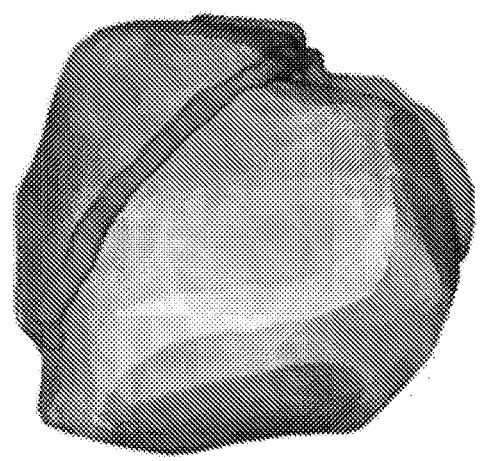
FIG. 18B　　　　　　　　　FIG. 18C

Target Probability

Target Probability

SYSTEM AND METHOD FOR DETERMINING SEGMENTS FOR ABLATION

CROSS REFERENCE TO RELATED APPLICATIONS

This application is the § 371 national stage of International Application No. PCT/US2018/065278, filed Dec. 12, 2018, which claims the benefit of U.S. Provisional Patent Application No. 62/598,162, filed on Dec. 13, 2017 and U.S. Provisional Patent Application No. 62/607,084, filed on Dec. 18, 2017, which are herein incorporated by reference in their entirety.

TECHNICAL FIELD

The present technology pertains to determining a cardiac arrhythmia target for ablation and more specifically to multimodal image mappings and risk profiles for determining atrial or ventricle segments for ablation.

BACKGROUND

Sudden cardiac arrest (SCA) is the single largest cause of death in the developed world. A majority of SCA is due to cardiac arrhythmias, namely ventricular tachycardia (VT) or atrial fibrillation (AF). Current invasive visualization techniques are used to direct the application of the arrhythmia treatment, such as cardiac catheterization. The invasive processes can come with significant risk to the patient. Current treatments for arrhythmias include invasive catheter ablation. Noninvasive ablation using stereotactic body radiotherapy has recently been developed for the treatment of a cardiac arrhythmia. For invasive and non-invasive ablation, imaging and clinical data is manually converted into a target for treatment by a clinician, which results in user dependent variability in treatment. Furthermore, the type of ablation used as well as target selection (e.g., size, location) are determined on an ad hoc basis without the benefit of formal decision support.

Therefore, there is a need for improved identification of a cardiac arrhythmia target volume and treatment plan for noninvasive and invasive arrhythmia ablation and improved decision support for the selection of therapy for arrhythmia ablation. Non-invasive processes for mapping and treating arrhythmias in a patient is realized.

BRIEF SUMMARY

Provided herein is a method for determining one or more cardiac arrhythmia targets for ablation. The method may include receiving one or more mappings selected from an electrical mapping, an anatomic mapping, a functional mapping, and combinations thereof; identifying an abnormality in the one or more mappings; combining the one or more mappings; and defining the one or more cardiac arrhythmia targets based on an overlap of the identified abnormality in the combined one or more mappings. In an aspect, the electrical mapping may be an electrocardiograph image, the anatomic mapping may be at least one of a computer tomography image or a magnetic resonance image, and the functional mapping may be at least one of a photo emission computed tomographic image, a positron emission tomography image or an echocardiogram image. In some aspects, the abnormality may be identified as one or more segments on the one or more mappings, one or more contours on the one or more mappings, or combinations thereof. The abnormality may be identified manually, automatically, or combinations thereof. In an aspect, the method may further include adjusting the one or more cardiac arrhythmia targets based on additional data. The additional data may be selected from a weight of the received mappings, a confidence score, risk, clinical data, demo data, prior knowledge of a specific patient, prior knowledge of previous patients, toxicity, efficacy, quality of data, importance of data, reproducibility of data, physiology of heart, scar size, number of VT's, type of cardiomyopathy, transmurality, location of abnormality, age, gender, size of heart, ejection fraction, thickness of heart, medications, co-morbidity, or combinations thereof. In some aspects, the method may further include ablating the one or more cardiac arrhythmia targets. Ablating the at least one cardiac arrhythmia target may be non-invasive, such as with SBRT. In some aspects, the method may further include weighting the received mappings. In additional aspects, the method may further include determining a confidence score.

In some aspects, the method may further include generating a decision support module. The decision support module may include an output of the one or more cardiac arrhythmia targets and one or more of a description of a scar pattern, a description of a scar burden size and location, a suggested volume to achieve ablation, a confidence score of the combined mappings, a listing of at-risk structures, a general recommendation, an expected success rate with non-invasive therapy, or an expected success rate with alternative treatment modalities.

Further provided herein is at least one non-transitory computer readable medium storing instructions which when executed by at least one processor, cause the at least one processor to: receive one or more mappings selected from an electrical mapping, an anatomic mapping, a functional mapping, and combinations thereof; combine the one or more mappings; and determine, based on the combination of the one or more mappings, one or more cardiac arrhythmia targets for ablation. The at least one processor may further adjust the one or more cardiac arrhythmia targets for ablation. The at least one processor may further weight the received mappings. In an aspect, the at least one processor may determine a confidence score. The electrical mapping may be an electrocardiograph image, the anatomic mapping may be at least one of a computer tomography image or a magnetic resonance image, and the functional mapping may be at least one of a photo emission computed tomographic image, a positron emission tomography image or an echocardiogram image. In another aspect, the at least one processor may: receive one or more clinical mappings including at least one of demographics, surgical history, information about ventricular tachycardia and prior electro-anatomical mappings; supplement the combined one or more mappings with the one or more clinical mappings; and determine, based on the supplemented combined mapping, one or more updated ablations of the one or more cardiac arrhythmia targets for ablation.

In some aspects, the at least one processor may further generate a decision support module. The decision support module may include an output of the one or more cardiac arrhythmia targets and one or more of a description of a scar pattern, a description of a scar burden size and location, a suggested volume to achieve ablation, a confidence score of the combined mappings, a listing of at-risk structures, a general recommendation, an expected success rate with non-invasive therapy, or an expected success rate with alternative treatment modalities.

Additional aspects and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which:

FIG. 6A illustrates an example decision support tool output.

FIG. 6B illustrates an example decision support tool output.

FIG. 6C illustrates an example decision support tool output.

FIGS. 18A, 18B, and 18C show ECGI mapping of a patient in Example 3.

DETAILED DESCRIPTION

Figure 1A:
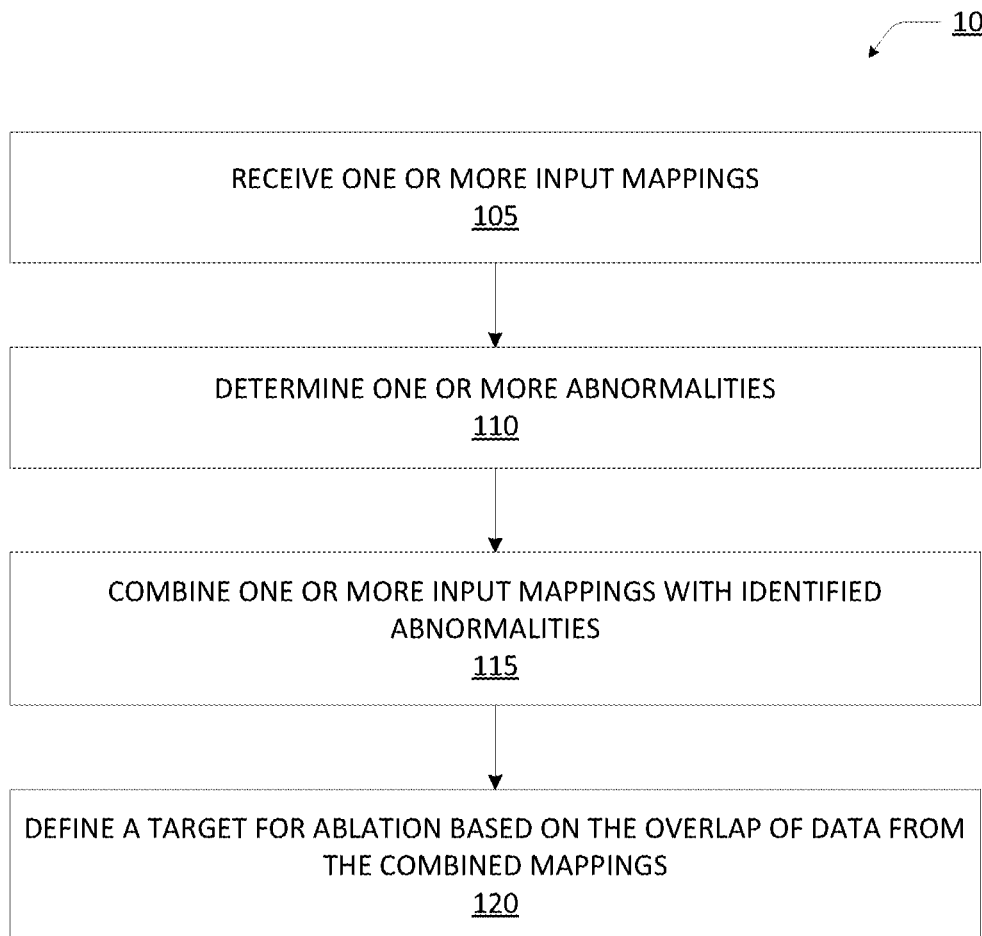
FIG. 1A illustrates a flow diagram of an example method of 100.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and, such references mean at least one of the embodiments.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

As used herein, "magnetic resonance imaging" (MRI) refers to the use of use magnetic fields and radio waves to form images of the body. Typically, when used in cardiac situations, cardiovascular magnetic resonance imaging (CMR) involves ECG gating which combats the artifacts created by the beating of the heart.

As used herein, "computed tomography" (CT) means the use of x-ray images taken from the patient at different angles to produce tomographic (cross-sectional) images.

Reference to "electrocardiographic imaging" (ECGI) means a technique which reconstructs epicardial potentials, electrograms, and activation sequences (isochrones) from electrocardiographic body-surface potentials noninvasively. In brief, the patient undergoes a CT or MRI scan while wearing a vest of electrodes that record electrical activity. The major electrical activity signal is from cardiac electrical activity. The electrical information from the surface of the body can then be registered to a patient-specific heart model derived from CT or MRI images to display the characteristics of the cardiac electrical activity mapped onto a patient's anatomy. Useful information includes: where the heart beat begins, the depolarization sequence of the heart tissue, and which parts of the heart have abnormal depolarization behavior. Fitting the vest of electrodes on the patient, obtaining electrical data, and performing the CT scan is generally completed in under 30 minutes.

Reference to "stereotactic body radiotherapy" (SBRT), also known as stereotactic ablative radiotherapy (SABR) or stereotactic radiosurgery (SRS), means the precise delivery of high doses of radiation to targets in the body over few (typically, <5) fractions with minimal exposure of normal adjacent tissue.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

The approaches set forth herein can be used to implement systems and methods of the identification of a cardiac arrhythmia target utilizing multi-modal imaging techniques.

Underlying cardiomyopathies and scarring most often cause ventricular arrhythmias. The scar from the cardiomyopathy (e.g., previous heart attack) forms the substrate for abnormal electrical circuits within the heart, which causes VT. Based on symptoms, severity, and cause of the arrhythmia, treatment options include, but are not limited to, antiarrhythmic drugs, placement of a pacemaker/defibrillator, surgical ablation, catheter-based ablation (endocardial, epicardial) using radiofrequency energy to create thermal injury, non-invasive ablation with SBRT, and/or a combination thereof.

Invasive catheter ablation is largely effective in the absence of ventricular scar (idiopathic ventricular tachycardia). However, catheter ablation for cardiomyopathic ventricular tachycardia is associated with recurrence rates as high as 50% at 6 months.

In electrophysiology (EP)-guided Noninvasive Cardiac Radioablation (ENCORE), patients undergo pre-treatment targeting by using available cardiac imaging and electrophysiological data and visually co-registering with information provided by noninvasive ECGI during induced VT. For example, in an ENCORE-VT workflow, multi-modality imaging may be combined with scar imaging and electrical mapping offline to define a target for ablation by SBRT. A plan is then developed in the radiation therapy treatment planning system (TPS). On the day of treatment, the patient is immobilized to prevent patient motion, the treatment unit is aligned with the patient, and treatment is delivered with a linear accelerator.

Currently, the data is manually converted into a target on the SBRT planning CT by the electrophysiologist and radiation oncologist through a time-consuming and imprecise iterative review of the targeting data offline from the TPS.

Current identification of the arrhythmic component of a ventricular scar in ENCORE is crude, using visual estimations off-line between various imaging modalities to manually create a target volume for ablation. Such visual estimations are highly user dependent and require significant consistency and skill by individual physicians. As such, there is potential for variability in outcomes merely due to inconsistencies and experience of practitioners.

The disclosed technology addresses the need in the art for automatic identification of one or more cardiac arrhythmias in a patient and an objective treatment plan that is user independent. Disclosed are systems, methods, and computer-readable storage media for implementing a multi-modal technique for the identification of one or more arrhythmic components of a ventricular tachycardia and generating a treatment plan.

The methods disclosed herein define a radiation therapy target (treatment region) from multi-modality imaging, where some or all of the modalities are used to define individual regions of interest, and then may be combined in a weighted fashion to generate the final target volume.

Any modality for imaging an arrhythmia can be used in conjunction with one or more other modalities for imaging an arrhythmia as the data acquired can be complementary and nonduplicative. In some examples, the imaging can include electrophysiological signatures and/or anatomical signatures. The imaging modality may be noninvasive. Noninvasive imaging modalities may include, but are not limited to CT, MRI, PET, SPECT, ECGI, and 12-lead EKG. However, multi-modality anatomic (CT, MRI), functional (PET, SPECT), and electrophysiologic (ECGI) images exist in a variety of file formats and are often presented in ways that make it technically and visually challenging to integrate all of the information together in one environment. Therefore, the images or mappings from the various sources can be converted to a compatible format for combination or comparison. In one example, two or more sets of images or mappings can be aligned with each other. Accordingly, noninvasive systems for imaging may be used in combination to inform noninvasive treatment of a cardiac arrhythmia in a subject.

Abnormalities, or regions of interest, on each image mapping may be manually or automatically defined. In at least one example, expert-defined targets can be used to train a model, such as a neural network, with inputs being information from the multimodality images or the images themselves. The model can then be used on a new set of multi-modality images to identify the abnormality or infer the target volume where one is unknown.

A 17 segment model can be used to define anatomical subregions of the ventricle. The segmentation model may simplify the problem from labeling thousands of individual voxels to labeling only 17 regions. Moreover, the segmentation model overcomes the challenge of needing to co-register the individual multi-modality images to each other.

The combined noninvasive mappings or segmentation models can then provide for a consistent, objective determination of the target for treatment. Consistency of target delineation at the outset is critical, so that identification of the "correct" or "optimal" target in the future as assessed by patient outcomes is not confounded by heterogeneity across physicians in targeting.

In an example, methods for defining at least one cardiac arrhythmia target can include scoring each mapping individually for VT presence. In another example methods for defining at least one cardiac arrhythmia target can include directly inferring the target probability.

Semi-automatic or automatic therapy selection based on patient and target attributes can provide uniformity of treatment selection and allow for more robust assessment of outcomes. In various aspects, the procedure recommendation may include, but is not limited to noninvasive ablation, invasive ablation, or combinations thereof. In an aspect, noninvasive ablation methods can include, but are not limited to stereotactic body radiotherapy, stereotactic ablative radiotherapy, stereotactic radiosurgery, fractionated radiotherapy, hypofractionated radiotherapy, high-frequency/focused ultrasound, or lasers.

Radiation can be administered with either x-rays/photons (typically with a linear accelerator), γ-rays (such as with a Co-60 unit), or charged particles (for example, protons, carbon, helium, etc.). A variety of delivery systems exist, all of which have various delivery methods. In one example, noninvasive treatment may include ablation with SBRT. The radiotherapy delivery may require optimizing immobilization, assessment and accounting of motion in treatment planning and delivery, the ability to create and deliver compact precise dose distributions to maximize dose to the target while minimizing dose to healthy tissues, and image-guidance. The radiotherapy delivery may include defining patient-specific motion trajectories of the heart using independent measurements of respiratory and cardiac motion for both accurate delivery of treatment and reducing the size of target volumes in order to mitigate toxicities associated with off-target radiation to normal tissues.

I. Target Identification

Figure 1B:
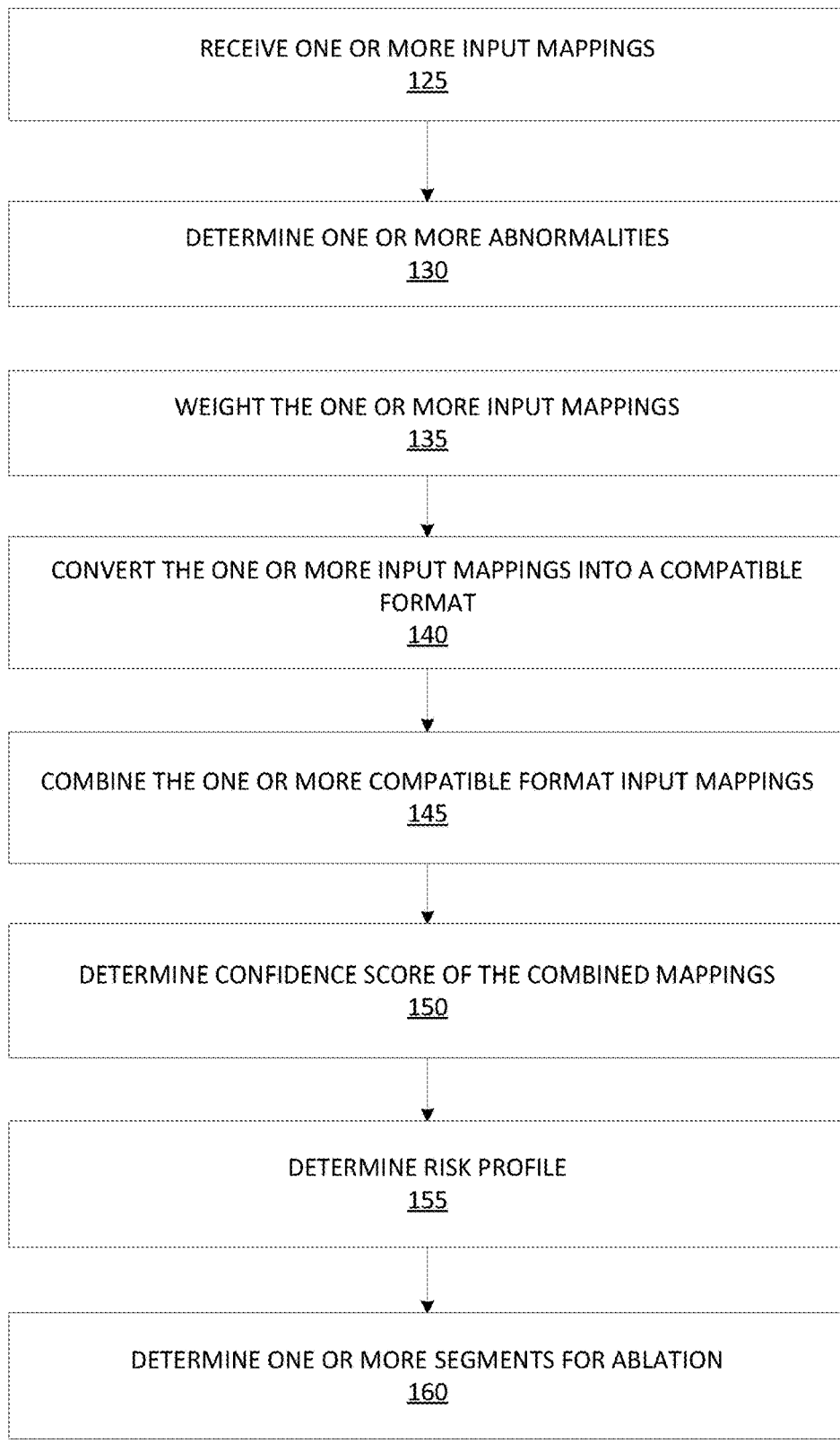
FIG. 1B illustrates a flow diagram of an example method of 101.

A description of a method for defining a cardiac arrhythmia target for ablation, as illustrated in FIG. 1A, is first disclosed herein. A discussion of an alternative embodiment thereof as illustrated in FIG. 1B will then follow. These variations shall be described herein as the various embodiments are set forth. The disclosure now turns to FIG. 1A.

The method shown in FIG. 1A is provided by way of example, as there are a variety of ways to carry out the method. Additionally, while the example method is illustrated with a particular order of blocks, those of ordinary skill in the art will appreciate that FIG. 1A and the blocks shown therein can be executed in any order that accomplishes the technical advantages of the present disclosure and can include fewer or more blocks than illustrated. Each block shown in FIG. 1A represents one or more processes, methods or subroutines, carried out in the example method.

FIG. 1A shows a flow diagram of an example method 100 for identification of a cardiac arrhythmia target. In non-limiting examples, the cardiac arrhythmia target can be ventricle arrhythmic segments, ventricle contours, atrial segments, and/or atrial contours. In some examples, method 100 can be performed in real-time at an image planning system. In other examples, method 100 can be performed in planning for future use in an image planning system.

Method 100 can begin a block 105. At block 105, at least one processor can receive one or more input mappings (e.g., of a corresponding ventricle, a corresponding atria, etc.). In some examples, the one or more input mappings can be historical input mappings previously taken and/or newly required input mappings. In some examples, the one or more input mappings can be one or more images from a singular patient. For example, the one or more input mappings can be one or more electrophysiologic mappings, anatomic mappings (e.g., fibrosis), functional mappings (e.g., perfusion, motion, etc.), computer simulation mappings (e.g., electrical and/or mechanical whole heart models), clinical mappings, etc. In some examples, the electrophysiologic mappings can be, but are not limited to: EKG, 12-lead ECG of VT (e.g., exit site of VT/PVC, etc.), 12-lead ECG of sinus rhythm (SR) (e.g., Q waves for prior infarct, comparison for PVC localization, etc.), ECGI of VT (e.g., exit site of VT, reentrant propagation, diastolic potentials, etc.) and/or ECGI of SR (e.g., zone of slow conduction/block, late potentials, etc.). In some examples, the anatomic mappings can be, but are not limited to: CT scans (e.g., myocardial thinning (% wall thickness), calcification, etc.) and/or MRI scans including, but not limited to gadolinium and/or pixel intensity map (e.g., location of fibrosis (which segment; endo, midmyocardial, epi), thickness of fibrosis (% wall thickness), volume of fibrosis, heterogeneity of fibrosis, etc.). In some examples, the functional mapping can be, but are not limited to: SPECT scan (e.g., viability, infarction/ischemia, etc.), PET scan (e.g., metabolism, inflammation, etc.), MRI scan (e.g., abnormal wall motion, etc.), Echo (e.g., abnormal wall motion, etc.), and/or cardiac and pulmonary motion data (e.g., motion-sensitive sequences such as 4D-CT and 4D-MRI to construct anticipated motion envelopes for optimal targeting and delivery). In some examples, the clinical mapping can be, but are not limited to: demographics (e.g., age, gender, NYHA, CKD, lungs, PVD, Charlson vs. Seattle HF model, etc.), surgical history (e.g., cardiac surgery, etc.), knowledge about clinical VT (e.g., MMVT or multiple VTs) and/or prior electroanatomical mapping/ablations. In some examples, the clinical mappings are optional. In some examples, the clinical mappings are used as supplemental information (e.g., during risk profiling). In some examples, the electroanatomical mapping can be separately displayed from a created image mapping (e.g., an output from method 100) for comparison purposes (e.g., the electroanatomical mapping would not be used for segment determination). In some examples, the computer simulation mappings can include in silico models.

At block 110, the method 100 can define or identify one or more abnormalities in the one or more input mappings. The abnormalities can be identified, for example, in an MRI by the scar location, an abnormality in PET/SPECT may be regions that are not viable, an abnormality in an electrical mapping may be where a VT originates, etc. In various examples, the abnormality can be defined by selecting the abnormality on each mapping, manually or automatically segmenting the mapping and manually selecting the abnormality, automatically contouring the mapping and manually selecting the abnormality, automatically contouring the mapping and automatically selecting the abnormality, or combinations thereof. In some examples, the identification of the abnormalities can be used in training a neural network, for example, by using supervised or reinforcement learning. For example, a physician can locate abnormalities in different image types. The abnormalities along with the image and metadata of the image can be used to teach the neural network how to automatically (or autonomous) locate abnormalities.

Defining or identifying one or more abnormalities in the one or more input mappings can include segmenting one or more of the input mappings. In some examples, the one or more of the input mappings can be segmented using a segmentation model. The at least one processor can determine one or more abnormality in one or more cardiac arrhythmia target segments. In various examples, the input mapping can be divided into at least 2 segments, at least 4 segments, at least 6 segments, at least 8 segments, at least 10 segments, at least 12 segments, at least 14 segments, at least 16 segments, at least 18 segments, or at least 20 segments. In one example, an input mapping (e.g. a 17-lead ECG) can be divided into 17 segments. The segments can be the same or similar size, different sizes, or combinations thereof. After an input mapping has been segmented, the segments that include the abnormality can be determined.

In some examples, a 3D model of the 17 segments can be generated. In various examples, the model can be generated for the left ventricle, right ventricle, and/or atria. An elliptical cone can be used to generate the 3D model, but any arbitrary ventricle-like or atria-like shape may be used. In at least one example, for each input mapping, the 3D model can be overlaid on the mapping using deformable registration of the model to a left ventricle contour. In some examples, a free form (b-spline) registration can be used for alignment. Since the segment model is symmetric, anatomical landmarks such as the apex, anterior interventicular groove, posterior interventicular groove, and mitral valve plane can be identified and used as anchor points to align the correct segments in the model to the correct anatomical locations. In some examples, the 3D model can be located on the epicardial surface, and extend volumetrically to the endocardial surface.

Defining or identifying one or more abnormalities in the one or more input mappings can include contouring one or more of the input mappings. In various examples, a contour on one or more input mappings can be identified. The input mapping may be a 3D input mapping. For example, the user or physician may physically draw a contour on the 3D input mapping or the processor may identify the contour on the 3D input mapping which includes the abnormality. The abnormality can be automatically defined in the input mappings. In some examples, more than one abnormality can be identified. For example, the abnormality defined in the input mappings can be a single VT, multiple VTs, a single VT exit, and/or multiple VT exits.

In one example, the abnormality can be manually identified on a first input mapping using a segmentation model and manually contoured on another input mapping, such as ECGI, MRI, CT, and/or PET. In another example, the abnormality can be manually identified on a first input mapping using a segmentation model and automatically contoured on another input mapping, such as ECGI, MRI, CT, and/or PET. In yet another example, the abnormality can be manually defined on a 12-lead ECG using a segmentation model and can be manually identified on an ECGI, MRI, CT, and/or PET mapping. In one example, the abnormality can be automatically defined on a 12-lead ECG and can be manually identified on an ECGI, MRI, CT, and/or PET mapping. In some examples, each input mapping can be reviewed by an expert individually, and a likelihood of each segment contributing to VT can be scored. These scores can be stored in a database. A target probability defined for each segment s as the weighted average (by weight w) over all input mappings i for each patient p can then be generated and stored in the database.

In yet another example, the abnormality can be automatically defined on all input mappings. In one example, the abnormality can be automatically defined on one or more input mappings by machine learning. For each input mapping, the image content within each segment can be extracted. As each segment can be a conical section, it can be unrolled into a rectilinear, 3D image volume. This process can generate $N_{s,p,i}$ segments, where s is the number of segments per image (for example, up to 17, but could be any number), i is the number of input mappings per patient, and p is the number of patients in the database. Each segment can be labeled as VT, no VT, and unevaluable. Unevaluable segments can be ignored in the modeling for a two class modeling problem. A weighting parameter w from the set of numbers between 0 and 1 can also be assigned by the expert to denote confidence for each segment.

Any modeling approach can be used to learn the image features that predict the location of an abnormality (e.g., VT) on each input mapping. For example, a deep convolutional neural network can be used. Because the model only includes two classes (VT/no VT), a deep network may not be needed. For example, a model can use approximately 5 layer blocks, including convolutional blocks, convolutional layers, and fully connected layers. In some examples, the network can be trained to predict VT/no VT using training data. In some examples, preprocessing, including whitening and normalization, may be used. In other examples, the model can be performed on new input mappings. Segments can then be extracted and an inference can be performed using the network above. In an example, a VT/no VT label can then be produced for each segment of each new input mapping.

In some examples, a probability for each abnormality (target probability) can be learned by adding additional layers on the neural network. These may be fully connected layers which seek to learn the values of the weights w indirectly. The labeled data can be the actual target probabilities. In an example, the neural network can include additional layers which combine the individual segment classes into a weighted average, and seek to learn the weighting algorithm indirectly.

In other examples, a target probability defined for each segment s as the weighted average (by weight w) over all images i for each patient p can first be generated. The individual segment images can be normalized first and then concatenated into a 4D depth image of depth i, and training can commence on these depth images to predict the continuous target probability. In various examples, the continuous target probability can range from 0 to 1.

At block 115, the method 100 can combine one or more input mappings with identified abnormalities. For example, the input mappings can be combined by overlapping segmentation models, combining a segmentation model and 3D geometries, or combinations thereof. In some example, the overlap of contours from the identified abnormality in a 3D geometry can be selected. In another example, an input mapping with a segmentation model and a contour of at least one 3D input mapping can be combined. For example, a segmentation model from a 12-lead ECG can be co-registered with the identified contours from a 3D geometry (e.g., ECGI, MRI, CT, PET).

At block 120, the method 100 can define the target for ablation based on the overlap of data from the combined mappings. The cardiac arrhythmia target can be a segment, multiple segments, or a 3D volume. In the segmentation model, the cardiac arrhythmia target can be defined by identifying segments with the most overlap or area of highest intensity. For 3D contours, the cardiac arrhythmia target can be defined by identifying overlap of contours in the 3D geometry. A 3D anatomy defined target (manual or automatic) can be a smaller area and more patient specific than a segment. In other examples, a segmentation model can be co-registered with at least one 3D contour, such that an overlap between a segment and a contour can identify a target. In some examples, the multiple independently defined targets for ablation or prioritized targets for ablation can be identified by looking at overlap for separate VTs (for each VT/VT exit sites that is mapped).

In some examples, the one or more segments can be determined for ablation using one or more type of ablative energy techniques (e.g., SBRT, photon, carbon ions, protons, helium, ultrasound, etc.). In some examples, the one or more segments can be determined for a noninvasive arrhythmia guidance system. For noninvasive stereotactic cardiac ablation, the method can integrate with, transfer data to, or exist within a radiotherapy treatment planning system or a decision support module. In other examples, the one or more segments can be determined for invasive ablation. For invasive catheter ablation, the method can integrate with, transfer data to, or exist within a catheter ablation system.

The at least one processor can determine one or more targets for ablation, for example, the target for ablation may include one or more cardiac arrhythmia target segments. In various examples, the target for ablation may include at least 1 segment, at least 2 segments, at least 4 segments, at least 6 segments, at least 8 segments, at least 10 segments, at least 12 segments, at least 14 segments, at least 16 segments, at least 18 segments, or at least 20 segments. The segments can be the same or similar size, different sizes, or combinations thereof. For example, the target for ablation can be determined and formatted in an image mapping (e.g., an image mapping for input into treatment planning system). In some examples, the target for ablation can be determined based on the overlapping segments from the input mappings and the risk profile. In some examples, the overlapping of segments from the input mappings can include an initial list of segments for ablation. The initial list can then be run through the risk profile to determine potential risk of ablation of the segments from the initial list. Based on the risk profile, the one or more segments for ablation can be determined.

Figure 3A:
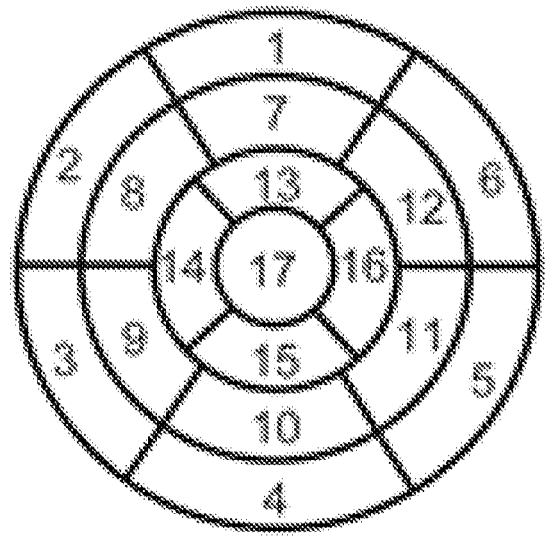
FIGS. 3A, 3B, and 3C illustrate example cross-sections of ventricle segments.
Figure 3C:
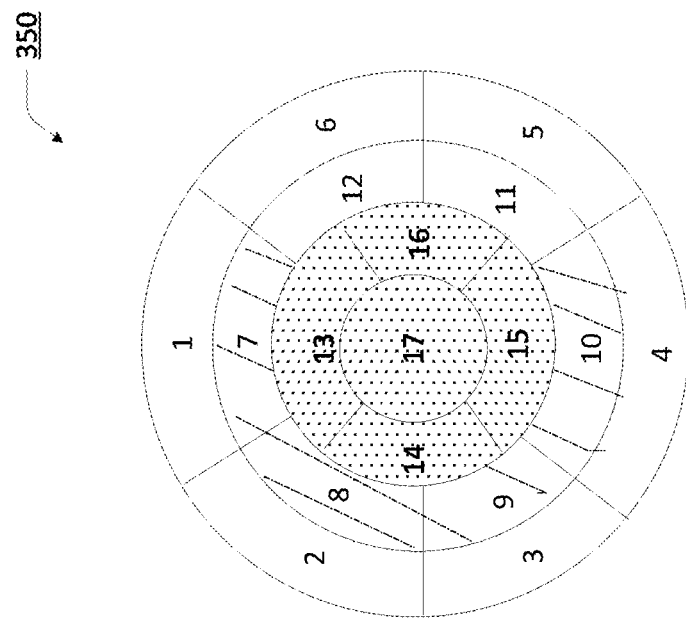
Figure 3B:
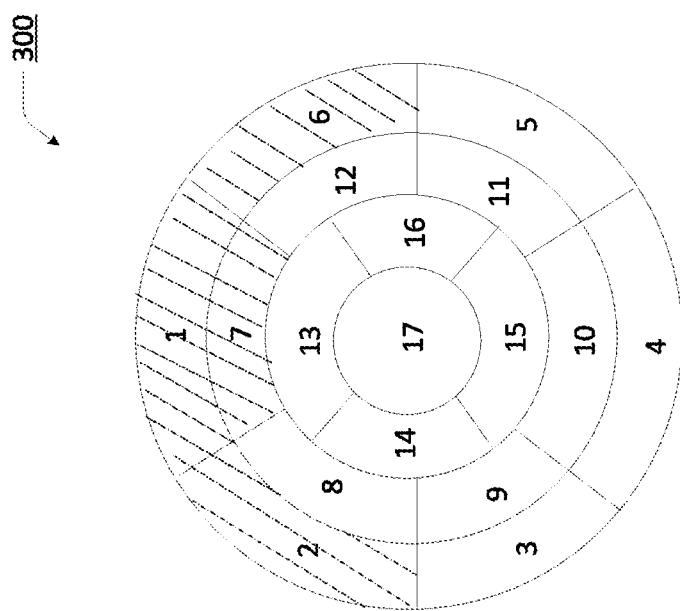

In one example, one or more segments for ablation are illustrated in FIGS. 3A, 3B, and 3C. FIGS. 3A, 3B, and 3C illustrate cross-sections of a ventricular segmentation. For example, the ventricle can be segmented into seventeen different segments—1. basal anterior; 2. basal anteroseptal; 3. basal inferoseptal; 4. basal inferior; 5. basal inferolateral; 6. basal anterolateral, 7. mid anterior; 8. mid anteroseptal; 9. mid inferoseptal; 10. mid inferior; 11. mid inferolateral; 12. mid anterolateral; 13. apical anterior; 14. apical septal; 15. apical inferior; 16. apical lateral; and 17. apex.

FIG. 3B further illustrates one or more segments for ablation based on output from method 100. For example, segments: 1. Basal anterior; 2. Basal anteroseptal; 6. Basal anterolateral; and 7 mid anterior have been determined as segments designated for ablation. In an example, the above segments have been identified for a 61-year-old man with nonischemic cardiomyopathy, NYHA class 4 heart failure symptoms, (LVEF 37%; LVEDD 6.1 cm) with repeated ICD shocks for VT despite treatment with amiodarone and mexiletine. Previous to those medications, the patient failed sotalol. ICD interrogation showed at least two different VT cycle lengths. Previous endocardial ablation one year before SBRT targeted four distinct VT circuits in the basal anterior septum and anterolateral left ventricle.

In the example of FIG. 3B, the corresponding input mappings can be: electrical mapping of two VTs—ECG (2, 6), ECGI (1, 6); anatomic mappings of MRI (1, 2, 6, 7) and CT (no thinning) and functional mappings of Echo (global HK). Each mapping can identify one or more segments for potential ablation. When these mappings are combined, the segments of 1, 2, 6 and 7 are recommended for ablation. The decision support module output for this example is shown in FIG. 6A.

FIG. 3C further illustrates one or more segments for ablation based on output from method 200. For example, segments: 13. apical anterior, 14. apical septal, 15. apical inferior, 16. apical lateral and 17. apex have been determined as high priority segments designated for ablation and segments: 7. mid anterior, 8. mid anteroseptal, 9. mid inferoseptal, and 10. mid inferior have been determined medium priority segments designated for ablation. In an example, a 75-year-old man with ischemic cardiomyopathy, NYHA class 4 heart failure symptoms, (LVEF 20%; LVEDD 6.9 cm) with repeated ICD shocks for VT despite treatment with amiodarone and mexiletine (intolerant to both presently). Advanced CKD precluded sotalol. ICD interrogation showed largely one VT cycle length. No previous endocardial ablation (high-risk for complication).

In the example of FIG. 3C, the corresponding input mappings can be electrical mapping of ECG (14, 15, 16, 17), ECGI (SR LOP 15, 16, 17), ECGI (VT 15, 17); anatomic mapping of MRI (7, 8, 9, 10, 13, 14, 16, 17), CT (7, 8, 9, 13, 14, 15, 16, 17); and functional mapping of PET (7, 8, 9, 13, 14, 15, 17), MRI (2, 3, 4, 7, 8, 9, 10, 13, 14, 15, 17). Each mapping can identify one or more segments for potential ablation. When these mappings are combined, the segments of 13-17 can be a high priority recommendation for ablation and the segments of 7-10 can be medium priority recommendation for ablation. The decision support module output for this example is shown in FIG. 6B.

In some examples, the cardiac arrhythmia target for ablation can be adjusted. For example, cardiac arrhythmia target can be adjusted based on various parameters including, but not limited to, risk, clinical data, demo data, prior knowledge of a specific patient, prior knowledge of previous patients, toxicity, efficacy, quality of data, importance of data, reproducibility of data, physiology of heart, scar size, number of VT's, type of cardiomyopathy (e.g., ischemic or non-ischemic), transmurality (e.g., thick or thin scar), location of abnormality (e.g., certain segments may be more or less successful), age, gender, size of heart, ejection fraction, thickness of heart (e.g., weak or healthy heart), medications (e.g., anti-arrhythmic medication), co-morbidity, and combinations thereof. In various examples, the adjustment of the target may be done manually or automatically. As additional patients are treated, the previous treatments can inform future treatments and can be used to adjust the target of the current patient (for example, by training the neural network). In another example, the target may be adjusted based on a weighting of input mappings or the confidence score of the combined mappings.

In some examples, the prior knowledge of previous patients can come from the medical literature and/or data inputted into the database from individual patients. In various examples, the data can be inputted into the database manually from providers, researchers, etc., automatically from discrete data capture of natural language processing (NLP) from electronic medical records (EMR), or automatically from devices with the patient. Non-limiting examples of patient devices that can automatically into data into the database include an ICD, phone, or wearable devices. In an example, the ICD can be enrolled in a reporting program to facilitate automatic input to the database. In another example, the patient's phone can include an application to capture patient reported outcomes. In yet another example, a wearable device can include a smart watch, heart rate monitor, or an activity tracker capable of transmitting any captured data to the database.

In some examples, the determined segments can be assigned priorities and/or probabilities. For example, based on the combination of input mappings and risk profile the determined segments could be assigned high, medium or low priorities. In some examples, all of the cardiac arrhythmia target segments can be assigned a priority (e.g., high, medium or low). In other examples, segments assigned a high priority and medium prior are provided in the determination.

In some examples, the determined segments can be provided on an image mapping for use in the ablation procedure. The image mapping can integrate with invasive and noninvasive delivery platforms. For example, the image mapping can be a volume for use in treatment planning (e.g., in a treatment planning system/software). In some examples, the image mapping can be used as an input to a treatment planning system (e.g., that can carry out the ablation). The image mapping can provide for patient customized treatment planning (e.g., not all patients will require or present with all known multi-modal data).

Weighting of input mappings can happen at any point in the method 100. Weighting of the input mappings may improve the quality or accuracy of the target identification by giving higher weight to input mappings of higher quality, clinical relevance, or importance as compared to the other mappings for the patient. For example, the weighting of input mappings can occur before the mappings are combined, after abnormality identification, after combination, after defining the target, or after adjusting the target. Each input mapping can be given a weight based on one or more factors, for example, quality of scan (e.g., ICD artifact on MRI, etc.), number of input mappings (e.g., number of modalities), clinical relevance (e.g., non-clinical CT induced, etc.), expert acceptance of individual technique, importance of data, or combinations thereof. In some examples, a weight can be given between the input mappings, for example, relative strength between each input mappings findings, agreement between the groups, etc. For example, higher weights can be determined when there is a higher number of input mapping modalities of high quality scans with a high level of overlap between the input mappings. In another example, lower weights can be given when there is a lower number of input mapping modalities of a variety of qualities with a lower level of overlap between the input mappings.

In some examples, a confidence score of the combined input mapping or identified cardiac arrhythmia target can be determined. In an example, the confidence score can be an assessment of the combined input mappings. The confidence score can also incorporate clinical data or any data used to adjust the target. For example, the input mappings weights, the weights between input mappings, agreement of data between the different input mappings, or the amount of overlap of results (e.g., segment of ablation, etc.) can be used to determine a confidence score. For example, the confidence score can be determined to quantify the quality and reproducibility of one or more segments or contours for ablation. In some examples, the confidence score can be increased with higher degrees of overlap between imaging groups (e.g., segments to ablate, etc.). In other examples, the confidence score can be decreased with incomplete input mapping, poor quality of input mapping, increased number of VTs, large scar size (e.g., scar greater than ablation), etc.

The method 100 can further include determining a risk profile. In some examples, the risk profile can be determined from historical input mappings, side-effects, segment volume limit, and/or results from previous recommended segments for ablations. For example, data associated with previous patients undergoing method 100 (or similar methods) and results of any procedures performed using data or mappings obtained through method 100 can be stored for determining the risk profile of a patient. In some examples, the risk profile can be used to determine potential risk or impact to the patient associated with the recommended segments for ablation. In some examples, patient demographic information can be used to determine the risk profile (e.g., age, health, previous surgeries, etc.). In some examples, the historical input mapping, corresponding segment determinations and ablation results (from the determinations) can be used to determine which of the cardiac arrhythmia target segments you can treat without high risk and/or complications and further, which segments are generally high risk and/or have the most compilations. In at least one example, the risk profile is reported to the user/physician for therapy selection or counseling of toxicities.

In one example, the initial target list can include segments 1, 2, 6, 7, 8, 12 and 13. The risk profile can determine based on the history of the current patient and/or the history of similar patients that a segment volume limit should equal four (4). The resulting determined segments for ablation can then be 1, 2, 6 and 7. In another example, the initial list can include segments 1, 2, 6 and 7. The risk profile can determine these segments are higher risk because, for example, the coronary artery is in those segments. The determination of segments can then be made as 1, 2, 6 and 7 with additional planning information for follow-up or monitoring of the coronary artery post-ablation. In another example, the initial list can include segments 1, 2 and 6. The risk profile can determine based on the history of similar patients (e.g., similar histories, procedures, etc.) that had segments 1, 2 and 6 ablated and also benefit from segment 7 being ablated. The resulting segments for ablation can then be 1, 2, 6 and 7. The examples provided herein at examples only and are non-limiting.

In some examples, the determined segments can be provided on an image mapping for use in the ablation procedure. The image mapping can integrate with invasive and noninvasive delivery platforms. For example, the image mapping can be a volume for use in treatment planning (e.g., in a treatment planning system/software). In some examples, the image mapping can be used as an input to a treatment planning system (e.g., that can carry out the ablation). The image mapping can provide for patient customized treatment planning (e.g., not all patients will require or present with all known multi-modal data). In an example, the target segments or 3D contours may be used to identify a planning target volume within treatment planning software. In some examples, the planning target volume and/or the segments/contours can be used to simulate treatment for internal quality assurance.

The method shown in FIG. 1B is provided by way of example, as there are a variety of ways to carry out the method. Additionally, while the example method is illustrated with a particular order of blocks, those of ordinary skill in the art will appreciate that FIG. 1B and the blocks shown therein can be executed in any order that accomplishes the technical advantages of the present disclosure and can include fewer or more blocks than illustrated. Each block shown in FIG. 1B represents one or more processes, methods or subroutines, carried out in the example method.

FIG. 1B shows a flow diagram of an example method 101 for determining one or more segments for ablation. In some examples, the one or more segments for ablation may be a cardiac arrhythmia target. In non-limiting examples, the cardiac arrhythmia target can be ventricle arrhythmic segments or atrial segments. In some examples, method 101 can be performed in real-time at an image planning system. In other examples, method 101 can be performed in planning for future use in an image planning system. Method 101 includes the steps of method 100 and further includes weighting the one or more input mappings at block 135, determining a confidence score of the combined mappings at block 150, and determining a risk profile at block 155.

At block 125, at least one processor can receive one or more input mappings (e.g., of a corresponding ventricle, a corresponding atria, etc.). In some examples, the one or more input mappings can be historical input mappings previously taken and/or newly required input mappings. In some examples, the one or more input mappings can be one or more images from a singular patient. For example, the one or more input mappings can be one or more electrophysiologic mappings, anatomic mappings (e.g., fibrosis), functional mappings (e.g., perfusion, motion, etc.), computer simulation mappings (e.g., electrical and/or mechanical whole heart models), or clinical mappings. In some examples, the electrophysiologic mappings can be, but are not limited to: EKG, 12-lead ECG of VT (e.g., exit site of VT/PVC, etc.), 12-lead ECG of sinus rhythm (SR) (e.g., Q waves for prior infarct, comparison for PVC localization, etc.), ECGI of VT (e.g., exit site of VT, reentrant propagation, diastolic potentials, etc.) and/or ECGI of SR (e.g., zone of slow conduction/block, late potentials, etc.). In some examples, the anatomic mappings can be, but are not limited to: CT scans (e.g., myocardial thinning (% wall thickness), calcification, etc.) and/or MRI scans including, but not limited to gadolinium and/or pixel intensity map (e.g., location of fibrosis (which segment; endo, midmyocardial, epi), thickness of fibrosis (% wall thickness), volume of fibrosis, heterogeneity of fibrosis, etc.). In some examples, the functional mapping can be, but are not limited to: SPECT scan (e.g., viability, infarction/ischemia, etc.), PET scan (e.g., metabolism, inflammation, etc.), MRI scan (e.g., abnormal wall motion, etc.), Echo (e.g., abnormal wall motion, etc.), and/or cardiac and pulmonary motion data (e.g., motion-sensitive sequences such as 4D-CT and 4D-MRI to construct anticipated motion envelopes for optimal targeting and delivery). In some examples, the clinical mapping can be, but are not limited to: demographics (e.g., age, gender, NYHA, CKD, lungs, PVD, Charlson vs. Seattle HF model, etc.), surgical history (e.g., cardiac surgery, etc.), knowledge about clinical VT (e.g., MMVT or multiple VTs) and/or prior electroanatomical mapping/ablations. In some examples, the clinical mappings are optional. In some examples, the clinical mappings are used as supplemental information (e.g., during risk profiling). In some examples, the electroanatomical mapping can be separately displayed from a created image mapping (e.g., an output from method 200) for comparison purposes (e.g., the electroanatomical mapping would not be used for segment determination). In some examples, the computer simulation mappings can include in silico models.

At block 130, the method 101 can define or identify one or more abnormalities in the one or more input mappings. The abnormalities can be identified, for example, in an MRI by the scar location, an abnormality in PET/SPECT may be regions that are not viable, an abnormality in an electrical mapping may be where a VT originates, etc. In various examples, the abnormality can be defined by selecting the abnormality on each mapping, manually or automatically segmenting the mapping and manually selecting the abnormality, automatically contouring the mapping and manually selecting the abnormality, automatically contouring the mapping and automatically selecting the abnormality, or combinations thereof. In some examples, the identification of the abnormalities can be used in training a neural network, for example, by using supervised or reinforcement learning. For example, a physician can locate abnormalities in different image types. The abnormalities along with the image and metadata of the image can be used to teach the neural network how to automatically (or autonomous) locate abnormalities.

At block 135, the input mappings can be weighted. Weighting of input mappings can happen at any point in the method 101. For example, the weighting of input mappings can occur before the mappings are combined, after abnormality identification, after combination, after defining the target, or after adjusting the target. Each input mapping can be given a weight based on one or more factors, for example, quality of scan (e.g., ICD artifact on MRI, etc.), number of input mappings (e.g., number of modalities), clinical relevance (e.g., non-clinical CT induced, etc.), expert acceptance of individual technique, importance of data, etc. In some examples, a weight can be given between the input mappings, for example, relative strength between each input mappings findings, agreement between the groups, etc. For example, higher weights can be determined when there is a higher number of input mapping modalities of high quality scans with a high level of overlap between the input mappings. In another example, lower weights can be given when there is a lower number of input mapping modalities of a variety of qualities with a lower level of overlap between the input mappings.

At block 140, the at least one processor can convert the received input mappings into a compatible format. For example, the input mappings (e.g., CT, MRI, PET, SPECT, ECGI, etc.) can exist in a variety of file formats. The variety of file formats can be converted into a compatible format, for example, to enable correlation of overlapping data points. In some examples, the input mappings can require reorientation of the image. For example, a standard procedure can be implemented for orienting and converting an input mapping based on modality. In some examples, non-image data (e.g., 12-V EKG, ECGI system, etc.) can be integrated with the input mappings. In some examples, the non-image data, such as the 12-lead mappings can be displayed to the user and the user can interact with or click on segments of the cardiac arrhythmia target. In other examples, the non-image data can be automatically integrated with the input mappings. In some examples, the input mappings can be converted to point clouds.

At block 145, the at least one processor can combine the compatible format input mappings. For example, the input mappings can be combined to provide a more robust illustration of the mapped image (e.g., corresponding ventricle or atrium). In some examples, the input mappings can be overlapped (e.g., based on common data points between the common format mappings). For example, each input mapping can be used to make an individual determination that one or more cardiac arrhythmia target segments should be ablated. The one or more of the cardiac arrhythmia target segments, for each input mapping, can then be combined to determined segment overlap. For example, when each input mapping includes segments 1 and 2 (for ablation) and only one mapping includes segment 4 the determination can be segments 1 and 2. In some examples, the input mappings can be converted to point clouds and the point clouds can be combined.

At block 150, a confidence score of the one or more input mappings can be determined. In some examples, block 150 can be located before block 140, or at any point in method 101. For example, the confidence score can be determined for each input mapping, the combined input mapping, or the identified cardiac arrhythmia target. In an example, the confidence score may be an assessment of the combined input mappings. The confidence score can also incorporate clinical data or any data used to adjust the target. For example, the input mappings weights, the weights between input mappings, agreement of data between the different input mappings, or the amount of overlap of results (e.g., segment of ablation, etc.) can be used to determine a confidence score. For example, the confidence score can be determined to quantify the quality and reproducibility of one or more segments or contours for ablation. In some examples, the confidence score can be increased with higher degrees of overlap between imaging groups (e.g., segments to ablate, etc.). In other examples, the confidence score can be decreased with incomplete input mapping, poor quality of input mapping, increased number of VTs, large scar size (e.g., scar greater than ablation), etc.

At block 155, a risk profile can be determined. In some examples, the risk profile can be determined from historical input mappings, side-effects, segment volume limit, and/or results from previous recommended segments for ablations (e.g., at block 160). For example, data associated with previous patients undergoing method 101 (or similar methods) and results of any procedures performed using data or mappings obtained through method 101 can be stored for determining the risk profile of a patient. In some examples, patient demographic information can be used to determine the risk profile (e.g., age, health, previous surgeries, etc.). In some examples, the historical input mapping, corresponding segment determinations and ablation results (from the determinations) can be used to determine which of the cardiac arrhythmia target segments you can treat without high risk and/or complications and further, which segments are generally high risk and/or have the most compilations. In at least one example, the risk profile is reported to the user/physician for therapy selection or counseling of toxicities.

Figure 2:
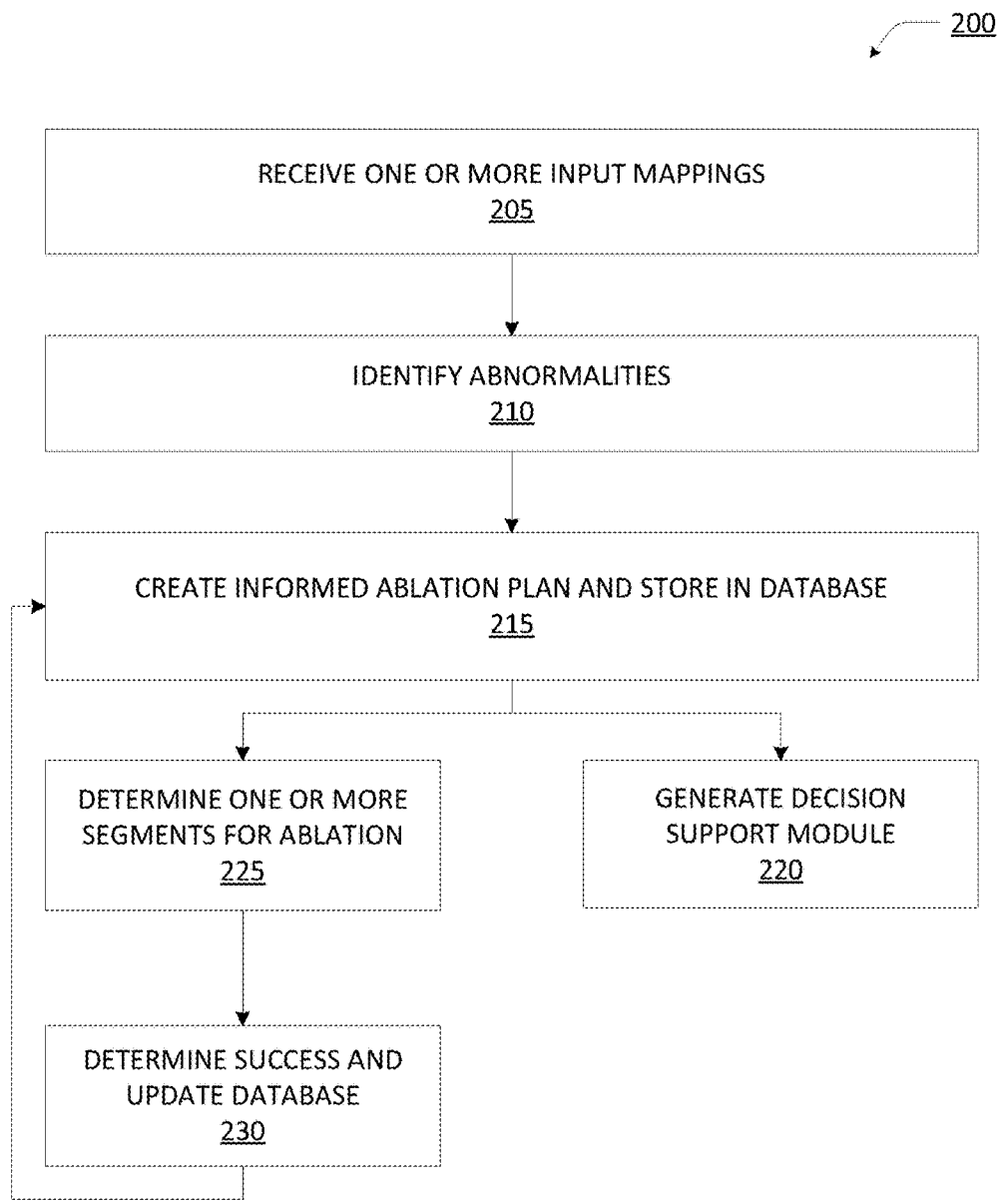
FIG. 2 illustrates a flow diagram of an example method of a 200.
Figure 5:
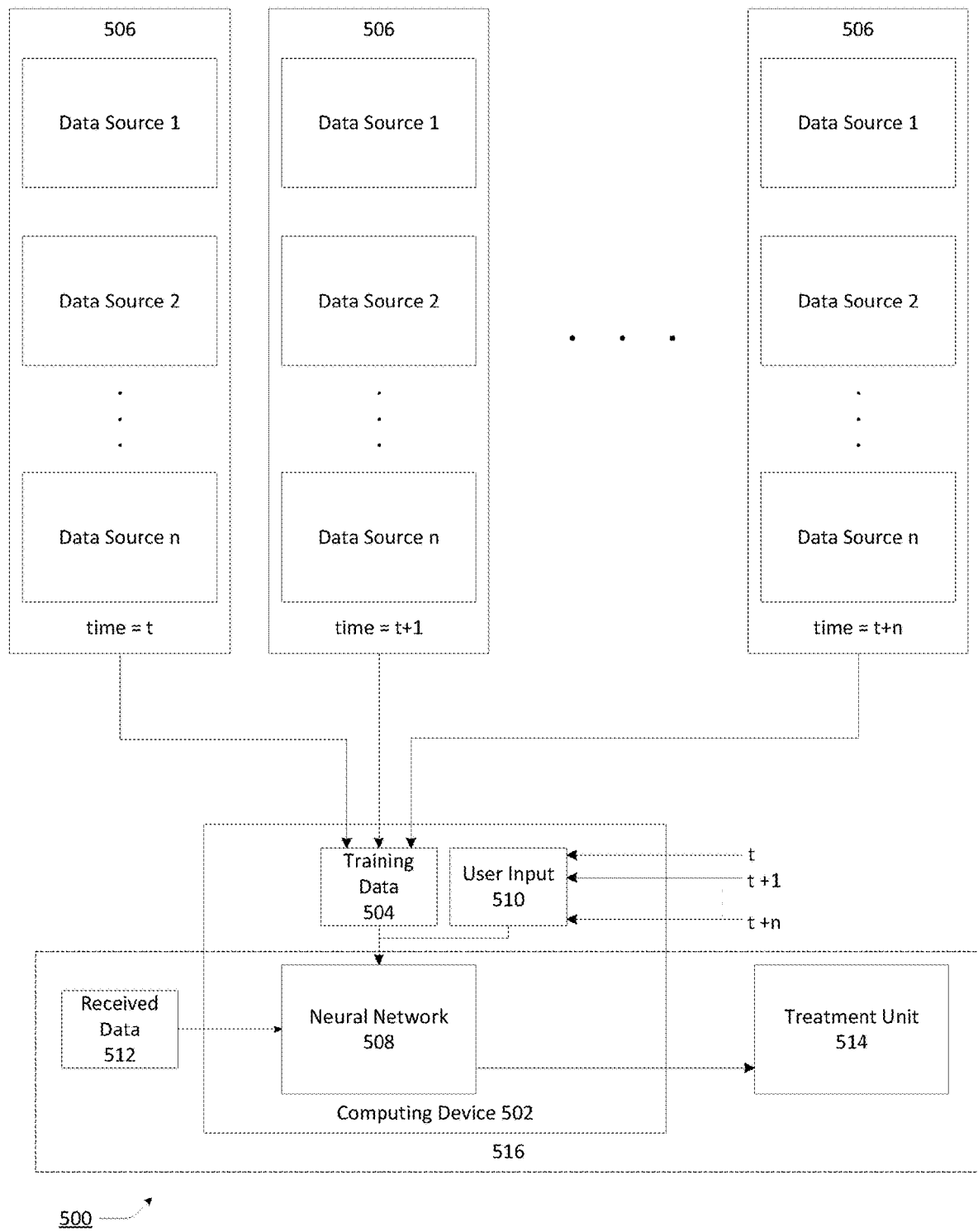
FIG. 5 illustrates an example machine learning environment.

In some examples, method 100 and method 101 can be used in a machine-learning environment (shown in FIG. 5). The target can be adjusted automatically using machine learning, as seen in FIGS. 2 and 5. For example, known clinical data and arrhythmia targets defined by the user over time can be used to suggest subsequent targeting for new similar clinical and multi-modal data scenarios or suggest selection of therapy for a new similar clinical and multi-modal data scenarios For example, the one or more inputs (at block 105, 125) along with the determination of one or more abnormalities (at block 110, 130) and the determination of one or more cardiac arrhythmia targets (at block 120, 160) can be used as input into a neural network (e.g., artificial neural network, convolutional neural network, etc.). The input into the neural network can also include other learning techniques, for example, supervised learning, reinforcement learning, etc. The neural network can continue to receive input (e.g., training data) over a period of time until the neural network is trained. The input into the neural network can also include data related to the success of a treatment, such as a success outcome, survival, side effects, etc. For example, the neural network is trained, when it can receive new input (e.g., never received) and can produce the one or more segments for ablation without requiring additional information (e.g., historical information, etc.). The trained neural network can be considered "autonomous." In an example, the machine learning environment can be used to predict success of an ablation procedure using past information such as patient success related to their confidence score.

In some examples, the determined segments can be provided on an image mapping for use in the ablation procedure. The image mapping can integrate with invasive and noninvasive delivery platforms. For example, the image mapping can be a volume for use in treatment planning (e.g., in a treatment planning system/software). In some examples, the image mapping can be used as an input to a treatment planning system (e.g., that can carry out the ablation). The image mapping can provide for patient customized treatment planning (e.g., not all patients will require or present with all known multi-modal data). In an example, the target segments or 3D contours may be used to identify a planning target volume within treatment planning software. In some examples, the planning target volume and/or the segments/contours can be used to simulate treatment for internal quality assurance.

The image mapping can facilitate arrhythmia targeting for pre-treatment targeting of both noninvasive and invasive ablation. In some examples, the one or more segments can be determined for ablation using one or more type of ablative energy techniques (e.g., SBRT, photon, carbon ions, protons, helium, ultrasound, etc.). In some examples, the one or more segments can be determined for a noninvasive arrhythmia guidance system. For noninvasive stereotactic cardiac ablation, the method can integrate with, transfer data to, or exist within a radiotherapy treatment planning system. In some examples, metrics for support can be provided with the one or more segments for ablation (e.g., as shown in Tables 1 and 2). In other examples, the one or more segments can be determined for invasive ablation. For invasive catheter ablation, the method can integrate with, transfer data to, or exist within a catheter ablation system. The method can be used to facilitate selection of therapy for a patient between noninvasive and invasive ablation. For example, a small, well defined target might be identified which would be readily amenable to catheter ablation, or a larger epicardial target might be identified which would be better suited to noninvasive ablation.

In some examples, the method can be directly interfaced into a noninvasive radiotherapy ablation delivery platform to facilitate real-time or near instantaneous targeting and delivery. For example, a patient that presents with a known arrhythmia (e.g., VT or Afib) is taken to the noninvasive ablation unit, where prior clinical and imaging data is entered. An ECGI vest can then be placed on the patient, who then undergoes volumetric imaging on the unit. For example, this can be performed with a cone beam CT with any modern linear accelerator or a volumetric MRI with a MR-guided unit. The ECGI vest can communicate directly with the unit. The communication with the unit provides real-time presentation of steady-state arrhythmia data (e.g., if the patient is active in an arrhythmia) or electrophysiologic data suggestive of an arrhythmia site or origin. In addition, localization of this signal in 3D space can be an additional means to track location of the target in real-time throughout internal and external motion of the patient. Targeting of the arrhythmia can be performed on or near the unit and planning of the noninvasive treatment is performed on or near the unit. Delivery of the noninvasive treatment can occur shortly thereafter, with tracking and/or gating of the target provided by both typical methods (e.g., onboard kV/MV, CBCT, MR, external/internal fiducial tracking) supplemented by real-time electrophysiologic data provided by ECGI.

Data representing the outcomes from previously treated patients can be used to enhance the generated image mapping method. In at least one example, a patient's risk profile, segments for ablation, and/or success in treatment may be stored in a database for informing future patient risk profiles. In some examples, the risk profile can be used to determine potential risk or impact to the patient associated with the recommended segments for ablation. In an example, over time, the method can predict consistent utilization of invasive catheter ablation for small endocardial lesions in the left ventricular apex in older males. Subsequent outcomes data reveals high rates of toxicity in this population and low rates of toxicity with similar outcomes in patients treated with noninvasive ablation. While the method would initially suggest further catheter ablation based on the multiplicity of prior treatments, the enhanced model would suggest noninvasive ablation. In various examples, the outcomes data can come from local data entry, multi-institutional data, or a combination of both.

In one example, the method 100 or 101 can be deployable as a remote service, with the potential for centers to submit data on their patients for analysis, targeting, and treatment recommendations, without having to deploy their own local instance of the method.

II. Decision Support Module

Further provided herein is a decision support module to provide an informed ablation plan to the physician and provide metrics for support about success and risks of various treatment option and opportunities to improve patient outcomes. After a target has been identified, the identified target(s) may be presented to a physician in the form of a decision support module. In addition, the decision support module may include one or more of a description of the scar pattern, a description of the scar burden size and location, a suggested volume to achieve ablation (e.g. full-thickness ablation, partial-thickness ablation, etc.), a confidence score of the combined mappings, a listing of at-risk structures, general recommendations, expected success with SBRT, expected success with alternative treatment modalities (e.g., catheter RF, antiarrhythmic drug (e.g. amiodarone), etc.), or combinations thereof. In some examples, the decision support module can further include a risk profile. In other examples, the decision support module can include patient demographics (e.g., age, gender, renal function, lung function, etc.), cardiac history (e.g., NYHA class, LVEF, prior CA, type of cardiomyopathy, prior antiarrhythmic drug use, etc.), cardiac imaging (e.g., heart size, scar size, scar location, number of VTs, etc.), and/or consistency of results e.g., confidence score, etc.).

The information in the decision support module may be generated based on the patient's suggested ablation target(s) and historical data from previous patients to inform the physician of all relevant information regarding treating the patient's arrhythmia with SBRT.

The method shown in FIG. 2 is provided by way of example, as there are a variety of ways to carry out the method. Additionally, while the example method is illustrated with a particular order of blocks, those of ordinary skill in the art will appreciate that FIG. 2 and the blocks shown therein can be executed in any order that accomplishes the technical advantages of the present disclosure and can include fewer or more blocks than illustrated. Each block shown in FIG. 2 represents one or more processes, methods or subroutines, carried out in the example method.

FIG. 2 shows a flow diagram of an example method 200 for generating a decision support module and determining one or more segments for ablation. In some examples, method 200 can be performed in real-time at an image planning system. In other examples, method 200 can be performed in planning for future use in an image planning system. Method 200 can include method 100 and/or method 101. At block 205, at least one processor can receive one or more input mappings as described herein above for method 100 and method 101. At block 210, the at least one processor can identify abnormalities in the one or more input mappings as described herein above for method 100 and method 101. In some examples, the abnormality is an abnormal myocardial substrate.

At block 215, the at least one processor can create an informed ablation plan. The ablation plan can be created using any data available, for example, the ablation plan may include segments with abnormalities, selected segments for ablation, weighting of input mappings, the confidence score, and/or the risk profile. The data and/or ablation plan for each patient may be stored on a database to inform future patient treatment. The database may also be populated with patient demographic information.

At block 220, the at least one processor can generate a decision support module to inform the physician of the ablation plan, risks, and other treatment information. In some examples, the decision support module may be referred to as the decision support tool. The decision support module may include a description of the scar pattern, a description of the scar burden size and location, the suggested target location(s), a suggested volume to achieve ablation (e.g. full-thickness ablation, partial-thickness ablation, etc.), a confidence score of the combined mappings, a listing of at-risk structures, general recommendations, expected success with SBRT, expected success with alternative treatment modalities (catheter RF, amiodarone, etc.), or combinations thereof. In an example, the decision support module may be displayed, printed, or provided to the physician in any form capable of providing the information. FIGS. 6A, 6B, and 6C are example outputs of the decision support module.

At block 225, the at least one processor can determine one or more segments for ablation as described herein above for method 100 or method 101. After treatment of the patient, method 200 may further determine the success of the treatment. The database may then be updated with the success information, including any side effects or problems encountered. The success information may adjust treatment recommendations or selection of segments for ablation for future patients.

In some examples, method 200 can be used in a machine-learning environment (for example, as shown in FIG. 5). The target can be adjusted automatically using machine learning. Future ablation plans and decision support modules may be automatically adjusted using machine learning. For example, blocks 215, 220, 225, and/or 230 may be adjusted automatically using machine learning. Machine learning tools and predictive analytics can be integrated within method 200 to create a clinical decision support infrastructure such as the decision support module. For example, known clinical data and arrhythmia targets defined by the user over time can be used to suggest subsequent targeting for new similar clinical and multi-modal data scenarios or suggest selection of therapy for a new similar clinical and multi-modal data scenarios For example, the one or more inputs (at block 205) along with the determination of one or more segments (at block 225) can be used as input into a neural network (e.g., artificial neural network, convolutional neural network, etc.) or learning algorithm. The input into the neural network can also include other learning techniques, for example, supervised learning, reinforcement learning, etc. The neural network can continue to receive input (e.g., training data) over a period of time until the neural network is trained. The input into the neural network can also include data related to the success of a treatment, such as a success outcome, survival, side effects, etc. For example, the neural network is trained, when it can receive new input (e.g., never received) and can produce the one or more segments for ablation and/or a decision support module without requiring additional information (e.g., historical information, etc.). The trained neural network can be considered "autonomous."

The decision support module may include a written description of the scar pattern. In some examples, the decision support module may further include a measurement of the scar burden, as seen in FIGS. 6A, 6B, and 6C. The measurement of the scar burden may include the volume of the scar (e.g. in cc) and/or the percentage of the ventricle myocardium that the scar covers.

The decision support module may include a listing of suggested ablation locations based on the identified targets for ablation, as seen in FIGS. 6A, 6B, and 6C. In some examples, the determined segments can be assigned priorities. For example, based on the combination of input mappings and risk profile the determined segments could be assigned high, medium or low priorities. In some examples, all of the cardiac arrhythmia target segments can be assigned a priority (e.g., high, medium or low). In other examples, the some or all of the cardiac arrhythmia target segments are assigned a numerical priority or the segments are listed in priority order. In other examples, a segment assigned a high priority and medium prior are provided in the determination. In an example, the decision support module may provide the priorities of the determined target segments or list the target segments for ablation in prioritized order as seen in FIG. 6B.

In some examples, the decision support module can further include the determined segments provided on an image mapping for use in the ablation procedure. The image mapping can integrate with invasive and noninvasive delivery platforms. For example, the image mapping can be a volume for use in treatment planning (e.g., in a treatment planning system/software). In some examples, the image mapping can be used as an input to a treatment planning system (e.g., that can carry out the ablation). The image mapping can provide for patient customized treatment planning (e.g., not all patients will require or present with all known multi-modal data). In some examples, the image mapping with determined segments is provided in the decision support module.

The decision support module can facilitate arrhythmia targeting for pre-treatment targeting of both noninvasive and invasive ablation. For noninvasive stereotactic cardiac ablation, the decision support module can integrate with, transfer data to, or exist within a radiotherapy treatment planning system. In other examples, the one or more segments can be determined for invasive ablation. For invasive catheter ablation, the decision support module can integrate with, transfer data to, or exist within a catheter ablation system. The decision support module can be used to facilitate selection of therapy for a patient between noninvasive and invasive ablation. For example, a small, well defined target might be identified which would be readily amenable to catheter ablation, or a larger epicardial target might be identified which would be better suited to noninvasive ablation.

In some examples, the decision support module can be directly interfaced into a noninvasive radiotherapy ablation delivery platform to facilitate real-time or near instantaneous targeting and delivery. The decision support module may further include a suggested volume to achieve ablation (e.g. full-thickness ablation, partial-thickness ablation, etc.), for example, as seen in FIGS. 6A, 6B, and 6C. The volume may be provided in cc and/or the percentage of the ventricle myocardium.

The decision support module may further include a confidence score. In some examples, a confidence score of the combined input mapping and/or identified cardiac arrhythmia target can be determined. In an example, the confidence score can be an assessment of the combined input mappings. The confidence score can also incorporate clinical data or any data used to adjust the target. For example, the input mappings weights, the weights between input mappings, agreement of data between the different input mappings, or the amount of overlap of results (e.g., segment of ablation, etc.) can be used to determine a confidence score. For example, the confidence score can be determined to quantify the quality and reproducibility of one or more segments or contours for ablation. In some examples, the confidence score can be increased with higher degrees of overlap between imaging groups (e.g., segments to ablate, etc.). In other examples, the confidence score can be decreased with incomplete input mapping, poor quality of input mapping, increased number of VTs, large scar size (e.g., scar greater than ablation), etc. In some examples, the confidence score may be displayed as a numerical value or a percentage (e.g., X of 10, X of 100) and/or categorically (e.g., low, medium/moderate, or high), as seen in FIGS. 6A, 6B, and 6C. The decision support module may also include a notation or comment as to why the confidence score is in a particular range, for example, as seen in FIG. 6B.

The decision support module may further include a listing of at-risk structures that may be impacted by SBRT treatment of the identified ablation locations. For example, the decision support module may list the organs or abbreviations for organs or tissues potentially at risk, as seen in FIGS. 6A, 6B, and 6C. In some examples, the at-risk structures may be informed by treatment of previous patients. For example, the results of ablation treatment of a previous patient may populate a database and be used to suggest at-risk structures in future patients with the same or similar ablation locations or clinical data.

The decision support module may include recommendations for additional procedures, follow-up/evaluation, further imaging etc., as seen for example in FIGS. 6A, 6B, and 6C. The recommendations provided in the decision support module may be provided from a database populated with possible recommendations. The recommendations may be provided from prior patients. For example, data representing the outcomes from previously treated patients can be used to enhance the generated image mapping method and the generated decision support module. In an example, over time, the method can predict consistent utilization of invasive catheter ablation for small endocardial lesions in the left ventricular apex in older males. Subsequent outcomes data reveals high rates of toxicity in this population and low rates of toxicity with similar outcomes in patients treated with noninvasive ablation. While the decision support module may initially suggest further catheter ablation based on the multiplicity of prior treatments, an updated decision support module would suggest noninvasive ablation. In various examples, the outcomes data can come from local data entry, multi-institutional data, or a combination of both.

The decision support module may further include expected success rates with various treatment modalities. In an example, the decision support module may include an expected success rate with SBRT, catheter RF, and/or amiodarone. In an example, the decision support module can further include the risk profile for therapy selection or counseling of toxicities.

In one example, the method 200 and/or the decision support module can be deployable as a remote service, with the potential for centers to submit data on their patients for analysis, targeting, and treatment recommendations, without having to deploy their own local instance of the method. In other examples, the method 200 and/or the decision support module may be integrated within a noninvasive treatment system. In some examples, the decision support module may be displayed, printed, or provided to the physician in any form capable of providing the information.

Figure 4:
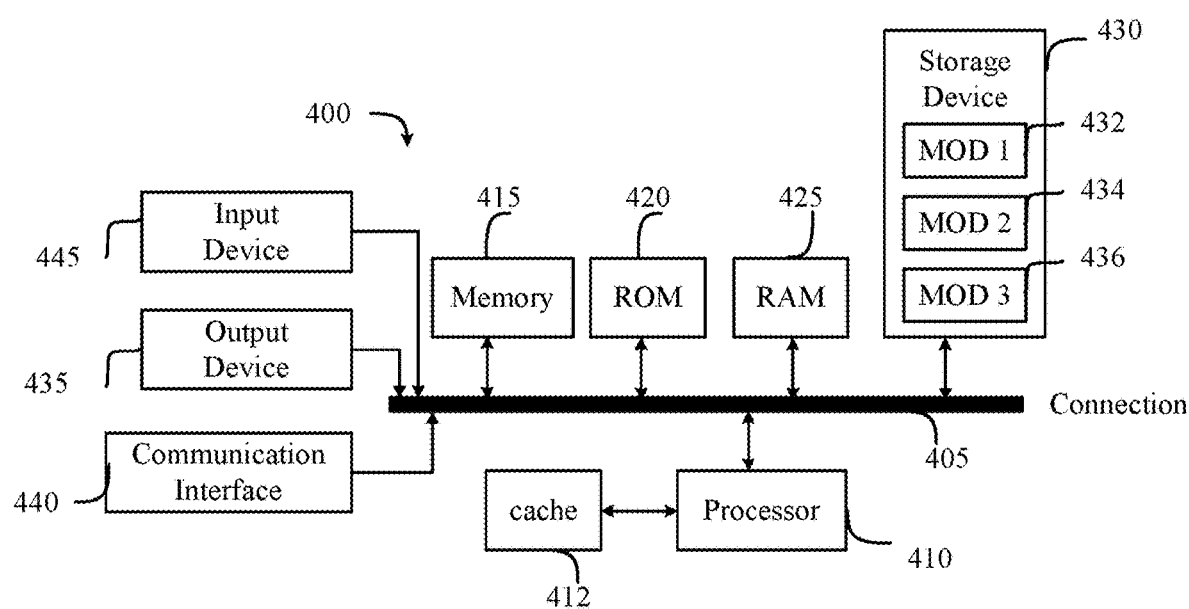
FIG. 4 illustrates example system embodiments.

The disclosure now turns to the example system illustrated in FIG. 4. FIG. 4 shows an example of computing system 400 in which the components of the system are in communication with each other using connection 405. Connection 405 can be a physical connection via a bus, or a direct connection into processor 410, such as in a chipset or system-on-chip architecture. Connection 405 can also be a virtual connection, networked connection, or logical connection.

In some examples computing system 400 is a distributed system in which the functions described in this disclosure can be distributed within a datacenter, multiple datacenters, a peer network, throughout layers of a fog network, etc. In some examples, one or more of the described system components represents many such components each performing some or all of the function for which the component is described. In some examples, the components can be physical or virtual devices.

Example system 400 includes at least one processing unit (CPU or processor) 410 and connection 405 that couples various system components including system memory 415, read only memory (ROM) 420 or random access memory (RAM) 425 to processor 410. Computing system 400 can include a cache of high-speed memory 412 connected directly with, in close proximity to, or integrated as part of processor 410.

Processor 410 can include any general purpose processor and a hardware service or software service, such as services 432, 434, and 436 stored in storage device 430, configured to control processor 410 as well as a special-purpose processor where software instructions are incorporated into the actual processor design. Processor 410 may essentially be a completely self-contained computing system, containing multiple cores or processors, a bus, memory controller, cache, etc. A multi-core processor may be symmetric or asymmetric.

To enable user interaction, computing system 400 includes an input device 445, which can represent any number of input mechanisms, such as a microphone for speech, a touch-sensitive screen for gesture or graphical input, keyboard, mouse, motion input, speech, etc. Computing system 400 can also include output device 435, which can be one or more of a number of output mechanisms known to those of skill in the art. In some instances, multimodal systems can enable a user to provide multiple types of input/output to communicate with computing system 400. Computing system 400 can include communications interface 440, which can generally govern and manage the user input and system output, and also connect computing system 400 to other nodes in a network. There is no restriction on operating on any particular hardware arrangement and therefore the basic features here may easily be substituted for improved hardware or firmware arrangements as they are developed.

Storage device 430 can be a non-volatile memory device and can be a hard disk or other types of computer readable media which can store data that are accessible by a computer, such as magnetic cassettes, flash memory cards, solid state memory devices, digital versatile disks, cartridges, battery backed random access memories (RAMs), read only memory (ROM), and/or some combination of these devices.

The storage device 430 can include software services, servers, services, etc., that when the code that defines such software is executed by the processor 410, it causes the system to perform a function. In some examples, a hardware service that performs a particular function can include the software component stored in a computer-readable medium in connection with the necessary hardware components, such as processor 410, connection 405, output device 435, etc., to carry out the function.

The disclosure now turns to FIG. 5, which illustrates an example machine learning environment 500. The machine learning environment can be implemented on one or more computing devices 502A-N (e.g., cloud computing servers, virtual services, distributed computing, one or more servers, etc.). The computing device(s) 502 can include training data 504 (e.g., one or more databases or data storage device, including cloud-based storage, storage networks, local storage, etc.). The training data 504 of the computing device 502 can be populated by one or more data sources 506 (e.g., data source 1, data source 2, data source n, etc.) over a period of time (e.g., t, t+1, t+n, etc.). In some examples, training data 504 can be labeled data (e.g., one or more tags associated with the data). For example, training data can be one or more images and a label (e.g., VT or no VT) can be associated with each image. In some examples, the labeled data can be actual target probabilities (e.g., each segment as the weighted average over all received images for each patent). The computing device(s) 502 can continue to receive data from the one or more data sources 506 until the neural network 508 (e.g., convolution neural networks, deep convolution neural networks, artificial neural networks, learning algorithms, etc.) of the computing device(s) 502 are trained (e.g., have had sufficient unbiased data to respond to new incoming data requests and provided an autonomous or near autonomous recommended course of actions, and/or actually provide input to perform the course of action). In some examples, the neural network can be a convolutional neural network, for example, utilizing five layer blocks, including convolutional blocks, convolutional layers, and fully connected layers. Additional layers can be added to the neural network, for example, to learn target probability (e.g., probability of one or more cardiac arrhythmia targets, etc.). For example, the additional layers can combine individual segments into a weight average (e.g., learning weighted average indirectly). While example neural networks are realized, neural network 508 can be one or more neural networks of various types are not specifically limited to a single type of neural network or learning algorithm.

In other examples, a target probability can be generated (e.g., each segment as a weighted average over the images provided through the received data of the patient). In these instances, individual segments can be normalized and concatenated into 4D depth images of specific depths. The neural networks can be trained based on the depth of the images, e.g., to predict continuous target probabilities (e.g., ranging from 0 to 1). The training data can require an equivalent number of images per patient, and as such, if a missing image exists a substitute image can be generated based on the existing images (e.g., in order to enable sufficient training data, while not biasing the training data).

In some examples, while not shown here, the training data 504 can be checked for biases, for example, by checking the data source 506 (and corresponding user input) verse previously known unbiased data. Other techniques for checking data biases are also realized. The data sources can be any of the sources of data for providing the input images (e.g., MRI, CT, 3D modeling, etc.) as described above in this disclosure.

The computing device(s) 502 can receive user (e.g., physician) input 510 related to the data source. The user input 510 and the data source 506 can be temporally related (e.g., by time t, t+1, t+n, etc.). That is, the user input 510 and the data sources 506 can be synchronous in that the user input 510 corresponds and supplements the data source 506 in a manner of supervised or reinforced learning. For example, a data source 506 can provided an MRI image at time t and corresponding user input 510 can be input of ablations of that MRI image at time t. While, time t may actually be different in real-world time, they are synchronized in time with respect to the data provided to the training data. In other examples, the user input can classify segments as VT or no VT as described herein.

The training data 504 can be used to train a neural network 508 or learning algorithms (e.g., convolutional neural network, artificial neural network, etc.). The neural network 508 can be trained, over a period of time, to automatically (e.g., autonomously) determine what the user input 510 would be, based only on received data 512 (e.g., imaging data, etc.). For example, by receiving a plurality of unbiased data and/or corresponding user input for a long enough period of time, the neural network will then be able to determine what the user input would be when provided with only the data. For example, a trained neural network 508 will be able to receive an MRI image (e.g., 512) and based on the MRI image determine the ablations that a physician would manually identify (and that would have been provided as user input 510 during training). In some examples, this can be based on labels associated with the data as described above. The output from the trained neural network can be provided to a treatment unit 514 for treating a patient. In some examples, the output from the trained neural network can be inputted directly into a treatment unit to perform a procedure on a patient.

Trained neural network system 516 can include a trained neural network 508, received data 512, and treatment unity 514. The received data 512 can be information related to a patient, as previously described above. The received data 512 can be used as input to trained neural network 508. Trained neural network 508 can then, based on the received data 512, label the received data (e.g., VT or no VT) and/or determine a recommended course of action for treating the patient, based on how the neural network was trained (as described above). The recommended course of action or output of trained neural network 508 can be used as an input into a treatment unit 514 (e.g., to perform a procedure on the patient to which the received data 512 corresponds). In other instances, the output from the trained neural network can be provided in a human readable form, for example, to be reviewed by a physician to determine a course of action (e.g., less evasive, verification, etc.).

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims. Moreover, claim language reciting "at least one of" a set indicates that one member of the set or multiple members of the set satisfy the claim.

EXAMPLES

Example 1

The treatment described in this example was delivered to patients on the basis of their clinical circumstances, without specific testing of a research hypothesis. All the patients received a detailed explanation of the risks of treatment from both the treating electrophysiologist and radiation oncologist; all the patients provided written informed consent to treatment. Institutional review board approval had previously been provided for the use of electrocardiographic imaging. At the time of the study, the SBRT device had received 510(k) premarket approval from the Food and Drug Administration, but its use in the patients reported here was considered to be off-label clinical use; this information was conveyed to the patients who were included in this study.

Patients with structural heart disease, placement of an implantable cardioverter—defibrillator (ICD), and treatment-refractory ventricular tachycardia with limited conventional therapeutic options for noninvasive cardiac ablation of ventricular tachycardia (noninvasive radioablation) on a case-by-case basis were evaluated. Patients were considered for noninvasive radioablation if they had had at least three episodes of ICD-treated ventricular tachycardia in the preceding 3 months, despite having received at least two antiarrhythmic medications and having undergone at least one catheter-ablation procedure (or having a contraindication to catheter ablation). Evaluation of the patients for cardiac transplantation was encouraged, according to institutional standard of care, but transplantation eligibility was not an absolute condition for consideration. Patients who had undergone placement of a left ventricular assist device were not evaluated for inclusion in the study.

Figure 7:
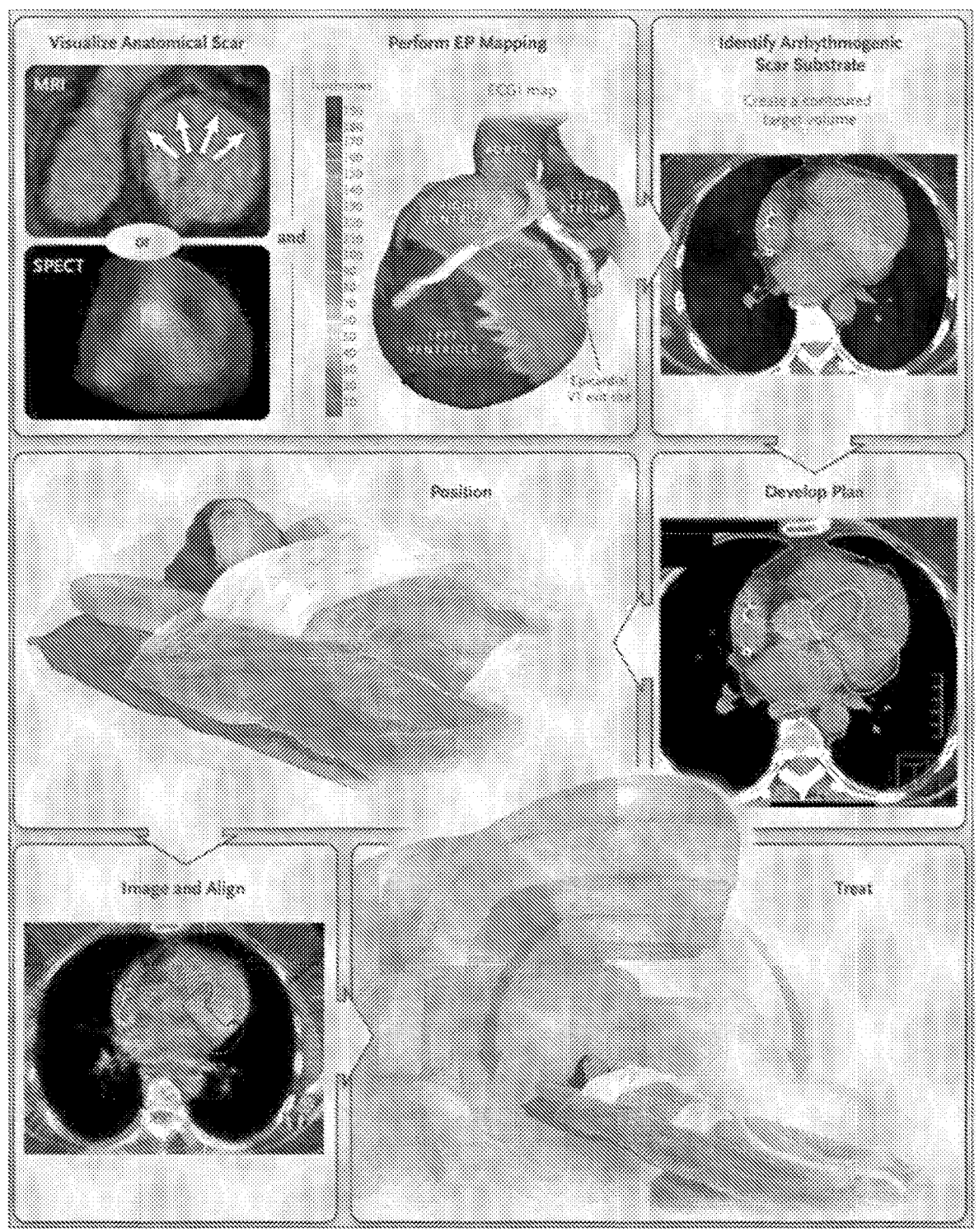
FIG. 7 illustrates an example workflow for Electrophysiology-Guided, Noninvasive Cardiac Radioablation.

The procedural workflow for noninvasive radioablation is shown in FIG. 7. Before treatment, patients underwent noninvasive electrocardiographic imaging during induced ventricular tachycardia to precisely map the ventricular tachycardia circuit. For electrocardiographic imaging, patients wore a vest of 256 electrodes (BioSemi) and underwent chest CT scanning. Patients were then brought to the electrophysiology laboratory and underwent noninvasive programmed stimulation with the use of an indwelling ICD to induce ventricular tachycardia. Data for electrocardiographic imaging maps were obtained, and the ICD was used to terminate ventricular tachycardia with a brief overdrive-pacing maneuver. Electrocardiographic imaging maps were created to identify the site of earliest electrical activation during ventricular tachycardia (the "exit site").

When clinically available, additional cardiac imaging was used to identify regions of anatomical scarring with either resting single-photon emission CT (SPECT) or contrast-enhanced cardiac MRI with the use of standard techniques (FIG. 7). Electrical information from the electrocardiographic imaging and information from the anatomical scarring were combined to build a volumetric target for radioablation that targeted the area of the first 10 msec of ventricular tachycardia (the exit site) and the full myocardial thickness of the associated ventricular scar.

In addition, before treatment, patients underwent a planning CT scan, which included immobilization of the entire body from thorax to legs with the use of a vacuum-assisted device (BodyFIX, Elekta) and acquisition of a respiration correlated CT scan (four-dimensional CT) to assess the sum total of cardiac and pulmonary motion. A final target (planning target volume) was developed by expanding the target, as defined above, to account for motion, setup uncertainty, and delivery uncertainty.

A total dose of 25 Gy in a single fraction was prescribed to be administered to the planning target volume with a goal of achieving maximal dose coverage while avoiding a dose in excess of calculated dose constraints to surrounding organs, including the esophagus, stomach, lungs, and spinal cord. All plans were subjected to, and passed, standard internal physics quality assurance on a calibrated phantom before delivery.

SBRT was performed with the use of an image-guided radiotherapy-equipped linear accelerator (TrueBeam, Varian Medical Systems) that uses cone-beam CT to acquire images of the thorax, which can be directly registered to the planning CT. This procedure results in accurate alignment of the heart and target volume without the need for invasive placement of a fiducial marker. During treatment, patients were placed in their custom immobilization device, which was aligned with the use of the cone-beam CT, with verification of the alignment by means of fluoroscopy. All the patients were treated without the use of any additional imaging during treatment and without sedation or anesthesia.

After treatment, patients were followed according to the standard of care for patients undergoing ablation of ventricular tachycardia. All ICDs were reprogrammed with a monitor-only zone at 100 bpm to assess for slow ventricular tachycardia. Patients were enrolled in a remote monitoring program for devices to enhance rapid identification and interpretation of any ICD detected arrhythmias. Patients were seen in the outpatient clinic with ICD interrogations every 2 weeks for 2 months, monthly for the next 4 months, and then 1 year after treatment.

At each visit, an attempt was made to wean patients off their antiarrhythmic medications to mitigate known short-term and long-term toxic effects of these drugs. If no further ventricular arrhythmias were detected, doses of antiarrhythmic medications were reduced or stopped, with the goal of discontinuing all antiarrhythmic medications after the 6-week visit. Patients continued to receive medical therapy (including beta-blockers) for heart failure before and after treatment.

Episodes of ventricular tachycardia were tallied as the sum of appropriate ICD shocks, appropriate ICD antitachycardia pacing, and sustained (>30 seconds), nontreated ventricular tachycardia in the monitor zone. The treating electrophysiologists adjudicated all ICD interrogations. Patients underwent echocardiography at baseline and at 1, 6, and 12 months after treatment to assess for cardiac adverse events. Patients also underwent chest CT at baseline and at 3 and 12 months to assess for thoracic adverse events in accordance with routine standard of care for thoracic SBRT.

From April through November 2015, nine patients were evaluated for noninvasive radioablation; of these patients, five received the treatment. Of the four patients who did not receive treatment, two declined to participate (one chose to enter hospice care and died from complications of ventricular tachycardia 1 week later, and one chose to undergo an invasive procedure for ventricular tachycardia ablation), one died of progressive cardiogenic shock before treatment, and one underwent implantation of a left ventricular assist device, with recurrent ventricular tachycardia storm after surgery.

Table 1 outlines the demographic and clinical data for each patient.

TABLE 2

Demographic and Clinical Characteristics of the Patients and Treatment Details.*

| Variable | Patient 1 | Patient 2 | Patient 3 | Patient 4 | Patient 5 |
|---|---|---|---|---|---|
| Demographic or clinical characteristic | | | | | |
| Age (yr) | 61 | 60 | 65 | 62 | 83 |
| Sex | Male | Male | Male | Male | Female |
| Type of cardiomyopathy | Nonischemic | ischemic | Nonischemic | Noischemic | Ischemic |
| NYHA class | IV | III | IV | IV | IV |
| Left ventricular ejection fraction (%) | 37 | 17 | 22 | 26 | 15 |
| No. of previous antiarrhythmic drugs | 3 | 3 | 3 | 4 | 2 |
| No of previous catheter ablations | 1 | 0 | 2 | 4 | 0 |
| No of induced episodes of ventricular tachycardia | 2 | 1 | 0 | 5 | 8 |
| No. of episodes of ventricular tachycardia 3 mo before treatment | 30 | 20 | 5 | 2210 | 4312 |
| Treatment | | | | | |
| Ablation target region | Anterior basal left ventricle | Anterolateral basal left ventricle | Inferior left ventricle | Left ventricle outflow and septum | Inferolateral mid left ventricle |
| Ablation volume (ml) | 51.3 | 87.3 | 48.5 | 53.0 | 81.0 |
| Treatment time (min) | 12 | 12 | 14 | 12 | 18 |
| Length of hospital stay after treatment (days) | 2 | 1 | 2 | 2 | 1 |
| Antiarrhythmic medication at discharge | Amiodarone, mexiletine | Amiodarone, mexiletine | Amiodarone, mexiletine | Amiodarone, mexiletine | Amiodarone, mexiletine |
| No. of episodes of ventricular tachycardia during 6-wk blanking period | 0 | 3 | 0 | 355 | 322 |
| No. of episodes of ventricular tachycardia 10.5 mo after blanking period | 3 | 0 | 1 | 0 | NA |
| No. of additional ablation procedures performed by 1 yr | 0 | 0 | 0 | 1 at 4 wk | NA |
| Antiarrhythmic medication at 1 yr | None | None | Amiodarone (restarted at 9 mo) | None | NA |

TABLE 2-continued

Demographic and Clinical Characteristics of the Patients and Treatment Details.*

| Variable | Patient 1 | Patient 2 | Patient 3 | Patient 4 | Patient 5 |
| --- | --- | --- | --- | --- | --- |

*NA denotes not applicable because the patient died 3 weeks after treatment, and NYHA New York Heart Association.

The mean age of the five treated patients was 66 years (range, 60 to 83). The mean number of episodes of ventricular tachycardia per patient in the 3 months before treatment was 1315 (range, 5 to 4312). All the patients were taking two antiarrhythmic drugs at the time of evaluation. Previous invasive catheter-ablation procedures had failed in three patients. Two patients had contraindications to invasive catheter ablation: one (Patient 2) had a new mechanical prosthetic mitral valve and evidence of epicardial ventricular tachycardia, and one (Patient 5) was deemed to be too frail for any invasive procedures. All five patients had New York Heart Association class III or IV heart-failure symptoms. The mean left ventricular ejection fraction was 23% (range, 15 to 37).

All the patients underwent noninvasive electrocardiographic imaging for mapping of their ventricular tachycardia. Four patients had inducible ventricular tachycardia (mean number of circuits, three; range, one to six). Electrocardiographic imaging was performed during all induced episodes of ventricular tachycardia. In one patient (Patient 3), ventricular tachycardia could not be induced and no electrocardiographic imaging was obtainable, so the results of 12-lead electrocardiography and previous invasive catheter mapping were used to guide the creation of a volumetric target. Treatment characteristics are provided in Table 1. Ablation target volumes ranged from 17 to 81 ml (mean, 49). On-table treatment times ranged from 11 to 18 minutes (mean, 14).

Figure 9A:
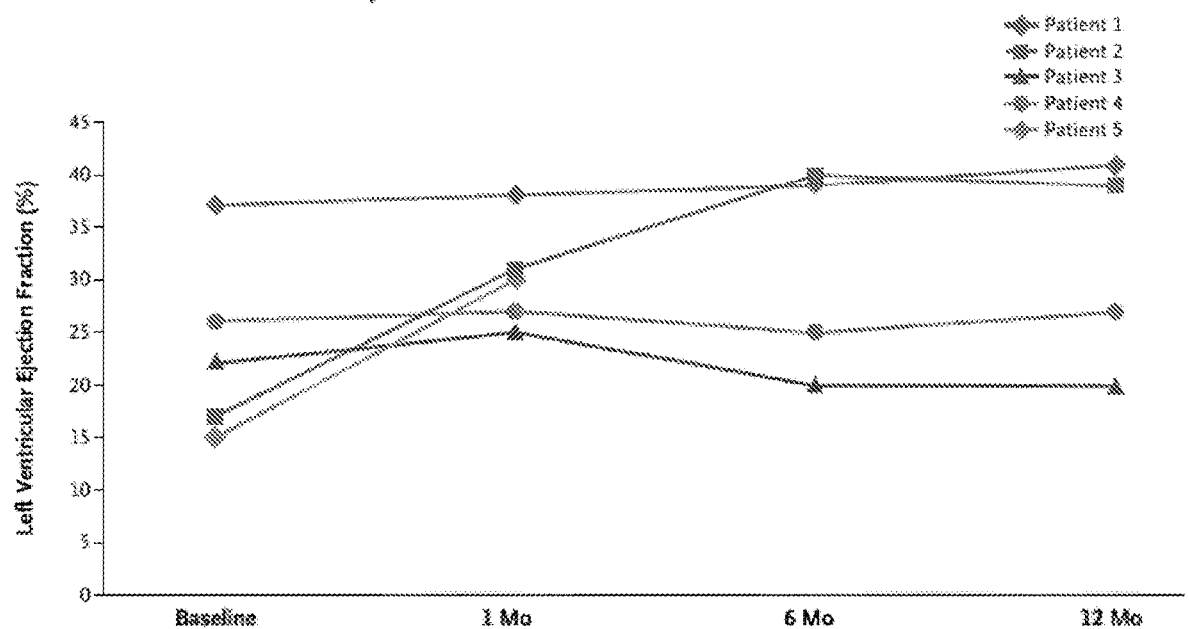
FIG. 9A shows serial evaluation of the left ventricular ejection fraction after treatment in each of the study patients, as assessed on echocardiography. The mean value increased by 6 percentage points (range, 0.2 to 22).
Figure 9B:
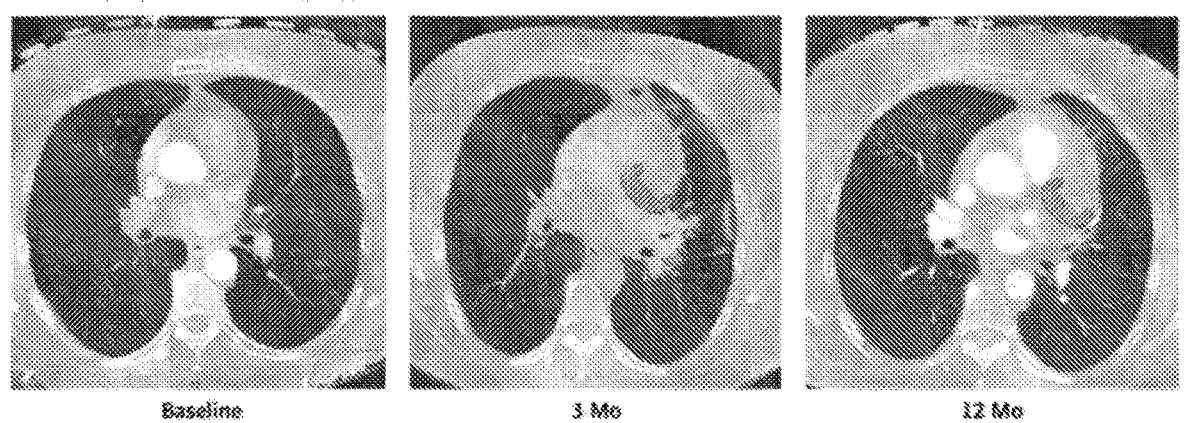
FIG. 9B shows serial thoracic CT scans after treatment in Patient 1. The treatment area is shown in blue. At 3 months, there were adjacent local inflammatory changes in the lung parenchyma, effects that had nearly resolved at 12 months.

At a median follow-up of 12 months, a marked reduction in the burden of ventricular tachycardia occurred after treatment (Table 1 and FIGS. 9A-9C). In aggregate, there were 6577 episodes of ventricular tachycardia in the 15 patient-months before treatment. During the 6 weeks immediately after ablation (the "blanking period," when arrhythmias may occur because of postablation inflammation), there were 680 episodes of ventricular tachycardia. After the 6-week blanking period, there were 4 episodes of ventricular tachycardia during the next 46 patient-months, for a relative reduction of 99.9% from baseline.

Figure 8A:
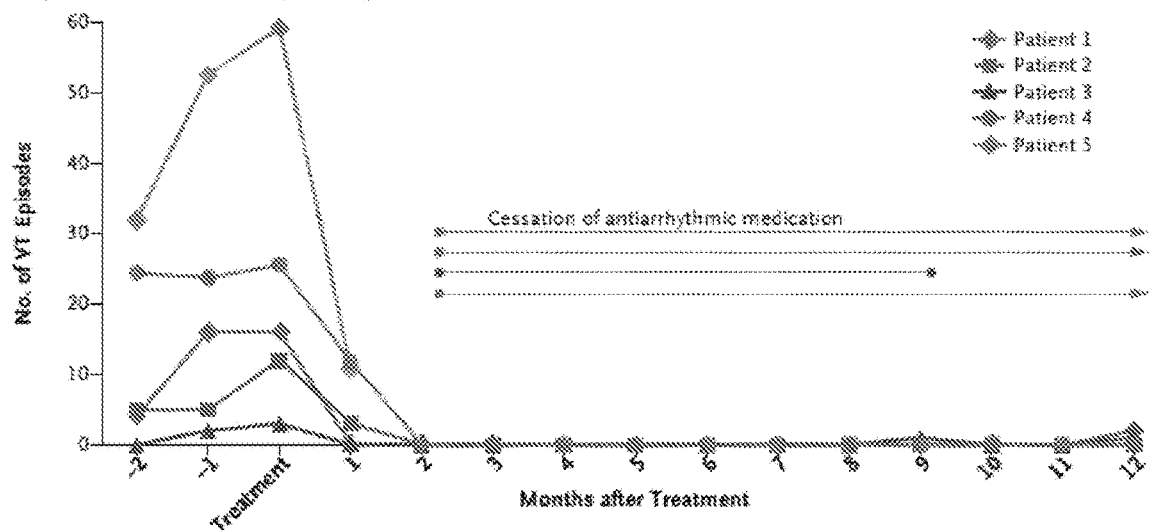
FIG. 8A shows the total numbers of episodes of ventricular tachycardia (VT), including appropriate shocks from an implantable cardioverter—defibrillator (ICD), appropriate ICD antitachycardia pacing, and sustained untreated VT, in each of the five study patients, for 3 consecutive months before treatment and continuing for 12 months after treatment. In Patients 4 and 5, the numbers of VT episodes were markedly greater than in Patients 1, 2, and 3; therefore, the numbers that are shown for Patients 4 and 5 have been divided by 30 to allow comparisons on the same scale.
Figure 8B:
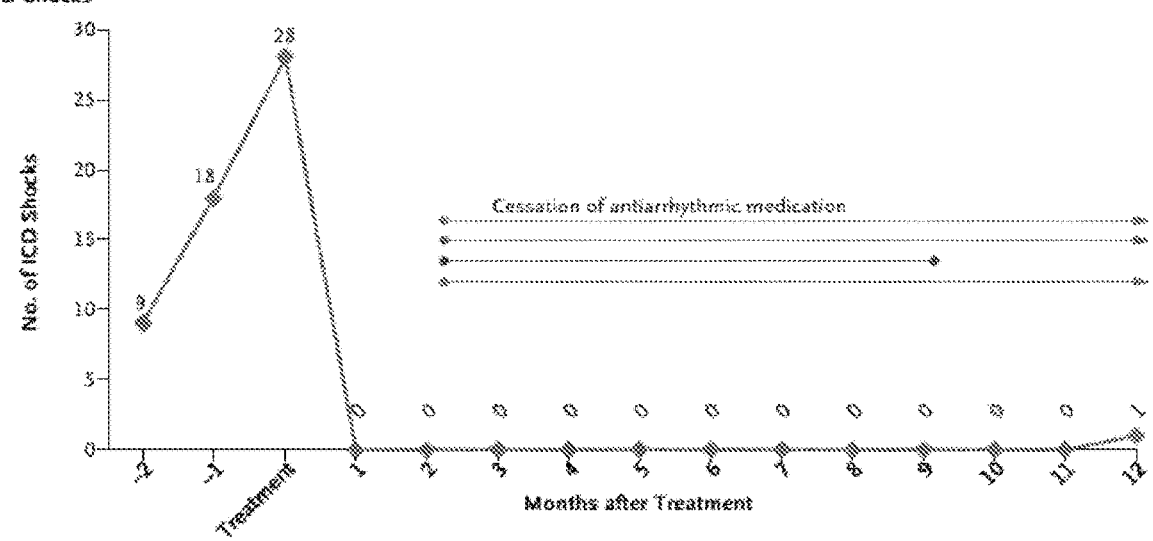
FIG. 8B the total numbers of ICD shocks for all five patients during the same time frame as FIG. 8A.
Figure 8C:
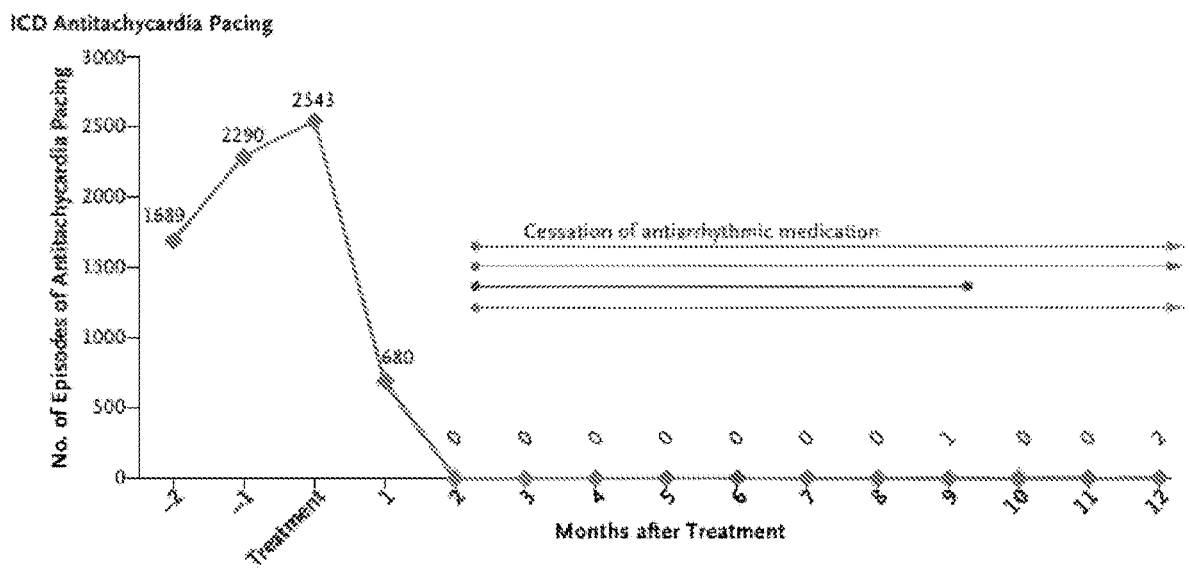
FIG. 8C shows numbers of episodes of antitachycardia pacing for all five patients during the same time frame as FIG. 8A.

FIG. 8A shows the monthly number of episodes of ventricular tachycardia on a per-patient basis. Every patient had a reduction in ventricular tachycardia burden. Of the four patients who were alive at 12 months, three were not receiving any antiarrhythmic medication. Patient 3 restarted amiodarone 9 months after treatment after the first episode of antitachycardia pacing. Patient 4 underwent an additional invasive catheter ablation procedure at 4 weeks after treatment because of incomplete cessation of ventricular tachycardia, with no further episodes thereafter. Improvement was observed with respect to both the number of ICD shocks (an aggregate number of 55 ICD shocks before treatment vs. 1 shock after treatment) (FIG. 8B) and ICD antitachycardia pacing (6577 episodes before treatment vs. 3 episodes after treatment) (FIG. 8C).

No complications occurred during the treatment or index hospitalization. Three patients reported fatigue on the day after treatment. No acute heart-failure exacerbations occurred in the immediate period after treatment. Patients were discharged home 1 to 3 days after treatment.

No adverse effects were observed in ICD system performance, lead thresholds, or lead impedances at any point after treatment. Serial echocardiography showed no pericardial effusions. The mean change in the left ventricular ejection fraction at the last follow-up visit was an absolute increase of 6 percentage points (range, 0.2 to 22) (FIG. 9A). No pulmonary symptoms occurred after treatment. Serial CT at 3 months showed findings that were consistent with inflammatory changes in the adjacent lung tissue that were typical of thoracic SBRT, with near-complete resolution at 12 months (FIG. 9B). At 12 months, there was no chest pain or apparent changes to the myocardium or coronary arteries on CT in the region targeted for treatment.

During follow-up, after amiodarone was discontinued, sinus-node function recovered in three patients. Heart rates in sinus rhythm occasionally exceeded the ICD programmed cutoff rate for detection (100 bpm). This situation required ICD reprogramming to avoid inappropriate therapy.

One patient (Patient 5) had a fatal stroke 3 weeks after treatment. This 83-year-old woman had a history of atrial fibrillation, severe cardiomyopathy, and other risk factors for stroke. Because of a risk of frailty-related bleeding, oral anticoagulants were not prescribed for stroke prevention. In the 3 weeks after treatment, her burden of ventricular tachycardia was reduced by 82% (from 1777 episodes of antitachycardia pacing in the month before treatment to 322 episodes after treatment). Her left ventricular ejection fraction had increased from 15% to 30%. No intracardiac thrombus was seen on echocardiography or during pathological assessment. It remains unclear whether the stroke was associated with SBRT or with preexisting medical conditions that placed her at high risk for stroke.

Figure 10A:
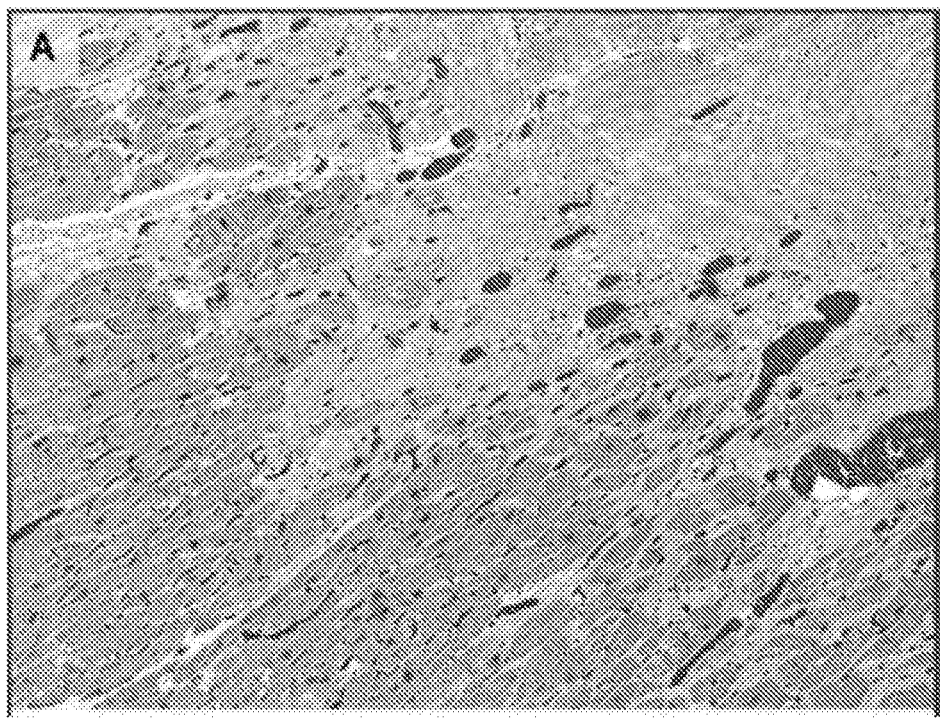
FIG. 10A shows prominent small-vessel ectasis at the interface of dense fibrosis (upper right) and viable myocardium (lower left) in postmortem cardiac samples obtained from Patient 5, who had a fatal stroke 3 weeks after treatment. There is no acute myocardial inflammation or acute cellular necrosis.
Figure 10B:
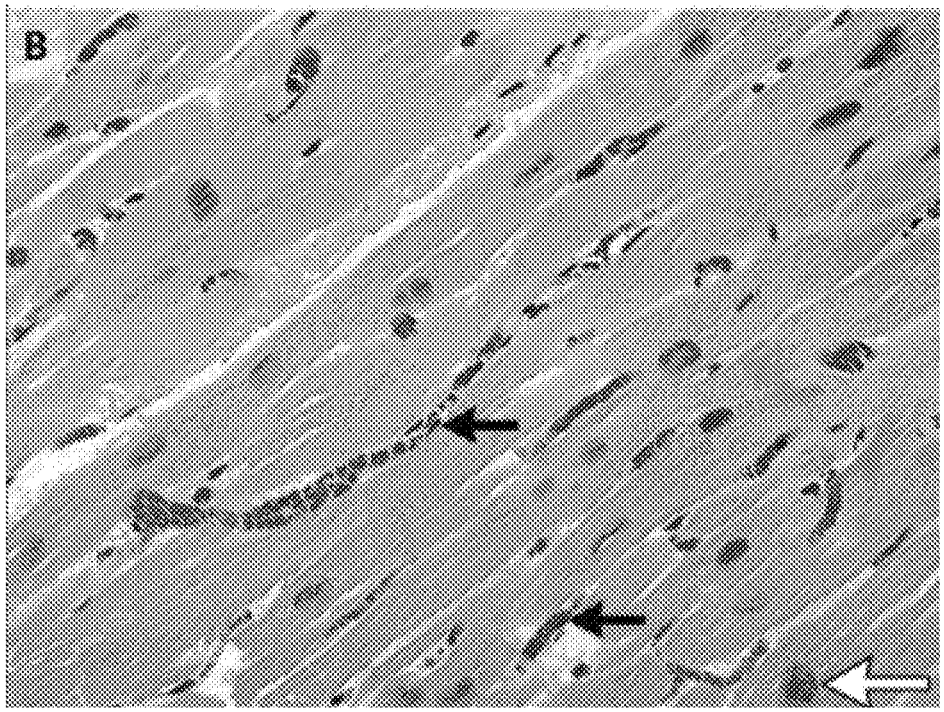
FIG. 10B shows rectangular "boxcar" nuclei and surrounding dilated arterioles and venules, consistent with radiation exposure. Endothelial cells are normal in appearance (black arrows), showing long, thin, nonreactive nuclei. Hypertrophic cardiomyocytes (white arrow) are also seen.

Consent was obtained for postmortem cardiac pathological assessment in Patient 5. Prominent ectatic blood vessels were identified at the interface of dense scar and viable myocardium (scar border zone) (FIG. 10A). This pattern has been described as a component of the acute vascular injury that is usually observed in the early weeks after radiation exposure. In such cases, the injury pattern is typically accompanied by endothelial-cell swelling, vacuolization, and perivascular tissue edema. However, in this patient, the endothelial lining of these vessels appeared to be normal and nonreactive, without evidence of an acute vasculitis or tissue edema (FIG. 10B). No evidence of acute myocyte necrosis, hemorrhage, or acute inflammation was observed. The relative contributions of remote myocardial infarction and acute cardiac SBRT to the formation of dense scar are unknown.

Example 2

The ENCORE-VT trial was a prospective single-arm phase I/II trial conducted at a single center. Local institutional review board (IRB) approved the study without Investigational Device Exemption (IDE) based on interpretation of the indications for use and risk of linear accelerators and electrocardiographic imaging technology. All participants provided informed consent, and an independent Data and Safety Monitoring Committee reviewed data semi-annually and provided guidance on study continuation. Subsequent to study enrollment, FDA reviewed the protocol and categorized the research as a significant risk study, which requires IDE approval. The investigators, IRB, and FDA worked together to ensure that the appropriate human subject protections were in place.

Eligible patients were ≥18 years old and had a) ≥3 episodes of sustained monomorphic VT, or b) cardiomyopathy (left ventricular ejection fraction (LVEF)<50%) related to monomorphic PVCs (PVC>20%), and required failure of ≥1 antiarrhythmic medication and ≥1 catheter ablation (or have a contraindication to catheter ablation). Patients could not have received past radiotherapy to the anticipated treatment field. Patients were deemed ineligible if they had heart failure dependent on inotropes and/or a left-ventricular assist device, or were deemed unlikely to live 12 months in the absence of VT. Patients were also ineligible if they had polymorphic VT or ventricular fibrillation, more than 3 distinct clinical VT morphologies or more than 5 induced VT morphologies during noninvasive-programmed stimulation (NIPS) testing.

Targeting

Protocol-specified baseline studies for targeting included a cardiac CT, cardiac MRI, PET/CT, 12-lead ECG, and acquisition of ECGI during induced VT during NIPS testing. NIPS and ECGI methods have been previously described. A synthesis of imaging studies and electrophysiologic mapping were used to guide SBRT in each patient with the principle being to target all areas of ventricular scar approximating the VT exit site that harbor related circuits.

Treatment and Follow-Up

Patients received a single dose of 25 Gy delivered with SBRT to the arrhythmogenic target as defined above. Following completion of treatment, a pre-specified ICD programming plan was implemented for all patients, which included a zone for detection at least 20 ms slower than the slowest clinical or induced VT. ICDs were remotely monitored as part of clinical care. If not contraindicated, oral anticoagulation was prescribed during the first month after treatment. Study visits occurred at day 3, at 2, 4, and 6 weeks, 6, and 12 months, and annually thereafter. Adverse events were continuously assessed, and ICD interrogation was performed at each study visit. A 12-lead ECG was obtained at day 3, at 6 weeks, and 3, 6, and 12 months. For patients with PVCs, 24 hour Holter monitor was performed at week 6, and months 3, 6, and 12. Chest CT was performed along with ECGI (without NIPS) at 3 and 12 months.

Outcome Measures and Statistical Analysis

The ENCORE-VT trial was designed with co-primary endpoints of (1) safety and (2) efficacy. The primary safety endpoint was defined as the rate of ≤90 day serious adverse events (SAEs) defined using Common Terminology Criteria for Adverse Events (CTCAE, v4.0) criteria that were treatment-related (possibly, probably, or definitely related to study treatment). SAEs were defined as any grade 3 toxicity requiring hospitalization, or any grade 4-5 toxicity. An early stopping rule was set to halt protocol enrollment if 5 or more of the first 10 patients developed a SAE.

The primary efficacy endpoint was defined as the number of subjects with any reduction in number of ICD treatments for VT or 24-hour PVC burden comparing the 6 month period before and after SBRT, with a 6 week blanking period after treatment to allow for a treatment effect. ICD treatments are composed of ICD shocks and anti-tachycardia pacing (ATP). Additional select pre-specified secondary objectives reported herein include stricter efficacy endpoints (50% reduction, 95% reduction), a patient-derived endpoint (reduction in shocks for VT patients, improvement in cardiac function for PVCs), overall survival, late (>90 day to 1 year) adverse events, and quality of life as measured by the SF-36 questionnaire.

The study was powered as a balance between assuring a high likelihood of safety with a preliminary assessment of efficacy. Considering all patients had failed previous treatments to halt VT, the population in this study was expected to be at higher risk, and an assumption was made that SAE rates up to 20% and efficacy as low as 40% would be clinically acceptable. Using a one-sided one sample test for proportions, 19 patients provided a 75.4% power to determine that the SAE rate was not truly higher than 20% (range, 5-20%, alpha=0.0829) and a 81.5% power to determine that efficacy was not worse than 40% (range, 40-65%, alpha=0.0885).

Continuous variables are reported as the median and range. The Wilcoxon signed-rank test was used to compare the number of VT events, ICD shocks, and ATP events between baseline and 6 month time points. McNemar's paired testing was used to assess changes in the proportions of anti-arrhythmic use. For quality of life analysis, mean values in each of the Short Form-36 measures at baseline, 6 weeks, and 6 months were compared using a repeated measures ANOVA with Greenhouse-Geisser correction. Median follow-up was calculated from the date of treatment to the date of last scheduled follow-up or death. Kaplan-Meier analysis was used to estimate the survival function. All statistics were performed in IBM SPSS Statistics for Windows, Version 24.0, Armonk, NY, 2016.

Patients and Treatment

Table 2 outlines the demographic data for the cohort, that was characterized by median age 66 years, 89.5% male (n=17), ischemic cardiomyopathy (n=11, 57.9%), median LVEF 25% (range, 15-58), New York Heart Association (NYHA) class III/IV (73.7%).

TABLE 2

| Variable | N = 19 |
|---|---|
| Median Age (year) (range) | 66 (49-81) |
| Sex (n) (%) | |
| Male | 17 (89.5) |
| Female | 2 (10.5) |
| Race (n) | |
| Caucasian | 17 (89.5) |
| Black/AA | 1 (5.3) |
| Asian | 1 (5.3) |
| Median Body Mass Index (kg/m$^3$) (range) | 33.0 (24.3-48.6) |
| Median Age-Adjusted Charlson Score (range) | 4 (2-13) |
| Typer of Cardiomyopathy (n) (%) | |
| Ischemic | 11 (57.9) |
| Non-ischemic | 8 (42.1) |
| Idiopathic | 5 |
| Myocarditis (chronic) | 2 |
| Valvular | 1 |
| NYHA Class (n) (%) | |
| I | 1 (5.3) |
| II | 4 (21.1) |
| III | 10 (52.6) |
| IV | 4 (21.1) |
| Median Left ventricular ejection fraction (%) (range) | 25 (15-58) |
| Median Number of Previous Catheter Ablations (range) | 1 (0-4) |
| Total Number of Prior Catheter Ablation Approaches (n) | |
| Endocardial | 25 |

TABLE 2-continued

| Variable | N = 19 |
|---|---|
| Epicardial | 4 |
| Study Eligibility Criteria (n) (%) | |
| Incessant VT | 2 (10.5) |
| VT storm (>3 in 24 hours) | 10 (52.6) |
| ICD therapies (>3 shock or ATP in 6 months) | 5 (26.3) |
| PVC-related cardiomyopathy | 2 (10.5) |
| Device (n) (%) | |
| Single- or dual-chamber ICD | 8 (42.1) |
| Bi-ventricular ICD | 10 (52.6) |
| None | 1 (5.3) |
| More than one antiarrhythmic drug at baseline (n) (%) | 11 (57.9) |
| Current Antiarrhythmic drugs (n) (%) | |
| High dose amiodarone (≥300 mg/day) | 11 (57.9) |
| Low dose amiodarone (<300 mg/day) | 1 (5.3) |
| Class III (excluding amiodarone) | 6 (31.6) |
| Class I | 12 (63.2) |
| Other medications (n) (%) | |
| Beta-blocker | 18 (94.7) |
| Angiotensin Converting Enzyme (ACE)-Inhibitor | 10 (52.6) |
| Angiotensin Receptor Blocker (ARB) | 7 (36.8) |
| Oral Anticoagulation | 14 (73.7) |
| COPD/emphysema (n) (%) | 4 (21.1) |
| Diabetes Mellitus, Type 2 (n) (%) | 7 (35.8) |
| Hypertension (n) (%) | 10 (52.6) |
| Chronic Kidney Disease, Stage ≥3 (n) (%) | 9 (47.4) |

The median number of previous catheter ablations prior to enrollment was 1 (range, 0-4). Three patients did not have prior catheter ablation due to mechanical AVR and MVR (n=1), severely reduced LV ejection fraction with medical comorbidities precluding hemodynamic support (n=1), presence of mobile LV thrombus (n=1). Median follow up was 13 months, and no patients were lost follow-up.

Patients were enrolled for either ICD-treated VT (n=17) or PVC-related cardiomyopathy (n=2). Of the 17 patients with ICD-treated VT, 10 were considered VT storm (three or more VT episodes in 24 hours) and two were in sustained VT at the time of treatment. More than half (n=11, 57.9%) the patients were on >1 antiarrhythmic drug and taking ≥300 mg of amiodarone daily at the time of treatment.

Targeting and treatment characteristics are reported in Table 3. Ten patients were excluded from cardiac MRI primarily due to abandoned ICD leads. All patients underwent CT, nuclear imaging, and induction of VT with subsequent 12-lead ECG and ECGI images. Patients had a median of 2 VTs induced (range, 1-5).

TABLE 3

| Targeting data acquired at baseline (n) (%) | |
|---|---|
| Magnetic Resonance Imaging | 9 (47.4) |
| Nuclear imaging | 19 (100) |
| Electrocardiographic imaging | 19 (100) |
| 12-lead ECG | 19 (100) |
| Non-invasive Programmed Stimulation | |
| Median # of induced VT (range) | 2 (1-5) |
| Median Cycle length of induced VT (milliseconds) (range) | 360 (230-690) |
| Target location (n) * | |
| Segments in Left Ventricle | |
| Anterior | 5 |

TABLE 3-continued

| | |
|---|---|
| Lateral | 6 |
| Inferior | 6 |
| Septal | 3 |
| Apex | 4 |
| LV Summit | 2 |
| Segments in Right ventricle | 1 |
| Median Target Volume (cc's) (range) † | |
| Gross target volume | 25.4 (6.4-88.6) |
| Internal target volume | 31.0 (17.7-128.9) |
| Planning target volume | 98.9 (60.9-298.8) |
| Immobilization system (n) (%) | |
| Vacuum immobilization (Elekta BodyFIX) | 3 (15.8) |
| Abdominal compression (CDR FreedomX) | 15 (84.2) |
| Stereotactic Body Radiotherapy technique | |
| Volumetric modulated arc therapy | 17 (89.5) |
| Fixed-field intensity modulated therapy | 2 (10.5) |
| Linear accelerator | |
| Varian TrueBeam | 3 (15.8) |
| Varian Edge | 15 (84.2) |
| Median Stereotactic Body Radiotherapy beam-on time (min) (range) | 15.3 (5.4-32.3) |

Median gross target volume was 25.4 cc (range, 6.4-88.6). The PVC patients had the smallest GTV (6.4 cc, 11.5 cc). Accounting for motion and conservative additional margins for setup and delivery, median planning target volume was 98.9 cc (range, 60.9-298.8). Most (n=17, 89.5%) were treated with a volumetric modulated arc therapy technique. Median beam-on time was 15.3 minutes (5.4-32.3).

Safety

No acute toxicity was observed during or immediately after SBRT. No adverse effects were observed with ICDs during or after SBRT. Two patients (10.5%) experienced a grade 3 treatment-related (possibly, probably, or definitely related) SAE. One patient was hospitalized 65 days after treatment with a heart failure exacerbation (grade 3) and was conservatively scored as possible. Another patient was hospitalized at 80 days with pericarditis that improved with prednisone and was scored as probable. No grade 4 toxicity was recorded. An additional patient died 17 days after treatment in a nursing home resulting from an accident that was scored as unrelated and did not contribute to the 6 months primary efficacy endpoint. Early stopping rules were not met, and the DSMB recommended completion of the study.

Adverse events probably or definitely related to treatment were generally grade 1-2 (8 events in 4 patients, (22%)). Transient grade 1 fatigue and hypotension were common. Three patients required adjustment of antihypertensive medication due to hypotension within two weeks of treatment. Other common grade 1-2 adverse events included dizziness, dyspnea, and nausea. Two patients (11.1%) developed grade 2 radiation pneumonitis that resolved with steroids. Pericardial effusions were documented 6 times in 5 patients (28%); 3 were 2 asymptomatic, 1 resolved with medical management, and 2 were higher grade (1 possibly 3 related grade 3, 1 unrelated grade 4 after epicardial access). Patients with symptomatic 4 pericarditis or pneumonitis were treated with prednisone delivered at 1 mg/kg daily (max 560 mg), tapered by 10-20 mg per week based on symptoms. Six patients (33%) had at 6 least one hospital admission for heart failure at any point during follow-up.

Efficacy

Figure 11:
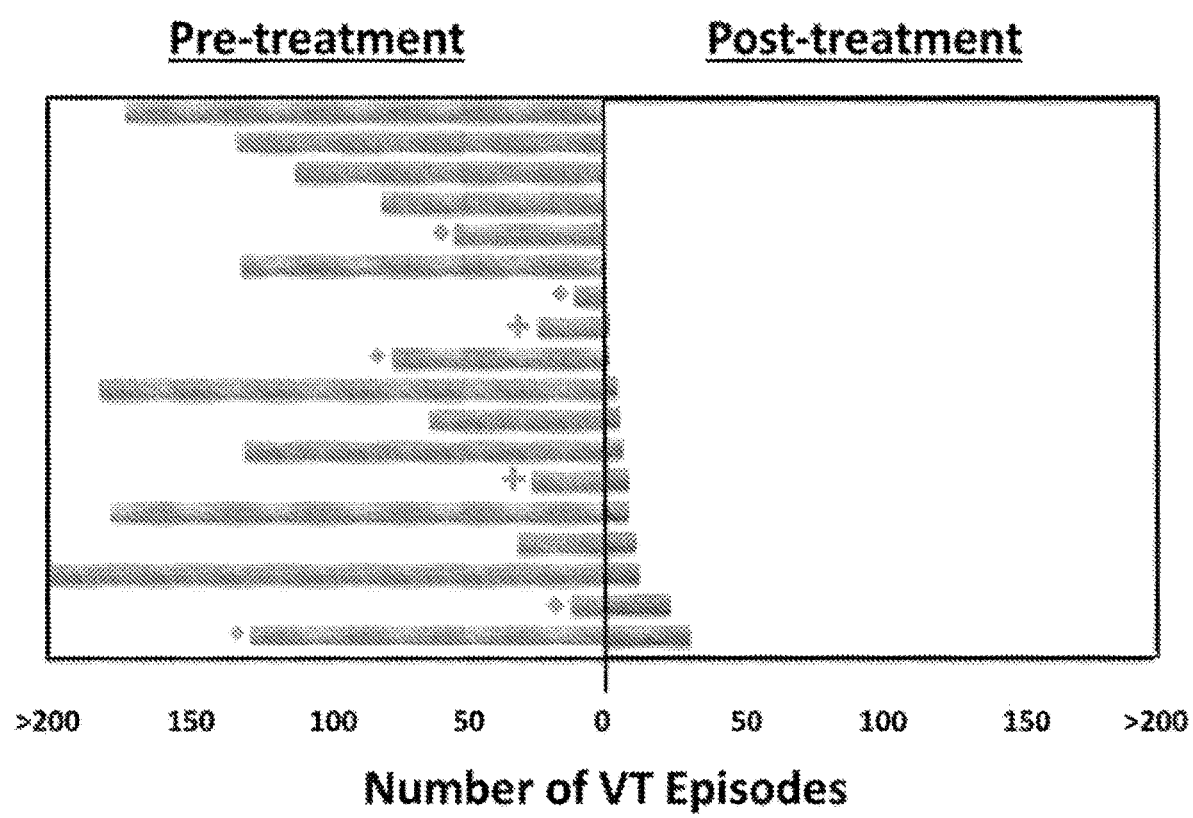
FIG. 11 shows an assessment of treatment efficacy. There were 18 patients who survived to 6 months. Patients with incessant VT or sustained slow VT below the ICD detection rate are noted with a diamond (n=5); these episodes were not included in the total. Patients with PVC-mediated cardiomyopathy are noted with a plus (n=2) and displayed as the PVC burden (percentage) captured on a 24 hour Holter monitor. Each line represents an individual patient; blue lines indicate pre-ablation and red lines post-ablation. Upper boundaries are artificially truncated at 200 episodes. Patients are arranged by recurrences during follow-up, ranging from greatest (bottom) to least (top).

Of the eighteen patients who survived 6 months, the primary efficacy endpoint of reduction in VT episodes or PVC burden was achieved in 17/18 (94%) patients. FIG. 11 shows the frequency of VT episodes and 24-hour PVC burden before and after noninvasive cardiac radioablation for all 18 patients.

For 16 evaluable patients with ICD-treated VT, there were 1778 VT episodes in aggregate in the 6 months prior to treatment. During the 6-week blanking period, there were 149 episodes. For the next 4.5 months, there were 111 VT episodes (94% total VT episode reduction). The median number of VT episodes decreased from the 6 month pre-ablation period (119, range 4-292) to the 6 month post-ablation period (3, range 0-31, p<0.001). Significant reductions in the median number of ICD shocks (pre-ablation 4, range 0-30 versus post-ablation 0, range 0-7, p=0.002), and for ICD ATP (pre-ablation 81, range 0-292 versus post-ablation 3.5, range 0-29, p=0.001) were observed.

Figure 12:
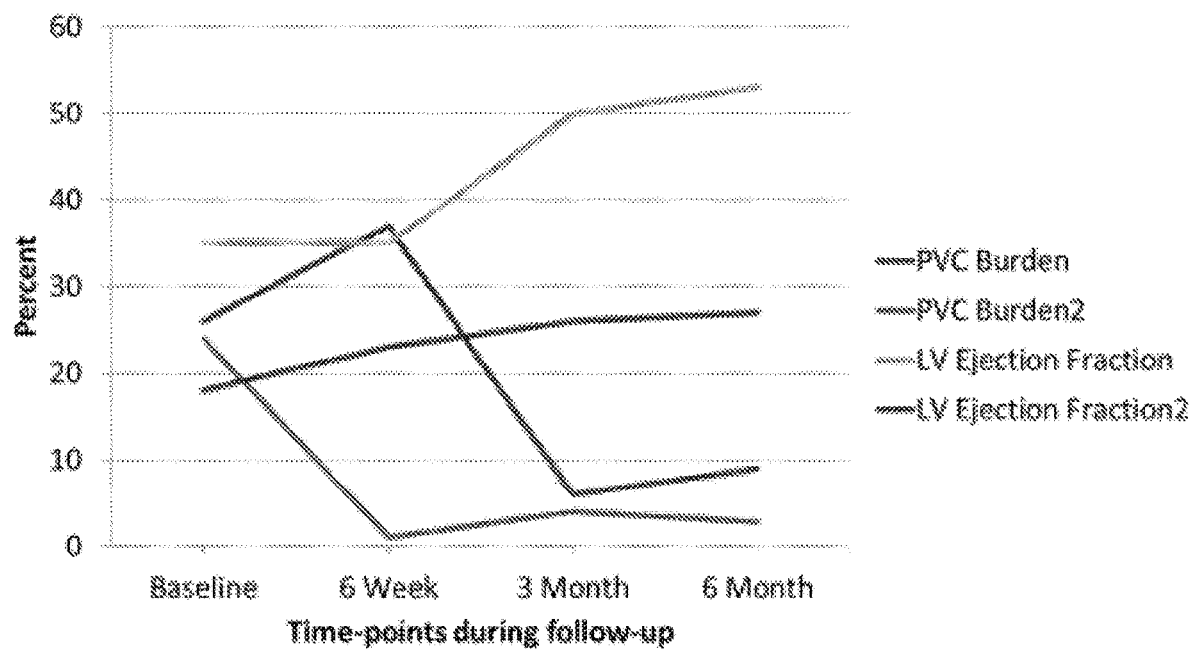
FIG. 12 shows 24-hour PVC burden and left ventricular ejection fraction changes. Two patients with PVC-related cardiomyopathy were enrolled and treated. The burden of PVC as measured by a 24-hour Holter monitor was 24% and 26% at baseline. Longitudinal PVC burden is shown (red lines). Left ventricular ejection fraction was measured with echocardiography. Longitudinal LV ejection fraction is shown (green lines). Both patients had improvement in LV ejection fraction as the PVC burden declined.

For 2 patients with PVC-related cardiomyopathy, 24-hour PVC burden reduced from 24% to 2% and 26% to 9%. LVEF improved by 13% and 8%, respectively, as seen in FIG. 12.

Figure 13A:
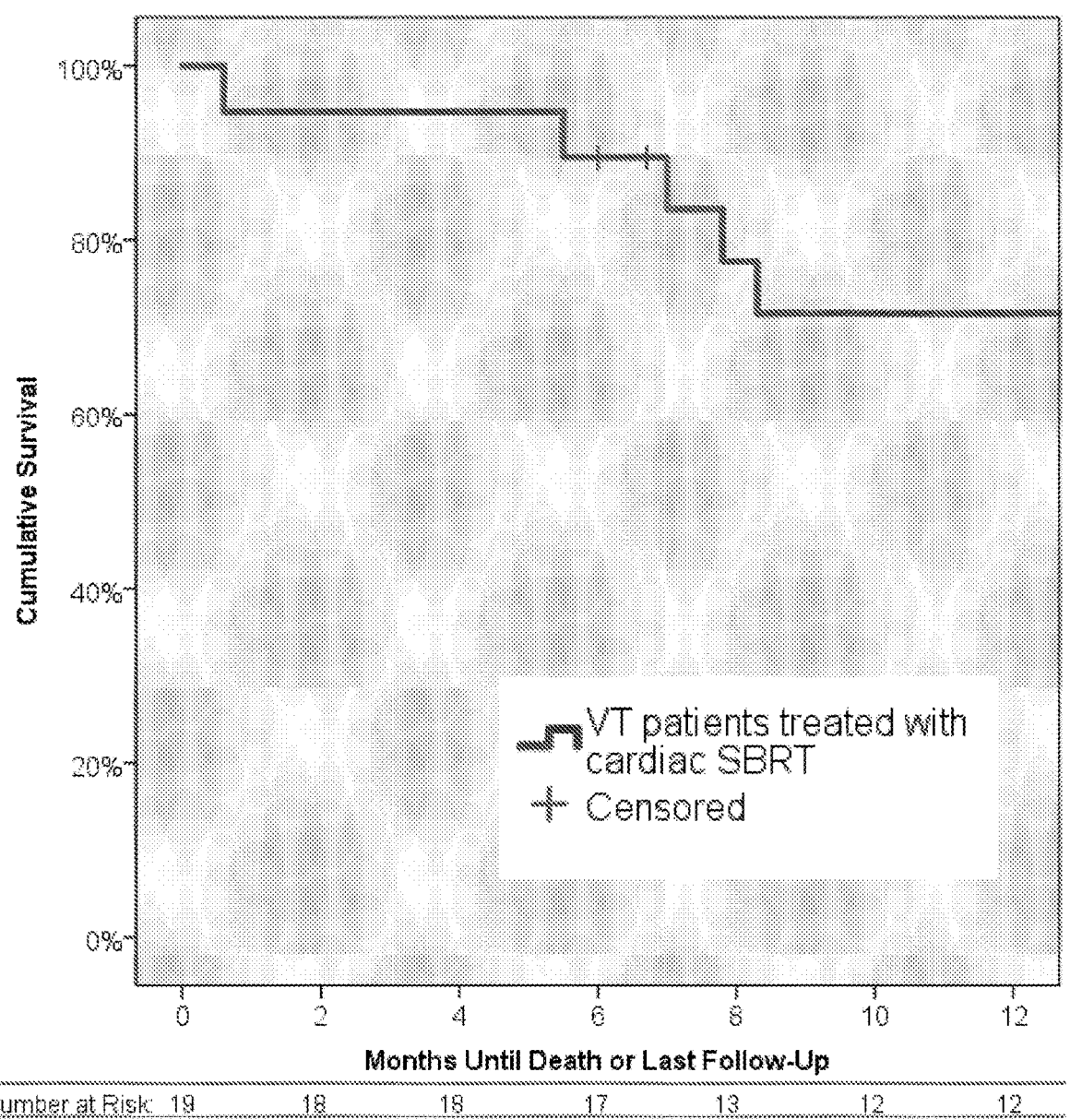
FIG. 13A shows a Kaplan-Meier curve of overall survival for all patients. Actuarial overall survival at 6 months was 89% and 12 months was 72%.

Pre-specified secondary endpoints included a 50% reduction and 95% reduction in VT episodes or 24-hour PVC burden. This endpoint was achieved in 94% and 61% of patients, respectively. The frequency of VT episodes or PVC burden was reduced by 75% in 89% of patients. A pre-specified secondary endpoint was elimination of ICD shocks and/or improvement in LVEF, which was reached in 72% of patients. Though VT burden was reduced in nearly all, many ($^{11}/_{16}$, 69%) had some recurrence of VT between the end of the six-week blanking period and six-months. Overall survival was 89% at 6 months and 72% at 12 months (FIG. 13A).

Figure 13B:
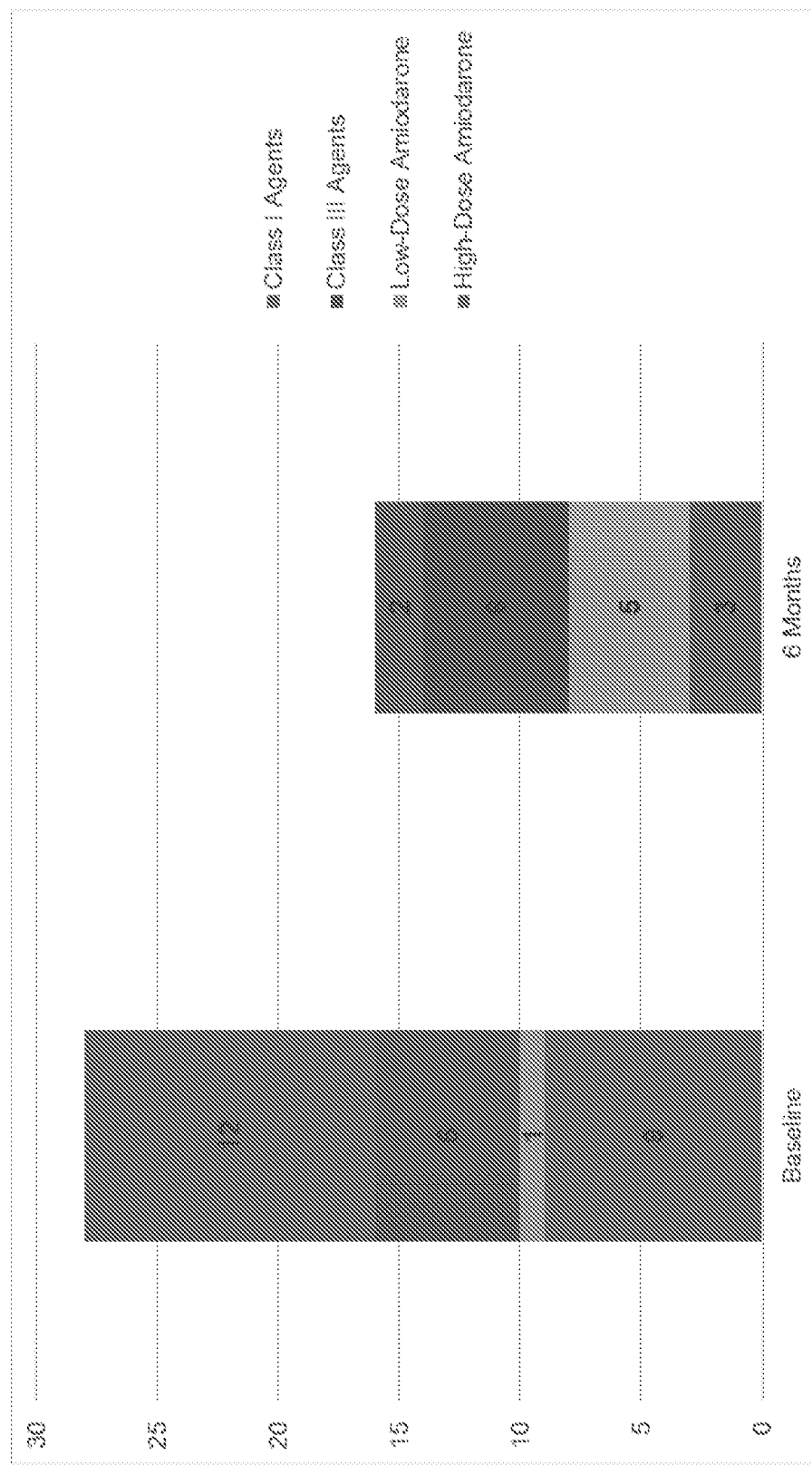
FIG. 13B shows a stacked bar graph of anti-arrhythmic medication usage in patients, at baseline and at 6 months after treatment. The y-axis represents the total number of anti-arrhythmic medications used, with the sizes of each color being directly proportional to the number of agents used in that particular class of anti-arrhythmic medication. Amiodarone usage is split into high dose (≥300 mg/day) and low dose (<300 mg/day). Class I agents consisted of mexiletine and flecainide. Class III agents consisted of sotalol.

FIG. 13B shows the distribution of antiarrhythmic medication use before treatment and at six months. Use of dual antiarrhythmic medications decreased from 58% to 11% (p=0.008). Use of high-dose amiodarone (>300 mg per day) decreased from 58% to 11%. Use of class 1 agents decreased from 67% to 11%. Four patients stopped antiarrhythmic medication completely.

Figure 13C:
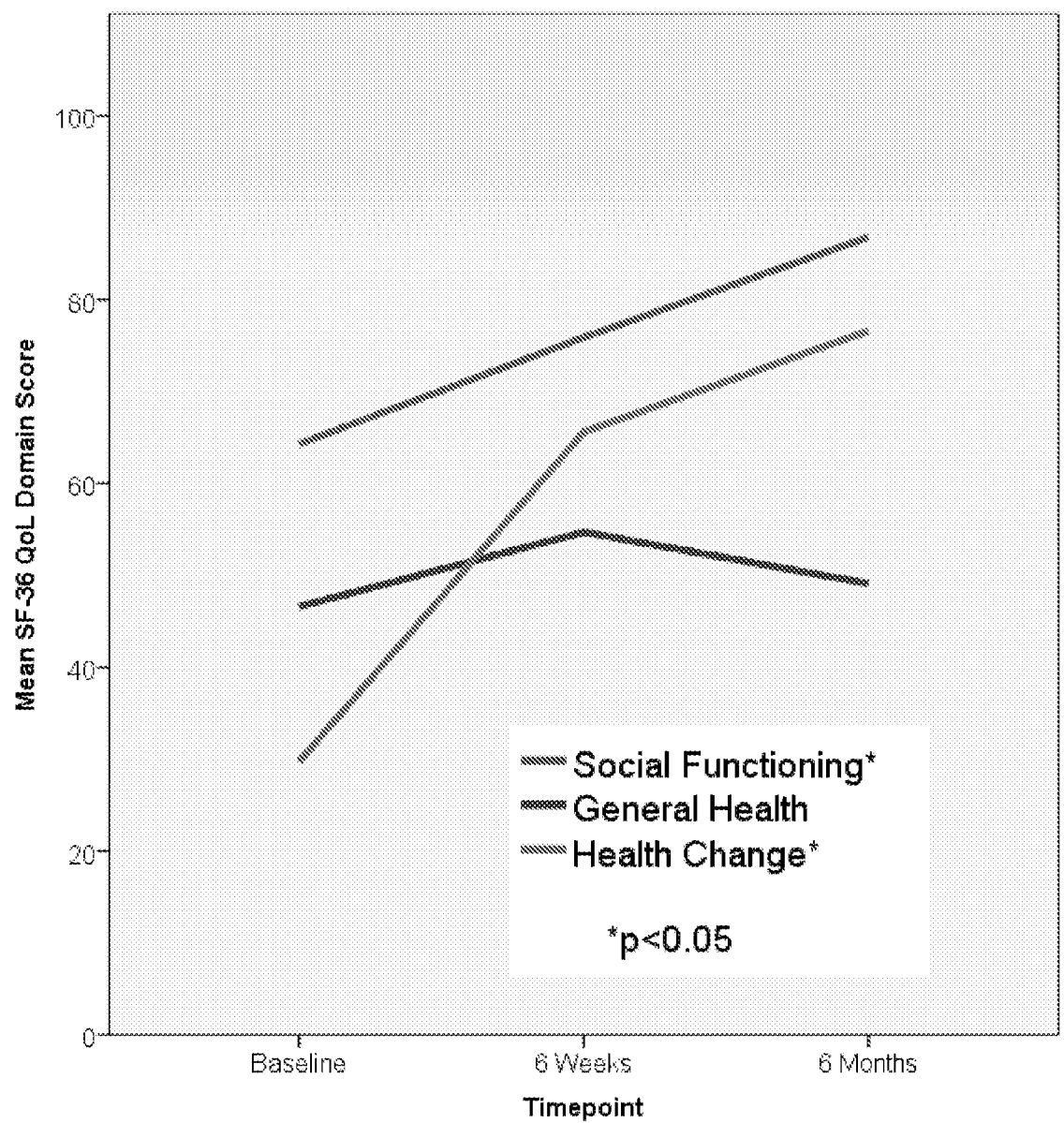
FIG. 13C graphically represents mean scores reported by the 18 patients who were alive at 6 months at baseline, 6 weeks, and 6 months after treatment in 3 selected domains of the Short Form-36 questionnaire—Social Functioning in blue, Health Change in green, General Health in purple. Asterisks denote a significant change (p<0.05) in mean scores over time.

Selected patient-reported quality of life scores are shown in FIG. 13C at baseline, 6 weeks, and 6 months after treatment. Significant improvements were observed in perceived health change and social functioning categories. No changes were observed in general health domain. Quality of life scores did not decline in any domain.

Example 3

This example provides patient sample data and an example output of the method for determining segments for ablation. The patient was a 50 year old man with nonischemic cardiomyopathy (normal coronary angiogram). The patient has an endocardial LV mapping/ablation procedure 2.5 years prior and was on antiarrhythmic medications. The patient had monomorphic VT with a cycle length (CL) of 300-320 ms and 183 antitachycardia episodes.

The left ventricle was segmented as seen in FIG. 3A. Previous map/ablation identified a minimal abnormal signal in segment 10 and an empiric catheter ablation of segment 10 was performed.

Figure 14:
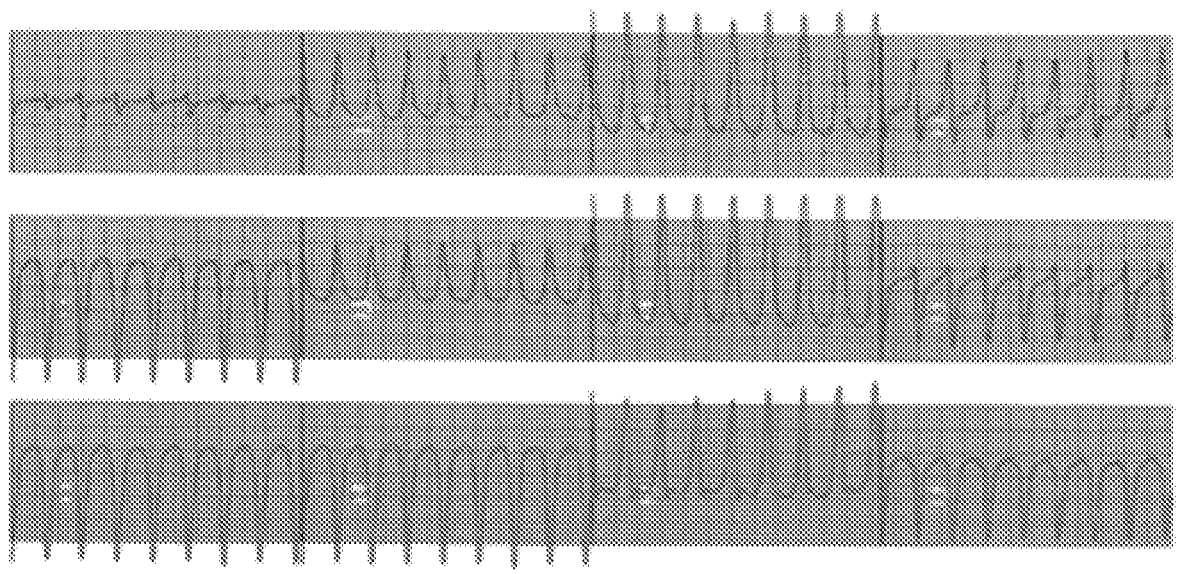
FIG. 14 shows an ECG of a patient in Example 3.

An ECG of the patient is shown in FIG. 14 which shows a VT1 at segment 10 with a CL of 300 ms and a HR of 200 bpm. This demonstrated that intracardiac EGMs matched clinical VT.

Figure 15A:
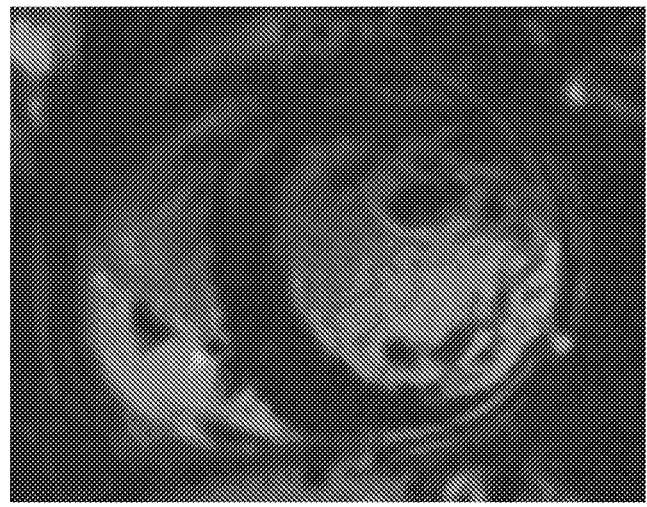
FIGS. 15A and 15B show MRI mapping of a patient in Example 3.
Figure 15B:
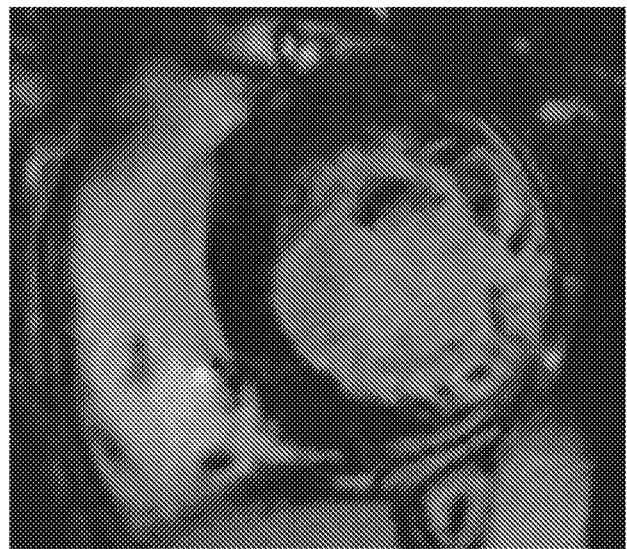
Figure 16A:
FIGS. 16A and 16B show CT mapping of a patient in Example 3.
Figure 16B:
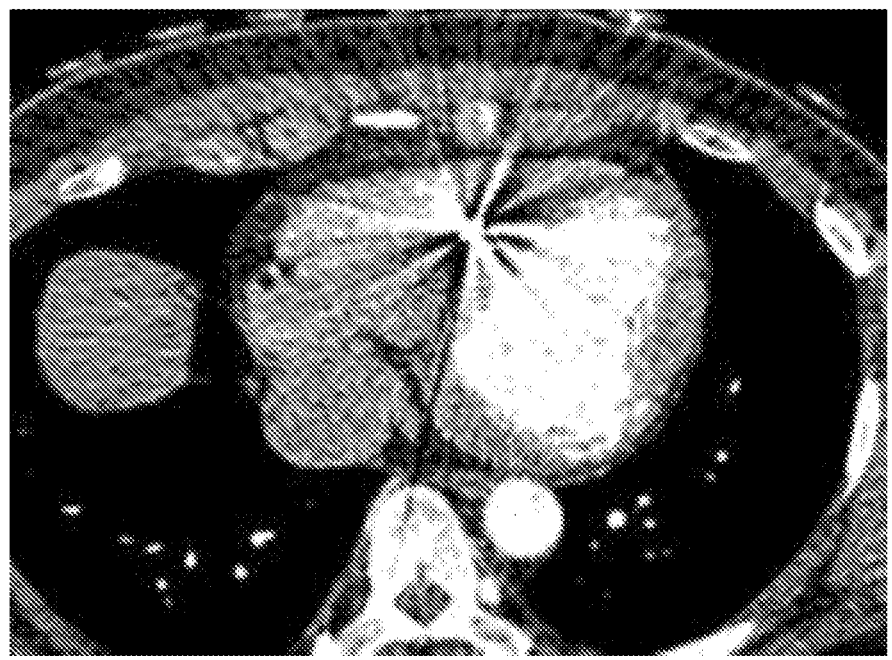
Figure 17:
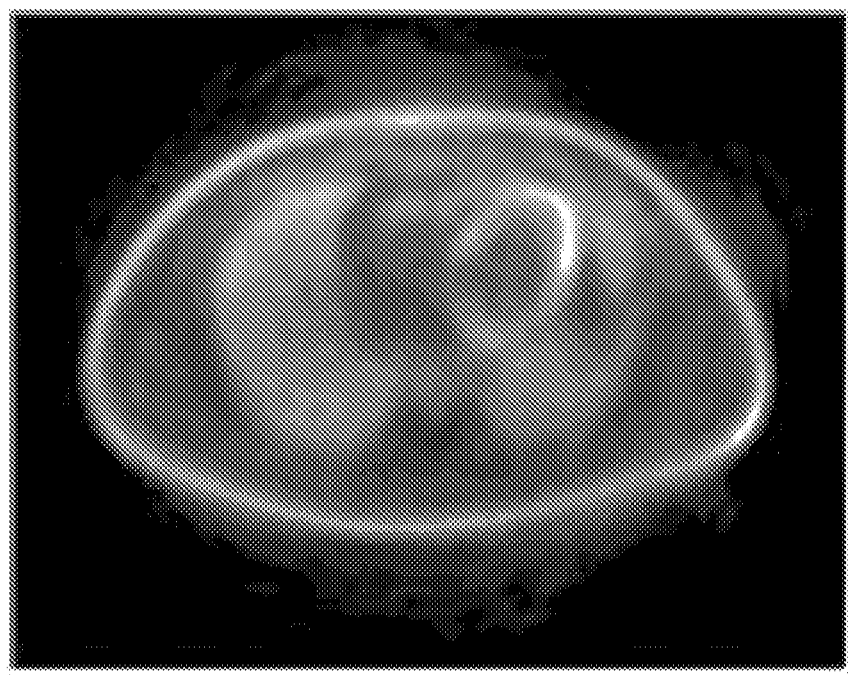
FIG. 17 shows a PET mapping of a patient in Example 3.

An MRI to identify wall motion disturbances found segments 11, 12, 5, and 6 to be hypokinetic. An MRI with gadolinium identified a dense scar at segments 5, 6, 11, 12, and 10 and a midmyocardial scar at segments 1 and 2, for example as seen in FIGS. 15A and 15B. A CT scan identified a thin region at segment 5, for example as seen in FIGS. 16A and 16B. A PET viability scan (not inflammatory) identified a region of decreased uptake at segments 5 and 11, for example as seen in FIG. 17.

As seen in FIGS. 18A, 18B, and 18C, ECGI identified segments 10 and 6 were earliest, so it was likely that endocardial segment 11 was the origin because, as seen in FIG. 3A, segment 11 is between the two epicardial breakthroughs at segments 10 and 6. Local EGMs with small R-waves were identified. Sinus rhythm abnormalities were identified in segments 10, 11, 6, and 5.

Figure 19:
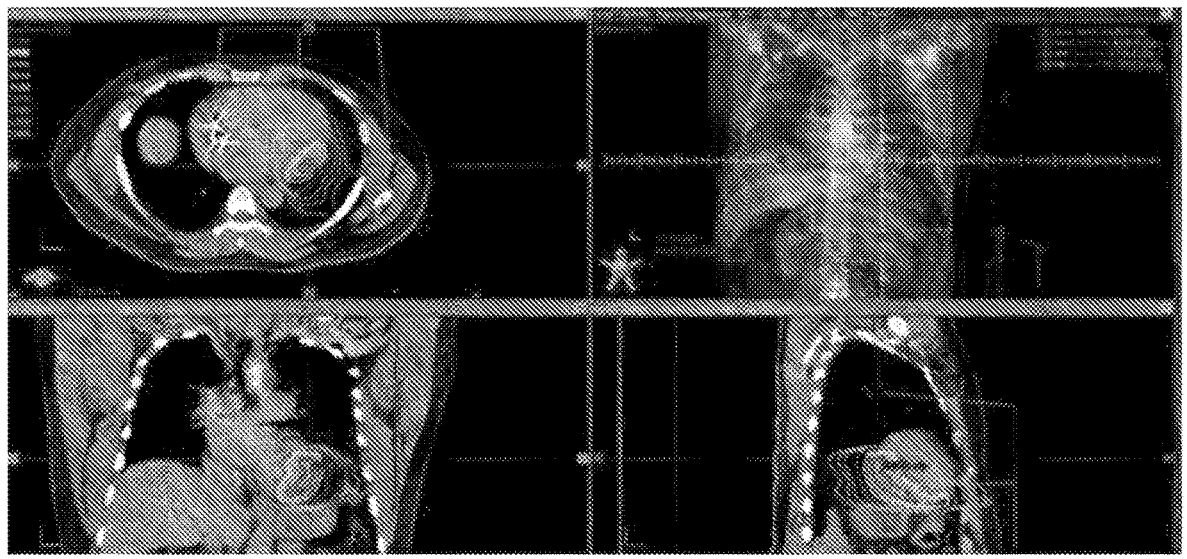
FIG. 19 shows contouring on an image of a patient in Example 3.

Contouring was done as seen in FIG. 19. The exit site was identified as segment 10. The nearby scar was identified as segments 11 and 12. Ablation was extended back to segment 5. The scar at segments 1 and 2 were not targeted. Segment 6 was not targeted because the ECG was entirely superiorly directed.

In general, the patient had a complex scar with a nearly transmural inferolateral scar, patchy scar transitions at inferior and anterolateral edges, and a midmyocardial "stripe" in anteroseptal base. Clinical VT was easily induced and ECGI and ECG maps to mid-inferior LV exit site (probably endocardial with two epicardial exits on ECGI). Targeting was made possible by ECG and ECGI, as prior cardiac mapping was not consistent with the MRI scar.

Figure 20A:
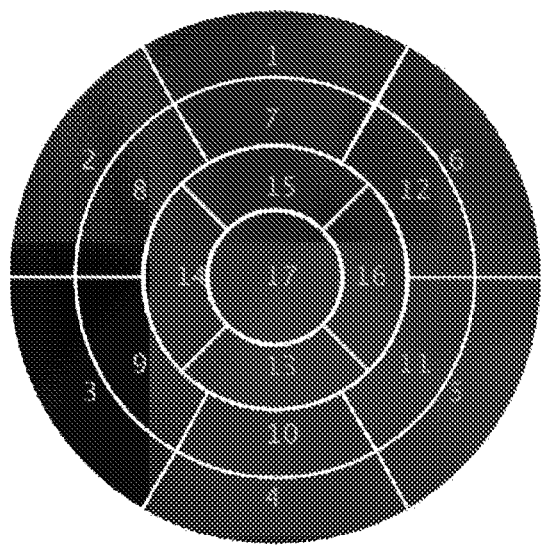
FIGS. 20A, 20B, 20C, 20D, 20E, and 20F show the segment abnormalities identified for the input mappings of Example 3.
Figure 20B:
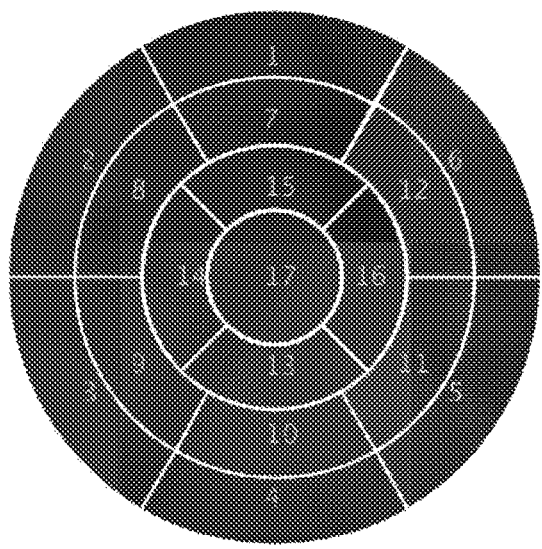
Figure 20C:
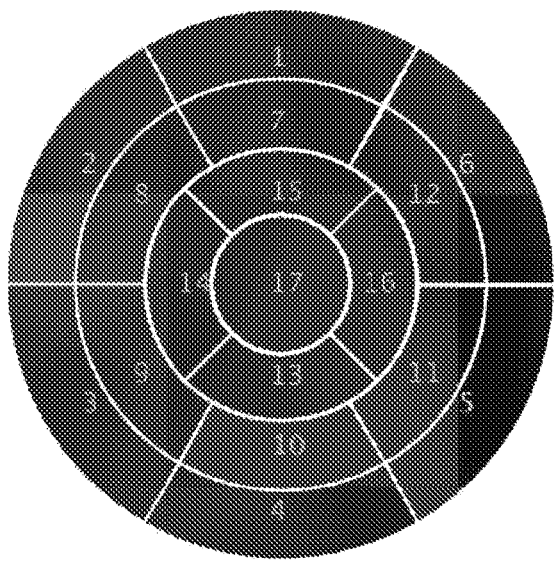
Figure 20D:
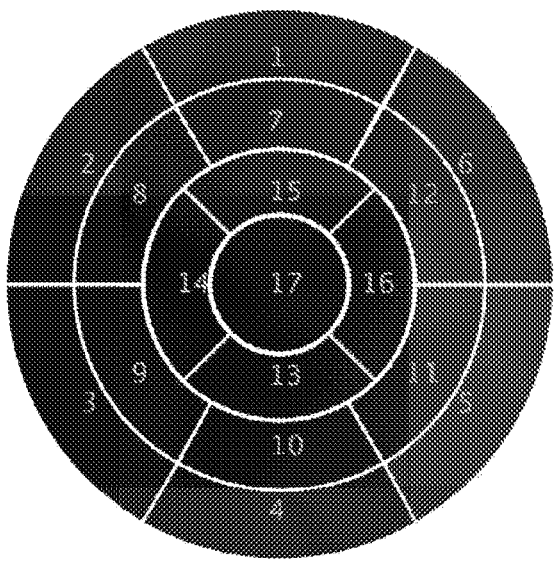
Figure 20E:
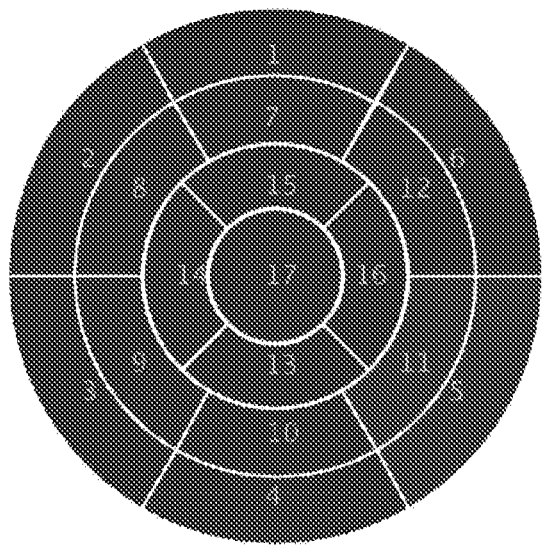
Figure 20F:
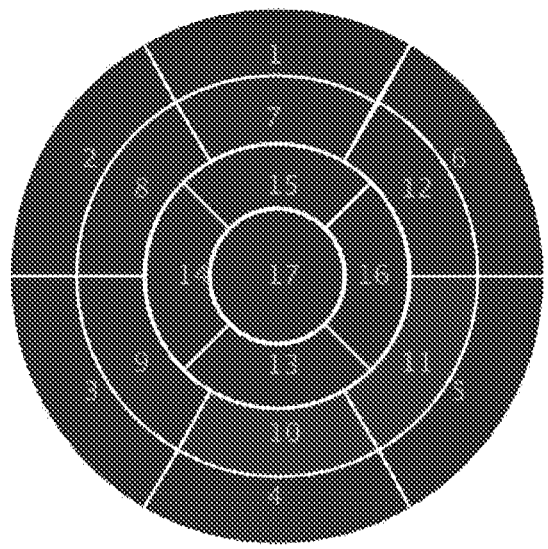
Figure 20G:
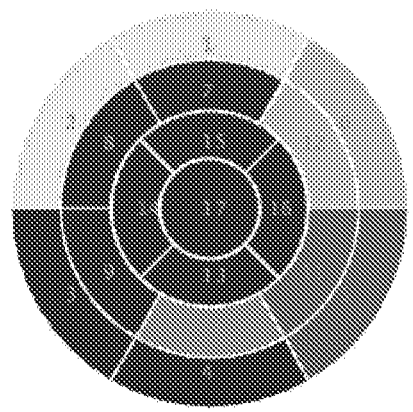
FIG. 20G shows the output of the method defining the one or more cardiac arrhythmia targets with color coded probabilities.

The mappings from FIGS. 14, 15A, 15B, 16A, 16C, 17, 18A, 18B, 18C, and 19 were input mappings into the method for determining one or more cardiac arrhythmia targets for ablation. FIGS. 20A, 20B, 20C, 20D, 20E, and 20F show the segment abnormalities identified from each of the input mappings (EKG, MRI motion, MRI scar, CT, PET, ECGI, respectively). FIG. 20G is the output of the method defining the one or more cardiac arrhythmia targets, showing the probability of each of the targets. For example, higher probability targets in red, moderate targets in orange, and lower targets in yellow. In this example, the final targets were segments 5, 10, 11, and 12.

Example 4

This example provides patient sample data and an example output of the method for determining segments for ablation. The patient was a 56 year old man with ischemic cardiomyopathy (LVEF<25%). The patient has had 4 prior catheter ablations and was on dual antiarrhythmics.

Figure 21A:
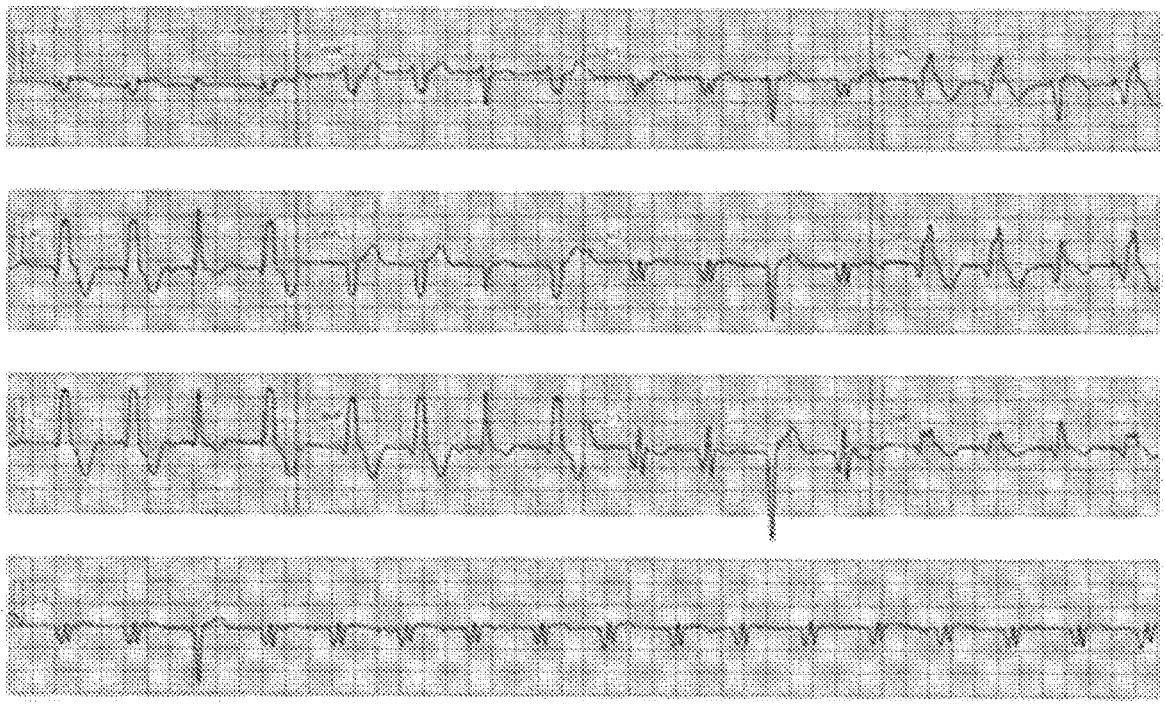
FIGS. 21A and 21B show ECGs of a patient in Example 4.
Figure 21B:
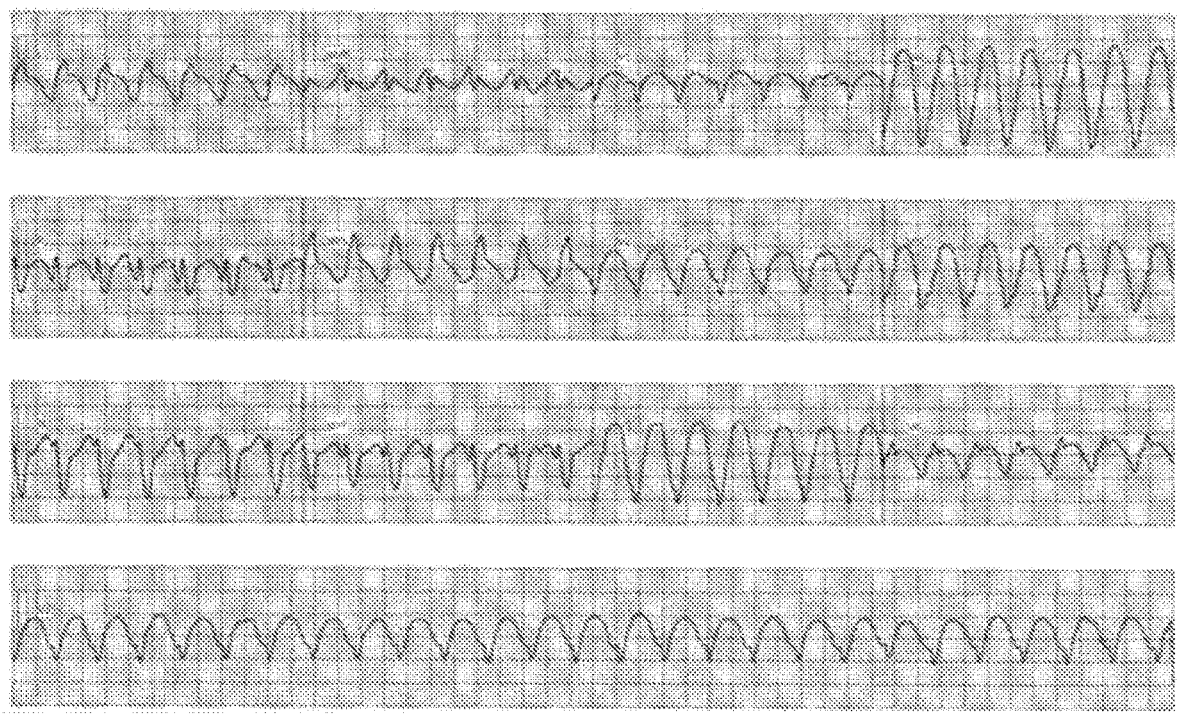

The left ventricle was segmented as seen in FIG. 3A. An ECG of the patient is shown in FIG. 21A which shows a VT1 at segment 7 and in FIG. 21B which shows a VT2 at segment 14.

Figure 22:
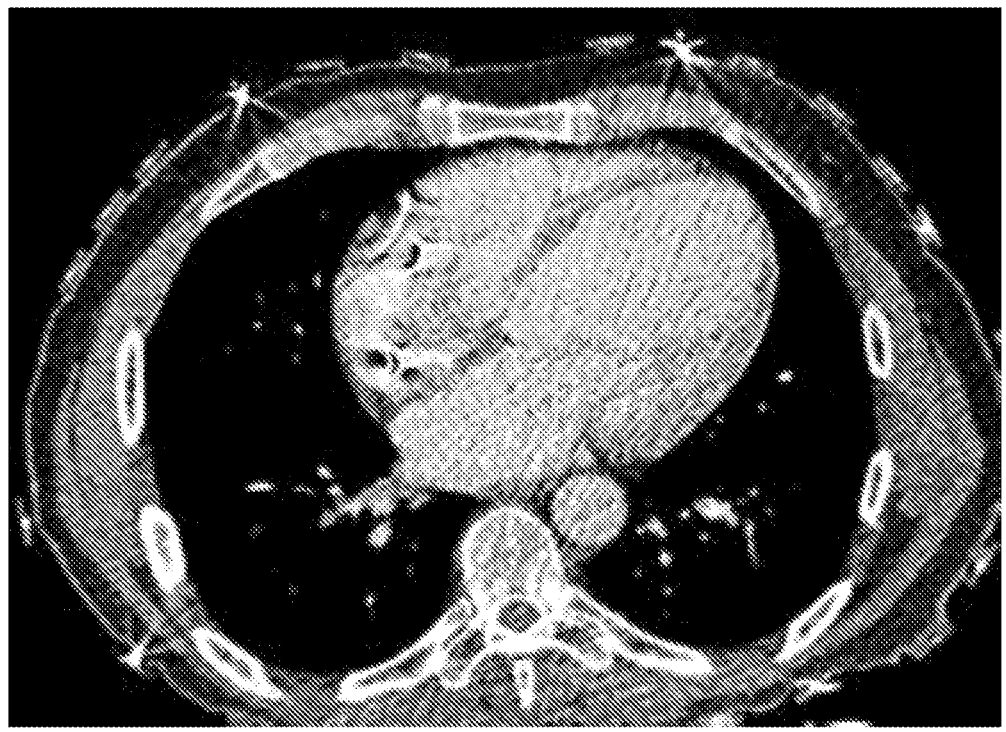
FIG. 22 shows a CT mapping of a patient in Example 4.
Figure 23A:
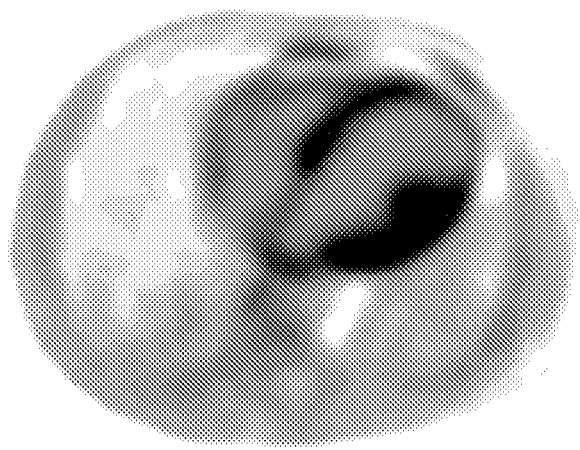
FIGS. 23A and 23B show PET mappings of a patient in Example 4.
Figure 23B:
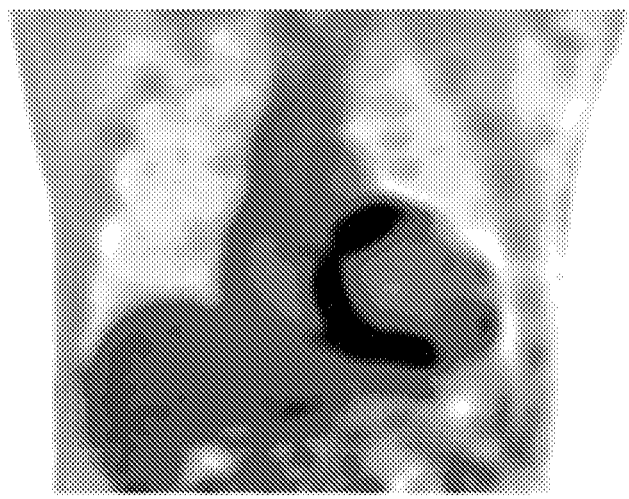

MRI's were not obtained because the patient's pacemaker was in the elective replacement interval (ERI). A CT scan identified a thinned apical aneurysm at segments 7, 13, 14, 15, 16, and 17, for example as seen in FIG. 22. A PET scan identified a large anterior apical aneurysm at segments 7, 13, 14, 15, 16, and 17, for example as seen in FIGS. 23A and 23B.

Figure 24A:
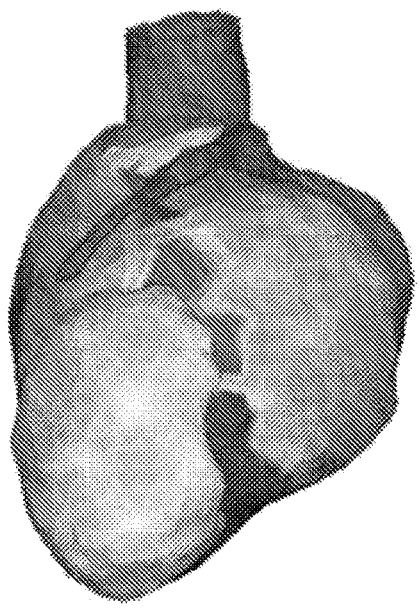
FIGS. 24A, 24B, 24C, and 24D show ECGI mappings for VT1 and VT2 of the patient in Example 4.
Figure 24B:
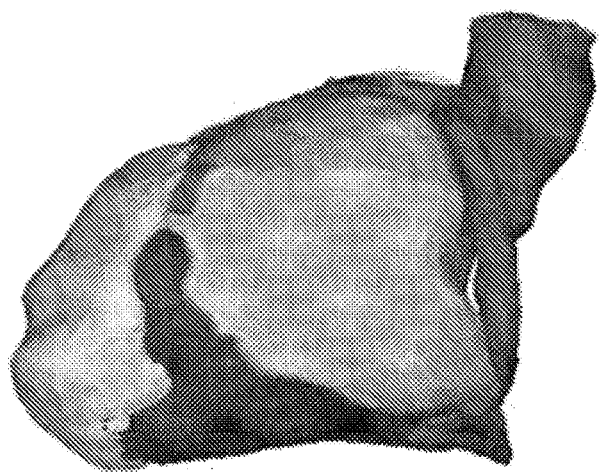
Figure 24C:
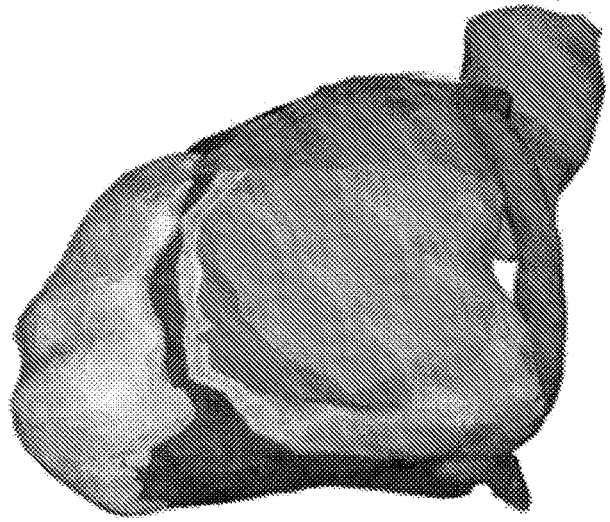
Figure 24D:
Figure 24E:
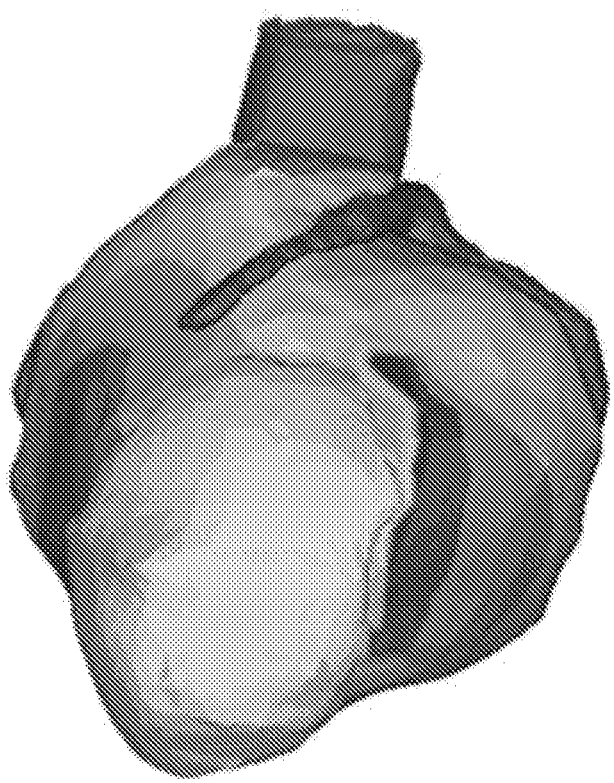
FIGS. 24E and 24F show additional ECGI mappings for the patient in Example 4.
Figure 24F:
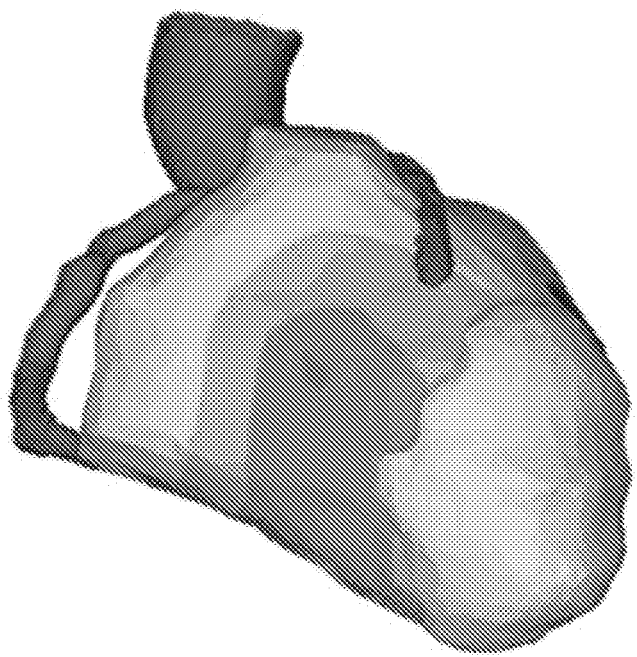

As seen in FIGS. 24A, 24B, 24C, and 24D, ECGI identified VT1 in segments 7, 12, 13, and 16 and VT2 in segments 15 and 16. In addition, ECGI identified a sinus rhythm, large apical aneurysm in segments 13, 14, 15, 16, and 17 and isochronal late activation in segments 13 and 16, as seen in FIGS. 24E and 24F.

Figure 25A:
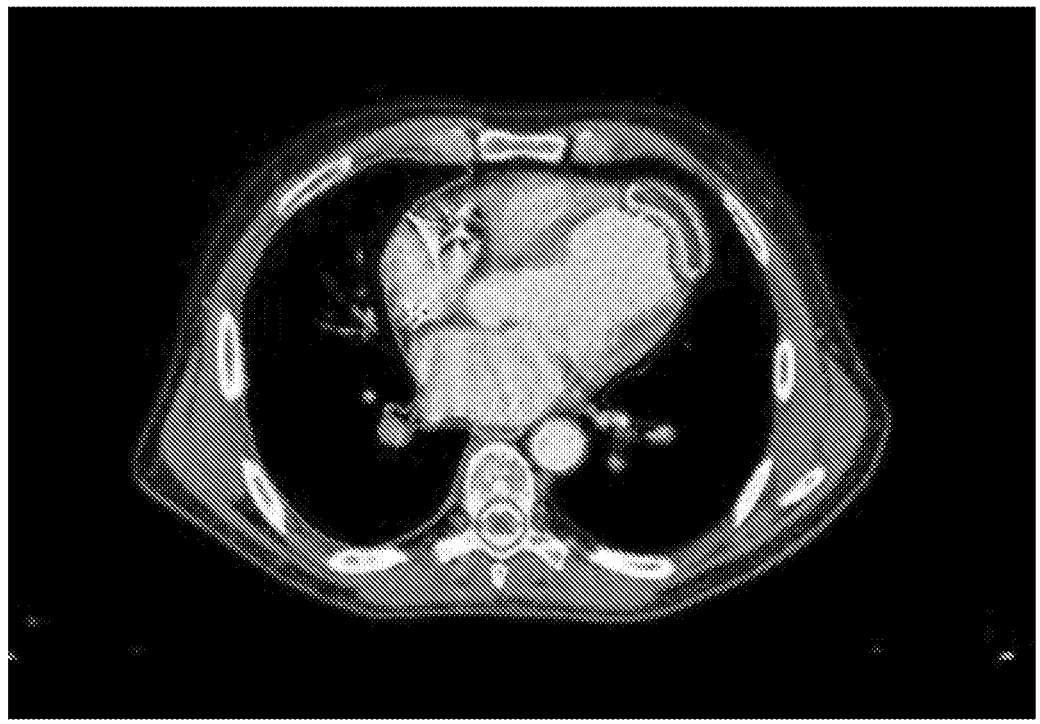
FIGS. 25A and 25B show contouring on an image of the patient in Example 4.
Figure 25B:

Contouring was done as seen in FIGS. 25A and 25B. In general, the patient had a large anterior apical scar with two different VTs, both exiting out of two different edges from the scar and interesting sinus rhythm activation that aligns with the VT sites. ECGI agrees with VT1 ECG, but not VT2 ECG. The target treatment decision balanced scar homogenization (large) vs. a more focused approach. The VTs on 12-lead are two different regions, rather far way, requiring a more broad ablation. Full scar homogenization would require segments 7, 13, 14, 15, 16, and 17, while ECGI alone would recommend the lateral edge of the scar, only segments 13, 15, 16.

Figure 26A:
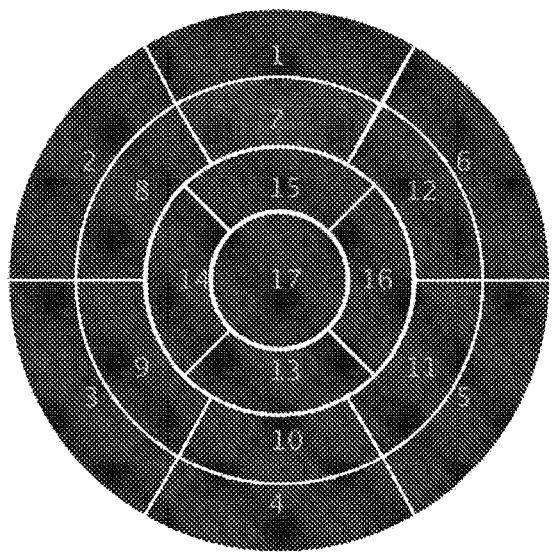
FIGS. 26A, 26B, 26C, 26D, 26E, 26F, 26G, and 26H show the segment abnormalities identified from each of the input mappings for the patient in Example 4.
Figure 26B:
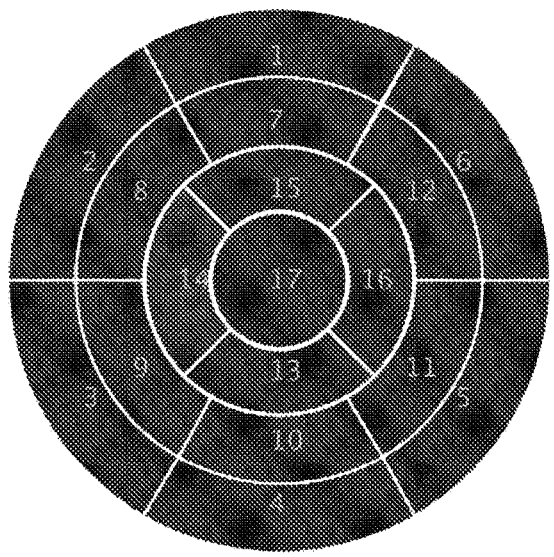
Figure 26C:
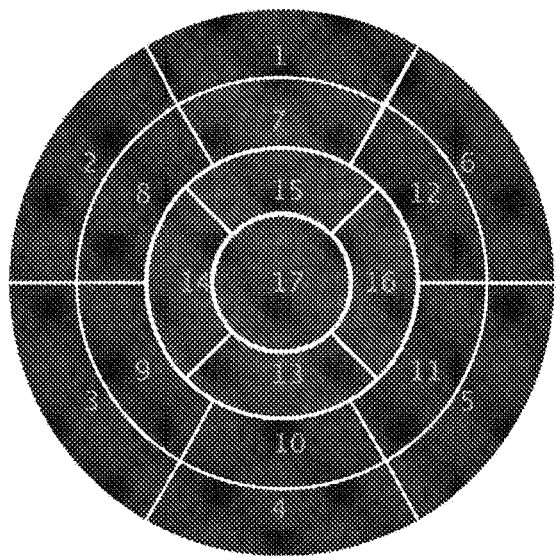
Figure 26D:
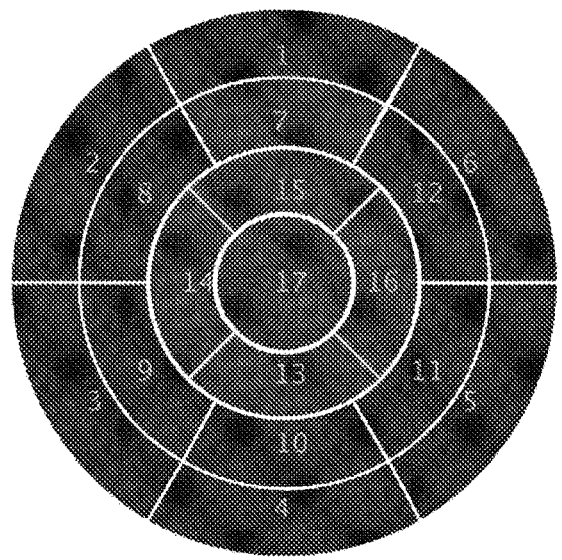
Figure 26E:
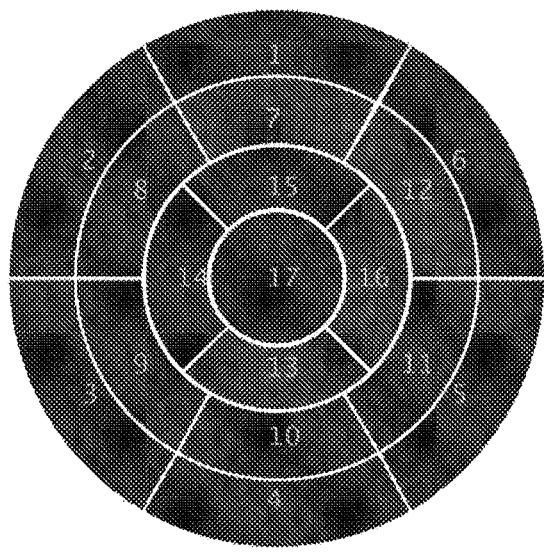
Figure 26F:
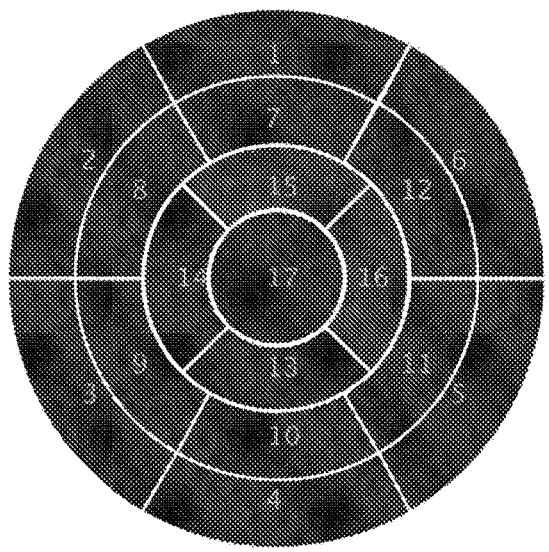
Figure 26G:
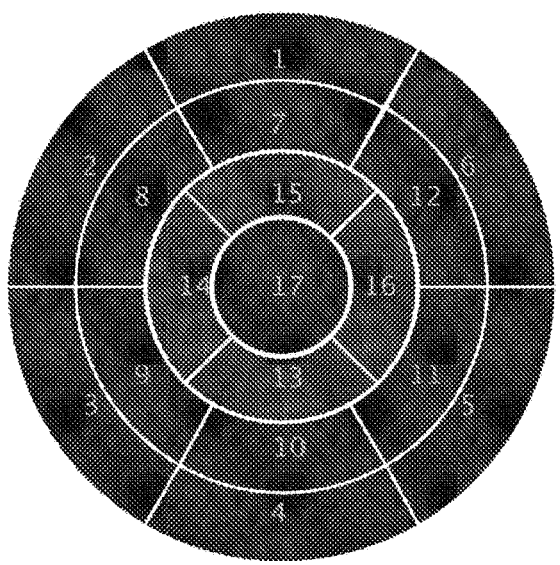
Figure 26H:
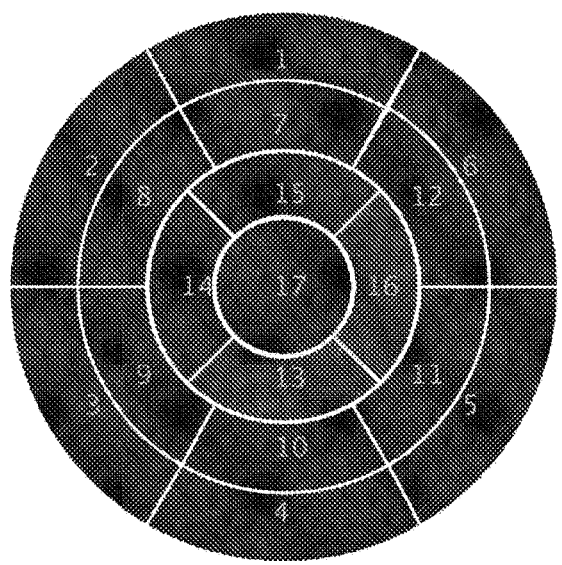
Figure 26I:
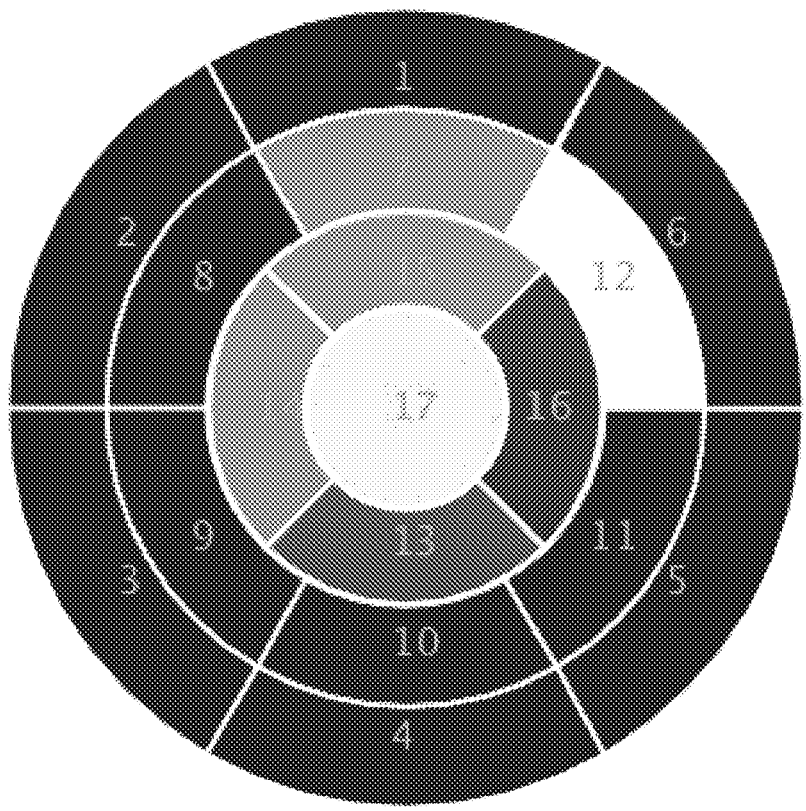
FIG. 26I shows the output of the method defining the one or more cardiac arrhythmia targets with color coded probabilities.

The mappings from FIGS. 21A, 21B, 22, 23A, 23B, 24A, 24B, 24C, 24D, 24E, 24F, 25A, and 25B were input mappings into the method for determining one or more cardiac arrhythmia targets for ablation. FIGS. 26A, 26B, 26C, 26D, 26E, 26F, 26G, and 26H show the segment abnormalities identified from each of the input mappings (EKG for VT1, EKG for VT2, CT, PET, ECGI for VT1, ECGI for VT2, ECGI for sinus rhythm scar, and ECGI for sinus rhythm latest activation, respectively). FIG. 26I is the output of the method defining the one or more cardiac arrhythmia targets, showing the probability of each of the targets. For example, higher probability targets in red, moderate targets in orange, and lower targets in yellow. In this example, the final targets were segments 7, 13, 14, 15, 16, and 17.

What is claimed is:

1. A method for determining a cardiac arrhythmia target for ablation, the method comprising:
    receiving a plurality of mappings of a heart of a patient, the plurality of mappings selected from an electrical mapping, an anatomic mapping, and a functional mapping;
    identifying a predetermined number of segments on each mapping of the plurality of mappings, wherein for each mapping the predetermined number of segments encompass the entire mapping, and each segment corresponds to a different area of the heart;
    identifying a first abnormality in a first mapping of the plurality of mappings;
    selecting any segments of the first mapping in which the first abnormality is located;
    identifying a second abnormality in a second mapping of the plurality of mappings;
    selecting any segments of the second mapping in which the second abnormality is located;
    combining the plurality of mappings;
    selecting the cardiac arrhythmia target based on any segments in the combined plurality of mappings in which selected segments containing the identified first abnormality and selected segments containing the identified second abnormality overlap one another;
    providing the selected cardiac arrhythmia target to a system operable to carry out ablation of the selected cardiac arrhythmia target; and
    performing ablation on the patient based on the received selected cardiac arrhythmia target.

2. The method of claim 1, wherein identifying the first abnormality comprises identifying one or more contours on the first mapping that includes the first abnormality.

3. The method of claim 1, wherein identifying the first abnormality comprises receiving a manual identification of the first abnormality from a user.

4. The method of claim 1, wherein selecting the cardiac arrhythmia target comprises selecting the cardiac arrhythmia target based on any segments in the combined plurality of mappings in which selected segments containing the identified first abnormality and selected segments containing the identified second abnormality overlap one another, and additional data about the patient.

5. The method of claim 1, wherein ablating the cardiac arrhythmia target comprises non-invasive ablation of the cardiac arrhythmia target.

6. The method of claim 1, further comprising weighting each mapping of the received plurality of mappings, and wherein selecting the cardiac arrhythmia target comprises selecting the cardiac arrhythmia target based on any segments in the combined plurality of mappings in which selected segments containing the identified first abnormality and selected segments containing the identified second abnormality overlap one another, and the weighting of the received plurality of mappings.

7. The method of claim 1, further comprising determining a confidence score of the combined mappings, and wherein selecting the cardiac arrhythmia target comprises selecting the cardiac arrhythmia target based on any segments in the combined plurality of mappings in which selected segments containing the identified first abnormality and selected segments containing the identified second abnormality overlap one another, and the confidence score.

8. The method of claim 1, wherein the electrical mapping is an electrocardiograph image, the anatomic mapping is at least one of a computer tomography image or a magnetic resonance image, and the functional mapping is at least one of a photo emission computed tomographic image, a positron emission tomography image or an echocardiogram image.

9. The method of claim 1, further comprising generating a decision support module.

10. The method of claim 9, wherein the decision support module comprises an output of the cardiac arrhythmia target and one or more of a description of a scar pattern, a description of a scar burden size and location, a suggested volume to achieve ablation, a confidence score of the combined mappings, a listing of at-risk structures, a general recommendation, an expected success rate with non-invasive therapy, or an expected success rate with alternative treatment modalities.

11. The method of claim 1, wherein selecting the cardiac arrhythmia target comprises selecting the cardiac arrhythmia target based on any segments in the combined plurality of mappings in which selected segments containing the identified first abnormality and selected segments containing the identified second abnormality overlap one another, and additional data from previous patients.

12. At least one non-transitory computer readable medium storing instructions which when executed by at least one processor, cause the at least one processor to:
    receive a plurality of mappings of a heart of a patient, the plurality of mappings selected from an electrical mapping, an anatomic mapping, and a functional mapping;
    identify a predetermined number of segments on each mapping of the plurality of mappings, wherein for each mapping, the predetermined number of segments encompass the entire mapping, and each segment corresponds to a different are of the heart of the patient;
    identify first abnormality in a first mapping of the plurality of mappings;
    select any segments of the first mapping in which the first abnormality is located;
    identify a second abnormality in a second mapping of the plurality of mappings;
    select any segments of the second mapping in which the second abnormality is located;
    combine the plurality of mappings;
    select a cardiac arrhythmia target based on any segments in the combined plurality of mappings in which selected segments containing the identified first abnormality and selected segments containing the identified second abnormality overlap one another;

provide the selected cardiac arrhythmia target to a system operable to carry out ablation of the selected cardiac arrhythmia target; and perform ablation on the patient based on the received selected cardiac arrhythmia target.

13. The at least one non-transitory computer readable medium of claim 12, further comprising instructions, which when executed by the at least one processor, cause the at least one processor to select the cardiac arrhythmia target for ablation based on any segments in the combined plurality of mappings in which selected segments containing the identified first abnormality and selected segments containing the identified second abnormality overlap one another, and additional data about the patient.

14. The at least one non-transitory computer readable medium of claim 12, further comprising instructions, which when executed by the at least one processor, cause the at least one processor to weight each mapping of the received plurality of mappings, and to select the cardiac arrhythmia target based on any segments in the combined plurality of mappings in which selected segments containing the identified first abnormality and selected segments containing the identified second abnormality overlap one another, and the weighting of the received plurality of mappings.

15. The at least one non-transitory computer readable medium of claim 12, further comprising instructions, which when executed by the at least one processor, cause the at least one processor to determine a confidence score of the combined mappings, and select the cardiac arrhythmia target based on any segments in the combined plurality of mappings in which selected segments containing the identified first abnormality and selected segments containing the identified second abnormality overlap one another, and the confidence score.

16. The at least one non-transitory computer readable medium of claim 12, wherein the electrical mapping is an electrocardiograph image, the anatomic mapping is at least one of a computer tomography image or a magnetic resonance image, and the functional mapping is at least one of a photo emission computed tomographic image, a positron emission tomography image or an echocardiogram image.

17. The at least one non-transitory computer readable medium of claim 12, further comprising instructions, which when executed by the at least one processor, cause the at least one processor to:

receive one or more clinical mappings including at least one of demographics, surgical history, information about ventricular tachycardia and prior electroanatomical mappings; and determine an updated cardiac arrhythmia target for ablation based on the combined plurality of mappings and the one or more clinical mappings.

18. The at least one non-transitory computer readable medium of claim 12, further comprising instructions, which when executed by the at least one processor, cause the at least one processor to generate a decision support module.

19. The at least one non-transitory computer readable medium of claim 18, wherein the decision support module comprises an output of the cardiac arrhythmia target and one or more of a description of a scar pattern, a description of a scar burden size and location, a suggested volume to achieve ablation, a confidence score of the combined mappings, a listing of at-risk structures, a general recommendation, an expected success rate with non-invasive therapy, or an expected success rate with alternative treatment modalities.

* * * * *